(12) United States Patent
Vyssotski et al.

(10) Patent No.: US 11,134,864 B2
(45) Date of Patent: Oct. 5, 2021

(54) TRACKING METHOD AND SYSTEM FOR SMALL ANIMAL RESEARCH

(71) Applicants: Alexei L. Vyssotski, Zurich (CH); Dmitri L. Vyssotski, Tarrytown, NY (US)

(72) Inventors: Alexei L. Vyssotski, Zurich (CH); Dmitri L. Vyssotski, Tarrytown, NY (US)

( * ) Notice: Subject to any disclaimer, the term of this patent is extended or adjusted under 35 U.S.C. 154(b) by 0 days.

(21) Appl. No.: 15/445,350

(22) Filed: Feb. 28, 2017

(65) Prior Publication Data

US 2017/0248696 A1 Aug. 31, 2017

Related U.S. Application Data

(60) Provisional application No. 62/361,643, filed on Jul. 13, 2016.

(51) Int. Cl.
*G01S 1/70* (2006.01)
*G01S 5/18* (2006.01)
(Continued)

(52) U.S. Cl.
CPC ........... *A61B 5/1113* (2013.01); *G01S 1/7036* (2019.08); *G01S 1/82* (2013.01);
(Continued)

(58) Field of Classification Search
CPC .................................. G01S 1/725; G01S 5/30
See application file for complete search history.

(56) References Cited

U.S. PATENT DOCUMENTS 4,796,198 A 1/1989 Karlan
4,830,489 A 5/1989 Cain
(Continued)

FOREIGN PATENT DOCUMENTS

EP 1166042 3/2007

OTHER PUBLICATIONS

Ardekani, R., Biyani, A., Dalton, J. E., Saltz, J. B., Arbeitman, M. N., Tower, J., . . . Tavaré, S. (2013). Three-dimensional tracking and behaviour monitoring of multiple fruit flies. Journal of the Royal Society, Interface / the Royal Society, 10(78), 20120547. http://doi.org/10.1098/rsif.2012.0547.

(Continued)

*Primary Examiner* — Daniel J Colilla

(57) ABSTRACT

A method and system for detecting a position of an animal in laboratory conditions based on ultrasonic tracking is disclosed. The animal has an attached mobile device comprising an ultrasonic receiver. Ultrasonic signals emitted from ultrasonic emitters either have an envelope with a shape that is chosen with the first derivative restricted by condition $|dE/dt|<A/T$ and/or with the second derivative restricted by condition $|d^2E/dt^2|<A/T^2$, wherein E(t) is the envelope curve, t is time, A is the maximum amplitude of the ultrasonic signals and T is the period of the base frequency of the ultrasonic signals; or oscillations of voltage or current of ultrasonic emitters during signal transmission have envelopes described by a special function for amplitude of the oscillations. The mobile device receives an optical or radio synchronization signals from signal sources connected with the ultrasonic emitters. Analog or digital filters are used to separate ultrasonic signals from animal's vocalization. In some embodiments coordinates are obtained by using optical scanning sources with ultrasonic emitter placed at the axes of rotation of one or two emitted rotating planar scanning light beams. Tracking for multiple animals is disclosed.

33 Claims, 43 Drawing Sheets

(51) Int. Cl.

| | |
|---|---|
| *G01S 5/30* | (2006.01) |
| *A61B 5/11* | (2006.01) |
| *G01S 5/02* | (2010.01) |
| *G01S 5/16* | (2006.01) |
| *G01S 1/82* | (2006.01) |
| *G01S 11/16* | (2006.01) |

(52) U.S. Cl.
CPC .......... *G01S 5/0257* (2013.01); *G01S 5/0263* (2013.01); *G01S 5/16* (2013.01); *G01S 5/18* (2013.01); *G01S 5/30* (2013.01); *G01S 11/16* (2013.01); *A61B 2503/40* (2013.01); *A61B 2503/42* (2013.01); *G01S 2201/01* (2019.08)

(56) References Cited

U.S. PATENT DOCUMENTS

| | | | |
|---|---|---|---|
| 5,100,229 | A | 3/1992 | Lundberg |
| 5,110,202 | A | 5/1992 | Dornbusch |
| 5,247,487 | A | 9/1993 | Beliveau |
| 5,729,475 | A | 3/1998 | Romanik |
| 5,884,239 | A | 3/1999 | Romanik |
| 6,198,528 | B1 | 3/2001 | Maynard |
| 6,452,668 | B1 | 9/2002 | Pratt |
| 6,535,282 | B2 | 3/2003 | Hedges |
| 7,406,000 | B2 | 7/2008 | Lee |
| 8,160,688 | B2 | 4/2012 | Vyssotski |
| 2013/0030931 | A1* | 1/2013 | Moshfeghi .............. H04W 4/80 705/16 |
| 2015/0063072 | A1 | 3/2015 | Deng |
| 2016/0266235 | A1* | 9/2016 | Hannon ............. H04M 1/72572 |
| 2017/0019525 | A1* | 1/2017 | Hannon .................... G01S 5/18 |
| 2017/0168135 | A1* | 6/2017 | Want ....................... G01S 1/042 |
| 2017/0208565 | A1* | 7/2017 | Lowe ........................ G01S 5/30 |
| 2018/0013871 | A1* | 1/2018 | Robillard ................ B60R 11/02 |

OTHER PUBLICATIONS

Bowmaker, J. K. (2008). Evolution of vertebrate visual pigments. Vision Research, 48(20), 2022-2041. http://doi.org/10.1016/j.visres.2008.03.025.

Brudzynski, S. (2010). Handbook of mammalian vocalization: an integrative neuroscience approach. Academic.

Brudzynski, S. M., & Barnabi, F. (1996). Contribution of the ascending cholinergic pathways in the production of ultrasonic vocalization in the rat. Behavioural Brain Research, 80(1), 145-152. http://doi.org/10.1016/0166-4328(96) 00029-0.

Campbell, A. L., Naik, R. R., Sowards, L., & Stone, M. O. (2002). Biological infrared imaging and sensing. Micron (Oxford, England: 1993), 33(2), 211-25. Retrieved from http://www.ncbi.nlm.nih.gov/pubmed/11567889.

Carden, S. E., & Hofer, M. A. (1992). Effect of a social companion on the ultrasonic vocalizations and contact responses of 3-day-old rat pups. Behavioral Neuroscience, 106(2), 421-6. Retrieved from http://www.ncbi.nlm.nih.gov/pubmed/1590959.

Catarinucci, L., Colella, R., Mainetti, L., Patrono, L., Pieretti, S., Sergi, I., & Tarricone, L. (2014). Smart RFID Antenna System for Indoor Tracking and Behavior Analysis of Small Animals in Colony Cages. IEEE Sensors Journal, 14(4), 1198-1206. http://doi.org/10.1109/JSEN.2013.2293594.

Crawley, J. N., Szara, S., Pryor, G. T., Creveling, C. R., & Bernard, B. K. (1982). Development and evaluation of a computer-automated color tv tracking system for automatic recording of the social and exploratory behavior of small animals. Journal of Neuroscience Methods, 5(3), 235-247. http://doi.org/10.1016/0165-0270(82)90074-7.

Dell'omo, G., Shore, R. F., & Lipp, H. P. (1998). An automated system, based on microchips, for monitoring individual activity in wild small mammals. The Journal of Experimental Zoology, 280(1), 97-9. Retrieved from http://www.ncbi.nlm.nih.gov/pubmed/9437856.

Deng, Z. D., Carlson, T. J., Li, H., Xiao, J., Myjak, M. J., Lu, J., . . . Eppard, M. B. (2015). An injectable acoustic transmitter for juvenile salmon. Scientific Reports, 5, 8111. http://doi.org/10.1038/srep08111.

Deng, Z. D., Weiland, M. A., Fu, T., Seim, T. A., LaMarche, B. L, Choi, E. Y., . . . Eppard, M. B. (2011). A cabled acoustic telemetry system for detecting and tracking juvenile salmon: part 2. Three-dimensional tracking and passage outcomes. Sensors (Basel, Switzerland), 11(6), 5661-76. http://doi.org/10.3390/s110605661.

Fukunaga, T., Kubota, S., Oda, S., & Iwasaki, W. (2015). GroupTracker: Video tracking system for multiple animals under severe occlusion. Computational Biology and Chemistry, 57, 39-45. http://doi.org/10.1016/j.compbiolchem.2015.02.006.

Ingraham, J. M., Deng, Z. D., Li, X., Fu, T., McMichael, G. A., & Trumbo, B. A. (2014). A fast and accurate decoder for underwater acoustic telemetry. The Review of Scientific Instruments, 85(7), 74903. http://doi.org/10.1063/1.4891041.

Kelly, J. B., & Masterton, B. (1977). Auditory sensitivity of the albino rat. Journal of Comparative and Physiological Psychology, 91(4), 930-6. Retrieved from http://www.ncbi.nlm.nih.gov/pubmed/893752.

Markweg, E., Nguyen, T. T., Weinberger, S., Ament, C., & Hoffmann, M. (2011). Development of a Miniaturized Multisensory Positioning Device for Laser Dicing Technology. Physics Procedia, 12, 387-395. http://doi.org/10.1016/j.phpro.2011.03.148.

Miller, C. T., Mandel, K., & Wang, X. (2010). The communicative content of the common marmoset phee call during antiphonal calling. American Journal of Primatology, 72(11), 974-80. http://doi.org/10.1002/ajp.20854.

Ochi, T., Higuchi, Y., & Satta, T. (1994). A three-dimensional positioning system using laser beams and its application to the undulation measurement of a golf course green. In Automation and Robotics in Construction Xi (pp. 319-325). http://doi.org/10.1016/B978-0-444-82044-0.50047-3.

Ou-Yang, T.-H., Tsai, M.-L., Yen, C.-T., & Lin, T.-T. (2011). An infrared range camera-based approach for three-dimensional locomotion tracking and pose reconstruction in a rodent. Journal of Neuroscience Methods, 201(1), 116-23. http://doi.org/10.1016/j.jneumeth.2011.07.019.

Palczewska, G., Vinberg, F., Stremplewski, P., Bircher, M. P., Salom, D., Komar, K., . . . Palczewski, K. (2014). Human infrared vision is triggered by two-photon chromophore isomerization. Proceedings of the National Academy of Sciences, 111(50), E5445-E5454. http://doi.org/10.1073/pnas.1410162111.

Roberts, L. H. (1975). The rodent ultrasound production mechanism. Ultrasonics, 13(2), 83-8. Retrieved from http://www.ncbi.nlm.nih.gov/pubmed/1167711.

Steiner, I., Bürgi, C., Werffeli, S., Dell'Omo, G., Valenti, P., Tröster, G., . . . Lipp, H. P. (2000). A GPS logger and software for analysis of homing in pigeons and small mammals. Physiology & Behavior, 71(5), 589-96. Retrieved from http://www.ncbi.nlm.nih.gov/pubmed/11239679.

Uei-Ming Jow, U.-M., Kiani, M., Xueliang Huo, X., & Ghovanloo, M. (2012). Towards a Smart Experimental Arena for Long-Term Electrophysiology Experiments. IEEE Transactions on Biomedical Circuits and Systems, 6(5), 414-423. http://doi.org/10.1109/TBCAS.2012.2211872.

Vatine, J. J., Ratner, A., Dvorkin, M., & Seltzer, Z. (1998). A novel computerized system for analyzing motor and social behavior in groups of animals. Journal of Neuroscience Methods, 85(1), 1-11. Retrieved from http://www.ncbi.nlm.nih.gov/pubmed/9874135.

von Hünerbein, K., Hamann, H. J., Rüter, E., & Wiltschko, W. (2000). A GPS-based system for recording the flight paths of birds. Die Naturwissenschaffen, 87(6), 278-9. Retrieved from http://www.ncbi.nlm.nih.gov/pubmed/10929293.

Wang, Z., Mastrogiacomo, L., Franceschini, F., & Maropoulos, P. (2011). Experimental comparison of dynamic tracking performance of iGPS and laser tracker. The International Journal of Advanced Manufacturing Technology, 56 (1-4), 205-213. http://doi.org/10.1007/s00170-011-3166-0.

Wöhr, M., & Schwarting, R. K. W. (2013). Affective communication in rodents: ultrasonic vocalizations as a tool for research on emotion

(56) References Cited

OTHER PUBLICATIONS and motivation. Cell and Tissue Research, 354(1), 81-97. http://doi.org/10.10071/s00441-013-1607-9.

Yayan, U., Yucel, H., & Yazici, A. (2015). A Low Cost Ultrasonic Based Positioning System for the Indoor Navigation of Mobile Robots. Journal of Intelligent & Robotic Systems, 78(3-4), 541-552. http://doi.org/10.1007/s10846-014-0060-7.

* cited by examiner

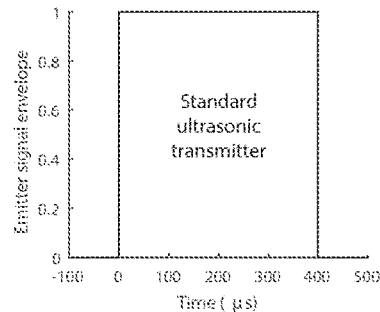
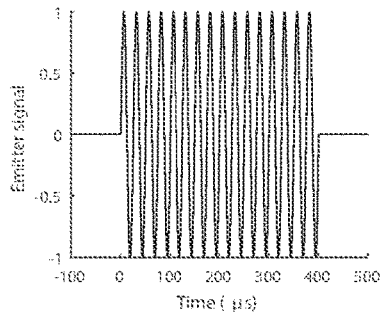
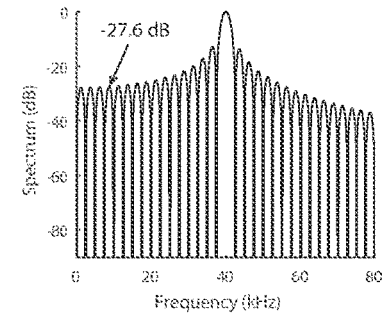
FIG. 13A  FIG. 13B  FIG. 13C
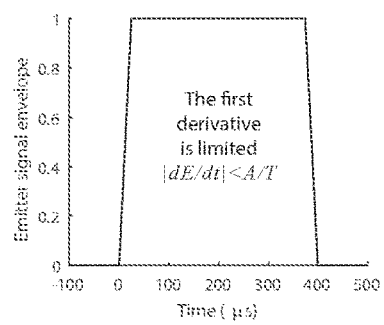
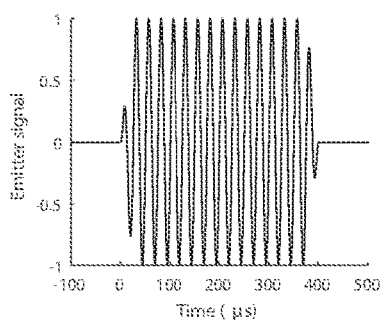
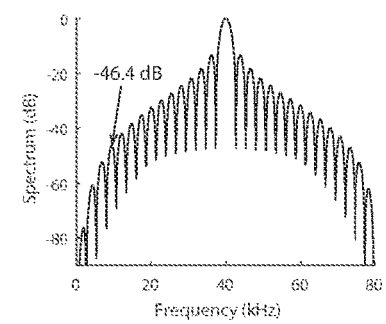
FIG. 13D  FIG. 13E  FIG. 13F
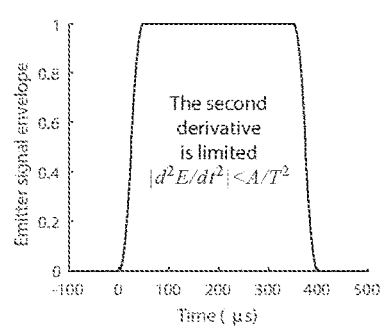
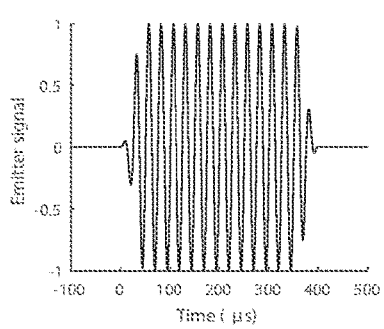
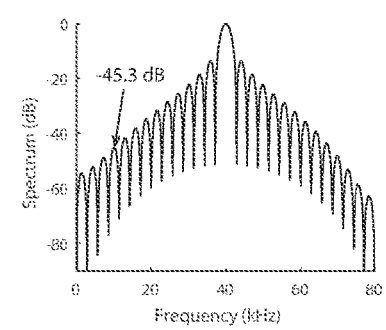
FIG. 13G  FIG. 13H  FIG. 13I Standard ultrasonic transmitter Animal-friendly ultrasonic transmitter Asymmetrically driven ultrasonic emitter Ultrasonic emitter driven by PWM signal

TRACKING METHOD AND SYSTEM FOR SMALL ANIMAL RESEARCH

RELATED U.S. APPLICATION DATA

Provisional application No. 62/361,643 filed on Jul. 13, 2016.

REFERENCES CITED

U.S. Patent Documents

| | | | |
|---|---|---|---|
| 4,796,198 | January 1989 | Karlan et al. | 364/513 |
| 4,830,489 | May 1989 | Cain et al. | 356/73 |
| 5,100,229 | April 1992 | Lundberg et al. | 356/1 |
| 5,110,202 | May 1992 | Dornbusch et al. | 356/1 |
| 5,247,487 | September 1993 | Beliveau et al. | 367/99 |
| 5,729,475 | March 1998 | Romanik | 364/559 |
| 5,884,239 | March 1999 | Romanik | 702/150 |
| 6,198,528 | March 2001 | Maynard | 356/141.1 |
| 6,452,668 | September 2002 | Pratt | 356/141.4 |
| 6,535,282 | March 2003 | Hedges et al. | 356/141.3 |
| 7,406,000 | July 2008 | Lee | 367/127 |
| 8,160,688 | April 2012 | Vyssotski et al. | 600/544 |
| US 2015/0063072A1 | May 2015 | Deng et al. | 367/134 |

Foreign Patent Documents

| | | | |
|---|---|---|---|
| EP 1,166,042 | March 2000 | Hedges et al. | G01C 15/00 |

Other Publications

Ardekani, R., Biyani, A., Dalton, J. E., Saltz, J. B., Arbeitman, M. N., Tower, J., . . . Tavaré, S. (2013). Three-dimensional tracking and behaviour monitoring of multiple fruit flies. Journal of the Royal Society, Interface/the Royal Society, 10(78), 20120547. http://doi.org/10.1098/rsif.2012.0547

Bowmaker, J. K. (2008). Evolution of vertebrate visual pigments. Vision Research, 48(20), 2022-2041. http://doi.org/10.1016/j.visres.2008.03.025

Brudzynski, S. (2010). Handbook of mammalian vocalization: an integrative neuroscience approach. Academic.

Brudzynski, S. M., & Barnabi, F. (1996). Contribution of the ascending cholinergic pathways in the production of ultrasonic vocalization in the rat. Behavioural Brain Research, 80(1), 145-152. http://doi.org/10.1016/0166-4328 (96)00029-0

Campbell, A. L., Naik, R. R., Sowards, L., & Stone, M. O. (2002). Biological infrared imaging and sensing. Micron (Oxford, England: 1993), 33(2), 211-25. Retrieved from http://www.ncbi.nlm.nih.gov/pubmed/11567889

Carden, S. E., & Hofer, M. A. (1992). Effect of a social companion on the ultrasonic vocalizations and contact responses of 3-day-old rat pups. Behavioral Neuroscience, 106(2), 421-6. Retrieved from http://www.ncbi.nlm.nih.gov/pubmed/1590959

Catarinucci, L., Colella, R., Mainetti, L., Patrono, L., Pieretti, S., Sergi, I., & Tarricone, L. (2014). Smart RFID Antenna System for Indoor Tracking and Behavior Analysis of Small Animals in Colony Cages. IEEE Sensors journal, 14(4), 1198-1206. http://doi.org/10.1109/JSEN.2013.2293594

Crawley, J. N., Szara, S., Pryor, G. T., Creveling, C. R., & Bernard, B. K. (1982). Development and evaluation of a computer-automated color tv tracking system for automatic recording of the social and exploratory behavior of small animals. Journal of Neuroscience Methods, 5(3), 235-247. http://doi.org/10.1016/0165-0270(82)90074-7

Dell'omo, G., Shore, R. F., & Lipp, H. P. (1998). An automated system, based on microchips, for monitoring individual activity in wild small mammals. The journal of Experimental Zoology, 280(1), 97-9. Retrieved from http://www.ncbi.nlm.nih.gov/pubmed/9437856

Deng, Z. D., Carlson, T. J., Li, H., Xiao, J., Myjak, M. J., Lu, J., . . . Eppard, M. B. (2015). An injectable acoustic transmitter for juvenile salmon. Scientific Reports, 5, 8111. http://doi.org/10.1038/srep08111

Deng, Z. D., Weiland, M. A., Fu, T., Seim, T. A., LaMarche, B. L., Choi, E. Y., . . . Eppard, M. B. (2011). A cabled acoustic telemetry system for detecting and tracking juvenile salmon: part 2. Three-dimensional tracking and passage outcomes. Sensors (Basel, Switzerland), 11(6), 5661-76. http://doi.org/10.3390/s110605661

Fukunaga, T., Kubota, S., Oda, S., & Iwasaki, W. (2015). GroupTracker: Video tracking system for multiple animals under severe occlusion. Computational Biology and Chemistry, 57, 39-45. http://doi.org/10.1016/j.compbiolchem.2015.02.006

Ingraham, J. M., Deng, Z. D., Li, X., Fu, T., McMichael, G. A., & Trumbo, B. A. (2014). A fast and accurate decoder for underwater acoustic telemetry. The Review of Scientific Instruments, 85(7), 74903. http://doi.org/10.1063/1.4891041

Kelly, J. B., & Masterton, B. (1977). Auditory sensitivity of the albino rat. Journal of Comparative and Physiological Psychology, 91(4), 930-6. Retrieved from http://www.ncbi.nlm.nih.gov/pubmed/893752

Markweg, E., Nguyen, T. T., Weinberger, S., Ament, C., & Hoffmann, M. (2011). Development of a Miniaturized Multisensory Positioning Device for Laser Dicing Technology. Physics Procedia, 12, 387-395. http://doi.org/10.1016/j.phpro.2011.03.148

Miller, C. T., Mandel, K., & Wang, X. (2010). The communicative content of the common marmoset phee call during antiphonal calling. American Journal of Primatology, 72(11), 974-80. http://doi.org/10.1002/ajp.20854

Ochi, T., Higuchi, Y., & Satta, T. (1994). A three-dimensional positioning system using laser beams and its application to the undulation measurement of a golf course green. In Automation and Robotics in Construction Xi (pp. 319-325). http://doi.org/10.1016/B978-0-444-82044-0.50047-3

Ou-Yang, T.-H., Tsai, M.-L., Yen, C.-T., & Lin, T.-T. (2011). An infrared range camera-based approach for three-dimensional locomotion tracking and pose reconstruction in a rodent. Journal of Neuroscience Methods, 201(1), 116-23. http://doi.org/10.1016/j.jneumeth.2011.07.019

Palczewska, G., Vinberg, F., Stremplewski, P., Bircher, M. P., Salom, D., Komar, K., . . . Palczewski, K. (2014). Human infrared vision is triggered by two-photon chromophore isomerization. Proceedings of the National Academy of Sciences, 111(50), E5445-E5454. http://doi.org/10.1073/pnas.1410162111

Roberts, L. H. (1975). The rodent ultrasound production mechanism. Ultrasonics, 13(2), 83-8. Retrieved from http://www.ncbi.nlm.nih.gov/pubmed/1167711

Steiner, I., Bürgi, C., Werffeli, S., Dell'Omo, G., Valenti, P., Troster, G., . . . Lipp, H. P. (2000). A GPS logger and software for analysis of homing in pigeons and small mammals. Physiology & Behavior, 71(5), 589-96. Retrieved from http://www.ncbi.nlm.nih.gov/pubmed/11239679

Uei-Ming jow, U.-M., Kiani, M., Xueliang Huo, X., & Ghovanloo, M. (2012). Towards a Smart Experimental Arena for Long-Term Electrophysiology Experiments. IEEE Transactions on Biomedical Circuits and Systems, 6(5), 414-423. http://doi.org/10.1109/TBCAS.2012.2211872

Vatine, J. J., Ratner, A., Dvorkin, M., & Seltzer, Z. (1998). A novel computerized system for analyzing motor and social behavior in groups of animals. Journal of Neuroscience Methods, 85(1), 1-11. Retrieved from http://www.ncbi.nlm.nih.gov/pubmed/9874135 von Hünerbein, K., Hamann, H. J., Rüter, E., & Wiltschko, W. (2000). A GPS-based system for recording the flight paths of birds. Die Naturwissenschaften, 87(6), 278-9. Retrieved from http://www.ncbi.nlm.nih.gov/pubmed/10929293

Wang, Z., Mastrogiacomo, L., Franceschini, F., & Maropoulos, P. (2011). Experimental comparison of dynamic tracking performance of iGPS and laser tracker. The International Journal of Advanced Manufacturing Technology, 56(1-4), 205-213. http://doi.org/10.1007/s00170-011-3166-0

Wohr, M., & Schwarting, R. K. W. (2013). Affective communication in rodents: ultrasonic vocalizations as a tool for research on emotion and motivation. Cell and Tissue Research, 354(1), 81-97. http://doi.org/10.1007/s00441-013-1607-9

Yayan, U., Yucel, H., & Yazici, A. (2015). A Low Cost Ultrasonic Based Positioning System for the Indoor Navigation of Mobile Robots. Journal of Intelligent & Robotic Systems, 78(3-4), 541-552. http://doi.org/10.1007/s10846-014-0060-7

AREA OF THE INVENTION

The present invention relates to methods of automatic tracking of laboratory animals for research purposes.

BACKGROUND OF THE INVENTION

Laboratory animals are widely used in scientific studies, and their importance is undoubtedly significant. Typical topics of research include pre-clinical testing of pharmacological substances and investigation of molecular cascades in living organisms via fabrication of genetically modified animals that have an altered expression of the molecules of interest.

Small laboratory animals such as rats or mice play a special role in biological research. The reason for this is not purely economic (i.e., keeping mice is cheaper than keeping larger laboratory animals, such as rats, guinea pigs, cats, dogs and primates), but also has a scientific background: The production of genetically modified mice is faster and easier than that of rats or other larger animals.

Researchers are usually interested in the influence of a particular pharmacological agent or genetic modification on the living organism. The primary indicators of such influence are changes in behavior. These changes are evidence of a biological activity of the substance in question or of the importance of a gene whose expression has been modified. Thus, behavioral testing of animals is an essential part of modern biological research.

To automate behavioral testing, different methods of tracking animal location in experimental environments have been proposed. Commercially available global positioning system (GPS) receivers of small size and weight have allowed tracking of birds and terrestrial animals at a large scale (Steiner et al., 2000; von Hünerbein, Hamann, Rüter, & Wiltschko, 2000). The method is based on estimating the position of a receiver based on the time differences of radio signal arrivals to the receiver from a set of satellites ("time of arrival differences" or TOADs; N≥4 for three-dimensional (3-D) positioning), known locations of the satellites and known speed of the radio waves in the medium. The power consumption of GPS receivers has been reduced significantly during recent years, but it is still too great to allow us to track small animals for long periods of time because GPS batteries are impractical in weight and size for a small animal to carry. Unfortunately, the accuracy of GPS systems is not high enough to provide tracking at a submeter scale. Low accuracy is caused by the very high speed of propagation of radio weaves and, thus, very high requirements for timing accuracy. In addition, under certain conditions, GPS accuracy can be affected by refraction of radio waves from different objects (multipath). Also, GPS transmitting stations that can be arranged in the laboratory environment indoors have substantial cost. In addition, transmitting stations should not interfere with governmental official GPS transmitters, and a compulsory governmental license for such transmitting stations can be difficult to obtain.

Radio frequency identification (RFID) can be used for tracking of laboratory animals at mid-range (approximately several dozens of meters) and small-scale (decimeters) observation arenas (Catarinucci et al., 2014; Dell'omo, Shore, & Lipp, 1998). The RFID-based approach works on the basis of a near-field (NF) RFID multi-antenna system, which operates in low frequency (LF, ~125-128 kHz) or ultra-high frequency (UHF, ~860-960 MHz) bandwidths. Such systems need to be placed below the animals' cage and then are able to identify the NF RFID tags implanted in the laboratory animals or attached to their feet (Catarinucci et al., 2014). When experimental arenas are large (~10-20 m), antennae are usually placed only in the areas of interest (e.g., drinking or feeding places) for economic reasons (Dell'omo et al., 1998). The main disadvantage of this class of system is its low accuracy, as the accuracy of determining the coordinates of the animal approximately matches the antenna size. Thus, an impractically large number of antennae may be needed to cover the area of interest in some cases. Also, an anti-collision protocol, needed to read several tags occurred in one antenna simultaneously, is difficult to realize in an LF system without essential degradation of the scanning rate. For this reason, it is used in UHF installations only (Catarinucci et al., 2014). If only one animal needs to be tracked in the arena, the approach can be greatly simplified because no animal identification is needed. In this case, it is sufficient to attach a small permanent magnet to an animal and detect the appearance of this magnet by an array of magneto-resistive sensors (Uei-Ming Jow, Kiani, Xueliang Huo, & Ghovanloo, 2012). One should note that RFID tracking is applicable only in tracking of animals at the ground surface. Thus, it cannot be applied to birds, bats and fishes.

For decades, video tracking performed with the help of a single video camera has been successfully used for tracking of terrestrial animals (Crawley, Szara, Pryor, Creveling, & Bernard, 1982). However, tracking of species moving in a 3D environment (birds, bats, fishes) require either multiple cameras (Ardekani et al., 2013) or a combination of infrared (IR) projector and IR camera (Ou-Yang, Tsai, Yen, & Lin, 2011). This greatly increases the complexity of the setup. Simultaneous video tracking of several animals in 2D or 3D space poses a particular problem and usually requires the development of sophisticated image recognition algorithms for identification of similar objects (Fukunaga, Kubota, Oda, & Iwasaki, 2015). However, neither of these known methods has 100% reliability, and the percentage of misclassification (mixing of animals) can be relatively large (~8% at each spatial overlap of two animals).

Ultrasonic tracking has been used for accessing trajectories of rats (Vatine, Ratner, Dvorkin, & Seltzer, 1998) and fishes (Ingraham et al., 2014). Vatine et al. attached to a rat a transponder consisting of an ultrasound (40 kHz) emitter and an IR receiver. The total weight of the transponder module was 12.5 g and its size was 20×20×10 mm. The emitter of the transponder sent a short ultrasound packet each time an IR pulse emitted by the stationary station was received. The stationary station received ultrasonic waves generated by the emitter by means of three stationary receivers with known positions. The distance between the emitter and each receiver was computed by the time between acoustic wave propagation from the emitted IR pulse and the arrival of ultrasonic response, knowing the speed of sound in the air. This time is called "time of arrival" (TOA). To estimate sound speed precisely, ambient temperature was measured by the receivers. It was possible to use up to 8 transponders at a time because they emitted different ultrasonic responses. The sampling rate of position measurement can be up to 200 Hz per transponder. Using sound wave phase detection algorithms and under optimal conditions, the resolution of the system can be up to ±0.1 mm. One of the disadvantages of the system is the heavy weight and large size of the transponder module that the animal should carry. Modern advances in microelectronics may help to decrease the weight and size of the transponder, but it is not completely clear to what extent this is possible. Modern ultrasonic transmitters for the aquatic environment (US 2015/0063072 A1) can be extremely small (L=15 mm, D=3.38 mm) and lightweight (0.217 g, including battery), with PZT-5H piezoelectric emitters being as small as 3×3×3 mm and providing sound pressure up to 155-158 dB relative to 1 pPa at 1 m (Z D Deng et al., 2015). However, the smallest commercially available ultrasonic emitters for the air (Murata, MA40H1S-R) are much larger (5.2×5.2×1.15 mm). In spite of their comparatively large size, they generate much weaker sound pressure, only up to 105 dB relative to 1 µPa at 1 m. Note that the threshold of hearing for humans is assumed to be 20 µPa. The loudness of the Murata air transducer computed from this more common reference level is 79 dB. The primary reason for the difference in loudness is the different physical properties of water and air. In particular, the low compressibility of water helps to decrease the size of ultrasonic transducers for this medium. The larger transducer for air will inherently have larger mechanical losses that will require stronger and heavier power sources (battery).

The above-mentioned IR synchronization was not used in fish tracking (Ingraham et al., 2014). Instead, multiple mobile ultrasonic transmitters were used to emit short ultrasonic packets asynchronously clocked by their internal timers. However, because the tracking was done on a larger spatial scale and with relatively low spatial accuracy, it was possible to send ultrasonic packets less frequently, typically every 3 seconds. As the frequency of the ultrasound was high (416.7 kHz), it was possible to use very short packets (744 µS). Thus, the probability of simultaneous arrival of packets from a pair of fishes (overlapping) was small even in the case of a large number of fishes being in the perception range of the recording system. A set of hydrophones with known locations was used to detect acoustic signals from the transmitters. When more than four hydrophones detected the same transmitter message, the four with the optimum geometric configuration for 3D tracking were selected to measure three TOADs to obtain the 3D coordinate of the transmitter. One of the disadvantages of this approach, when it is applied for tracking of several animals in the air and on a small spatial scale, is the much higher probability of collision of signals from different transmitters and the data loss thereof. The typical frequency of ultrasonic positioning systems working in the air is 40 kHz (i.e., approximately 10 times lower than in water). For this reason, the transmission of the same message with other conditions equal will take 10 times longer. Also, animals at small spatial scales should be tracked at much higher rates, say 10 Hz (instead of 0.33 Hz in the water). Thus, with an equal number of animals, the probability of signal collision and data loss in the aerial system will be 300 times higher than that in the water. Suppose that we have N=16 animals tracked at rate F=10 Hz. One can easily get that, if the duration of the ultrasonic packet is $\tau$=0.00744 s, the probability of receiving a signal without an overlap will be $P=(1-\tau \cdot F)^{N-1}=0.3156$. This means that about 69% of attempts to get the coordinate of the transmitter will fail because of collisions. Thus, the average scanning rate will be only 3.156 Hz, which is too low for tracking fast animals, such as birds or mice. One can try to diminish the length of the data packet from 31 bits to a minimal 5 bits by decreasing the header length from 7 bits to a minimal 1 bit, by leaving only 4 data bits instead of 16 to code 16 different animals and by omitting the 8-bit cyclical redundancy check (CRC) at the end. In this case, the probability of collision-free reception will be 0.8352 (i.e., about 16.5% loss), but the absence of the packet integrity check (by CRC) will lead to large number of false-positive detections. Also, the absence of a reliably detectable header will greatly increase the computational work of processing false-detected messages. The increase in ultrasound frequency might help to increase the data rate and, thus, to decrease the collision probability. However, this alternative is blocked by the absence of small high-frequency air ultrasonic emitters, especially with an anisotropic emission.

Although tracking of human-made vehicles (robots) is out of the scope of the current invention, some ideas from this field can be adopted for the purpose of animal tracking. In U.S. Pat. No. 7,406,000 (September 2006), a positioning system using ultrasonic waves was proposed. In this system, the ultrasonic waves are emitted by a set of fixed emitters that are activated sequentially in a known fixed sequence. In addition, an IR synchronizing signal is emitted by the stationary system synchronously with the first ultrasonic signal. A mobile device, whose position should be determined, receives ultrasonic waves and IR synchronizing signal. In the first step, times of arrivals (TOAs) are determined from the times of reception of the ultrasonic signals and the synchronizing signal, taking into account the known time intervals between emissions of ultrasonic signals. In the second step, the position of the mobile device is calculated from the known positions of the emitters. In the publication (Yayan, Yucel, & Yazici, 2015), a similar approach was used, in which the ultrasonic receiver is with the mobile unit whose position has to be determined. However, no IR synchronizing signal is used, and the position is calculated from the TOADs from at least four fixed transmitters with known locations. However, application of these ideas to animal tracking needs additional elaboration. The main problem is that, contrary to robots, most animals are not quiet, but emit sounds with a wide power spectrum and high loudness. For example, the classic laboratory songbird, the zebra finch, produces vocalizations with a spectrum of up to 10 kHz and a loudness of up to 100 dB (measured near its back). The smallest monkey, the marmoset, also widely used in animal research, can emit calls with a loudness of up to 120 dB and the frequency of the first harmonic up to 11 kHz, but a strong second harmonic of up to 22 kHz (Miller, Mandel, & Wang, 2010). Laboratory rodents, such as mice and rats, can vocalize and hear in the ultrasonic frequency range (Wohr & Schwarting, 2013). For example, laboratory rats can hear frequencies of up to 80 kHz (Kelly & Masterton, 1977). Adult rats can produce sounds with frequencies of up to 20-30 kHz (S. M. Brudzynski & Barnabi, 1996) and infant rats of up to 30-50 kHz (Carden & Hofer, 1992). The loudness of rodent calls can be up to 100 dB at a 10-cm distance (Roberts, 1975). Some rodents can vocalize and hear at frequencies of up to 160 kHz (S. Brudzynski, 2010). Thus, to avoid interference with native ultrasonic communication, the ultrasonic tracking system should use frequencies above the animal's hearing range. However, this is not the only requirement of such a system. The second requirement is that natural vocalizations (including ultrasonic) and other types of acoustic noises produced by the animals should not affect the performance of the tracking system. This requirement is not very easy to fulfill because the loudness of commercially available ultrasonic emitters lies around 100 dB (at a 1-m distance) and approximately matches the loudness of animal vocalization (see above). However, if a microphone is placed at the animal's back (e.g., 2 cm from the head) and the ultrasonic transmitters that are sending signals to the same receiver are at distances of about 2 m from the animal, the amplitude of the sound from the animal will be 100× larger than that from the stationary transmitters (a difference of 40 dB). For reliable detection of ultrasonic packets, it would be optimal to have the signal to noise ratio (SNR) in the audio channel at around 100 (40 dB) or above. Thus, the desired total suppression of local noises should be around 80 dB. If an animal vocalizes at 10 kHz and the ultrasonic tracking system works at 40 kHz, such attenuation should be achieved in a very narrow frequency range of 10-40 kHz. Good separation of ultrasonic tracking signals from animal vocalizations and noises is an aspect of the current invention.

Progress in laser technology has led to the development of a set of position measurement systems. The first use of lasers for position measurement in industry was based on measurement of light propagation time from the light source to the reflector and back, such as in a laser rangefinder (see, e.g., U.S. Pat. No. 5,467,273, November 1995). The time delay was measured by very accurate sub-nanosecond timing circuitry or by an interferometer. In spite of the latest progress in miniaturization (Markweg, Nguyen, Weinberger, Ament, & Hoffmann, 2011), such an approach cannot be used for animal tracking because of size, weight and financial constraints.

The second, much more economical, approach is based on measurement of time delays between flashes produced by rotating laser sources with known angular velocity that are placed at known positions (Ochi, Higuchi, & Satta, 1994). The 3D positioning system described by Ochi and colleagues (Ochi et al., 1994) was designed for measuring the undulation of a golf course green. The system consists of two laser beacons set at two reference positions and a photo sensor fixed to the mobile object to be positioned. Each of the laser beacons emits two laser beams that rotate horizontally (in clockwise and counterclockwise directions). The photo sensor is vertically long (i.e. consists from a linear array of photodiodes or phototransistors) and can detect these laser beams. The mobile robot measures its angular position relative to a laser beacon's known reference direction (in which two beams coincide) via the time intervals between detections of two laser beams. From these two angles and the known locations of laser-emitting stations, the position of the robot in the horizontal plane can be computed. The vertical coordinate of the robot is obtained from the position of an incident beam on the photo sensor.

The idea of computing the position of a rotating light emitter relative to a light receiver (or to a light retroreflective element) using time intervals between flashes has been developed further in U.S. Pat. No. 4,796,198 (June 1989); U.S. Pat. No. 4,830,489 (May 1989); U.S. Pat. No. 5,100,229 (March 1992); U.S. Pat. No. 5,110,202 (May 1992); U.S. Pat. No. 5,247,487 (September 1993); U.S. Pat. No. 5,729,475 (March 1998); U.S. Pat. No. 5,884,239 (March 1999); U.S. Pat. No. 6,198,528 (March 2001); U.S. Pat. No. 6,452,668 (September 2002); and U.S. Pat. No. 6,535,282 (March 2003) and European Pat. No. 1,166,042 (March 2007). Comparative analysis of the rotating light beam tracker and the reference laser tracking system shows acceptable accuracy of the former and its suitability for many applications (Wang, Mastrogiacomo, Franceschini, & Maropoulos, 2011). However, application of the rotating laser beam tracker concept to animal tracking should satisfy additional requirements. First, the mobile part of the system should be sufficiently small and lightweight to be transportable by typical laboratory animals such as mice (body weight ~25 g) or zebra finches (small songbird with body weight ~14 g). To avoid unwanted influence of the device to the animal, the weight of the movable equipment should not exceed 1 g. Second, the emitted light should not affect normal behavior of the animal. This requirement is new: It is not applicable to robots or to humans in virtual reality systems as their eyes are covered by virtual reality googles that obscure perception of external light. Even if the exploited light wavelength is invisible to humans (i.e., it lies in the ultraviolet or IR ranges), it may be visible to animals because the light sensitivity of many species exceeds the spectral range of light visible to humans. If the human eye can see light with a wavelength of 390-700 nm, birds can perceive ultraviolet light and their visible range is about 365-570 nm. A similar shift in spectral sensitivity to ultraviolet has been observed in some mammals (Bowmaker, 2008). Many animals can sense IR illumination (Campbell, Naik, Sowards, & Stone, 2002). A variety of thermoreceptors are present in animals and insects, which aid them in hunting, feeding and survival. IR imaging pit organs in Crotaline and Boid snakes enable them to detect, locate and apprehend their prey via the IR radiation prey emits. IR pit organs of common vampire bats (*Desmodusrotundus*) enable them to detect IR radiation emitted by blood-rich locations on homeothermic prey. The beetle *Melanophilaacuminata* locates forest fires via IR-detecting pit organs in order to lay its eggs in freshly dead conifers. Thermoreceptors located in the wings and antennae of darkly pigmented butterflies (*Pachlioptaaristolochiae* and *Troidesrhadamathusplateni*) protect them from heat damage while sun basking. Blood-sucking bugs (*Triatomainfestans*) are speculated to possess thermoreceptors, which enable them to perceive the radiant heat emitted by homeothermic prey and estimate temperature at a distance (Campbell et al., 2002). Known IR light-based tracking systems cannot be used for tracking of these animals. Nevertheless, in the current invention, principles of these systems are exploited for tracking even these animals.

When the sensitivity of different animals to light is discussed, the ordinary light intensities observed in nature are usually assumed. However, sensitivity to light of particular wavelengths also depends on light intensity. Humans, and likely most animals, can see IR light if it is strong enough (Palczewska et al., 2014). This factor also should be taken into account in the design of light-based animal tracking systems, including the system described in the current invention.

BRIEF SUMMARY OF THE INVENTION

The first embodiment of the present method of determining the position of an animal includes placing several stationary ultrasonic emitters in the area where the animal should be tracked and attaching a transportable mobile device to the animal. The mobile device incorporates an ultrasonic receiver and an analog radio transmitter. Locations of the emitters are fixed and known. For example, if the animal should be tracked in a chamber measuring 1×1×1 m, four emitters can be installed near the corners of this cube. In this case, the maximal sound propagation time T from an emitter to a receiver will be $T=\sqrt{3}/v=5.05$ ms (for the speed of sound in the air, $v=343$ m/s). All emitters are connected to a controlling module that periodically activates the emitters in a known fixed sequence. With each activation, the emitter generates a short 0.2 ms, 250 kHz ultrasonic pulse. Emitters can be activated in a sequence from the first to the fourth emitter with a time span of 6 ms between activations. Thus, with any position of the receiver in the space, signals from different emitters will never overlap (5.25<6.00 ms). The sequence of these activations with the duration 6·3+ 0.2=18.2 ms can be repeated with a period of 33.3 ms to get a tracking sampling rate of 30 Hz, sufficient for most tracking tasks. The receiver contains a wide-band microphone capable of perceiving the ultrasonic 250 kHz signal in addition to the ordinary audio band of 20 Hz to 20 kHz. The signal from the microphone is directed to an amplifier that amplifies the ultrasonic frequency band 100× times more than the audio band of animal vocalization. Thus, if the ultrasonic emitter and the animal have equal loudness, and the distance from the receiver to the transmitter is 100× larger than the distance from the transmitter to the animal's head, the ultrasonic signal and the vocalization signal will have similar amplitudes at the output of this selective amplifier. The signal of the amplifier is directed to the analog radio transmitter. The radio transmitter transmits the signal to the connected computer receiver. The receiver digitizes the signal for further storage in the computer. The stored signal carries information about the animal's location (coded in the TOADs of ultrasonic signals) and, additionally, animal vocalizations. The stored wide-band signal is passed through a digital filter to separate ultrasonic signal from the rest—the animal vocalizations and noise. If animal vocalizations are of interest, the wide-band signal is passed also through a specially constructed digital filter to separate animal vocalizations to be used in further behavioral analysis. The main advantage of this embodiment is the simplicity of realization of the mobile receiver. It can be made extremely light (<1 g) and can have very small power consumption (<0.5 mA). Thus, it can be used with a small bird such as the zebra finch. The second advantage of this construction is that, in addition to the main function of recording animal coordinates, the system will be able to record ecologically important signals, such as animal vocalization. The realization of this additional function will require a very small number of additional components. This embodiment also allows us to track several animals simultaneously. To achieve this, different analog radio transmitters should have different carrier frequencies. Modern software-defined radios (SDRs) are capable of receiving signals from several transmitters simultaneously. Using such receivers will decrease the total cost of the receiving part compared to a solution in which each transmitter has its own receiver adjusted to its frequency.

The second embodiment of the present method of animal position detection includes, as in the first embodiment, placing several stationary ultrasonic emitters in the area where the animal should be tracked and attaching a transportable mobile device to the animal. The mobile device incorporates an ultrasonic receiver and a large on-board memory for data collection. In addition, an IR emitter is placed stationary in the recording chamber. The emitter transmits a synchronizing IR signal to the transportable mobile device equipped with an IR sensor and attached to the animal. When an optical synchronizing signal that propagates essentially without delay is used, the number of ultrasonic emitters necessary for 3D tracking can be decreased to three and the TOA of ultrasonic signals can be computed in a simpler way. The mobile device has analog filters for separating ultrasonic tracking signals from animal vocalizations and an analog digital converter (ADC) for conversion of these signals to digital form. In addition, the mobile device can be equipped with a 3D accelerometer, a 3D gyroscope and a 3D magnetic compass to track orientation of the animal body in the space and to provide high sampling rate tracking of animal coordinates. All sensors are controlled by the on-board microcontroller unit (MCU), which stores the above-mentioned information in a large on-board memory. After the end of the recording session, the logging unit can be detached from the animal for data downloading. The main advantage of this embodiment is that, in addition to the 3D spatial coordinates and vocalizations of the animal, the system can acquire additional information such as orientation of the animal's body. Additional information is not limited to animal body orientation, however, and can include information from different converters of biological signals, including converters receiving electrical activity from the brain to correlate brain activity with animal behavior. The electrical activity can include electroencephalogram (EEG), local field potentials (LFPs) and activity of isolated neuronal cells. In this embodiment, the ultrasonic tracking can be combined with the recording of biological data by a logger described in U.S. Pat. No. 8,160,688 (Apr. 2012). An additional advantage of this recording system is natively achieved precise synchronization of the behavioral and neurophysiological data. Such synchronization avoids the additional step of synchronization of data from different sources, thus simplifying the data analysis.

Both systems described above have in their basis a physical principle of converting distance to a time interval. The moderate value of the speed of sound in air makes conversion of distance to time achievable with economical, commonly available electronic components. However, the intensity of sound attenuates rapidly with distance, making such tracking impractical at large spatial scales. Also, increased distance between an emitter and a receiver can lead to a decreased sampling rate in some configurations because of the necessity of resolving the problem of temporal overlapping of ultrasonic signals sequentially emitted from several locations.

These disadvantages are eliminated in the next embodiment of the current invention: an optical tracking system in which a narrow planar light beam moves through the animal position measurement field and illuminates the light sensor of the mobile receiver when beam and receiver intersect. The scanning planar light beam can be produced by a rotating mirror or a prism. The relative direction from transmitter to receiver is determined by the time at which the receiver detects the light beam (i.e., by the time when the light beam intersects with the receiver). To simplify computation of the intersection angle, a strobe pulse illuminates the whole area at a particular phase of the light beam rotation. One rotating planar beam is sufficient to determine a position in a single-dimension space (e.g., to get the position of a beetle on a straight runway). However, to get a position in a two-dimensional space by this principle (e.g., to get the position of a mouse in an open arena), one will need two planar beams moving in non-coinciding (e.g., orthogonal) directions. The axes of rotation should be elevated over the surface where the animal is moving. To track a bird in a 3D space using the same idea, one would need at least three such planar light beams, and, in addition, the axis of rotation of at least one of them should not have a common intersection point with the rotation axes of the two other planar light beams. To satisfy this last geometrical requirement, the emitter of at least one planar light beam should be spatially separated from the other two emitters. This makes the 3D tracking system with scanning light beams more complicated and inconvenient in some environments.

The last embodiment of the current invention eliminates the necessity of having several distributed modules for 3D tracking. It represents a hybrid system combining the pluses of both ultrasonic and optical beam tracking methods. In this embodiment, two optical transmitters are mounted over an arena in which an animal has to be tracked. These two optical transmitters are sufficient for tracking an animal in a horizontal 2D plane. To get the third coordinate (i.e., an altitude), an ultrasonic emitter is placed in the vicinity of two scanning light emitters. Thus, the altitude of the mobile device is measured by the propagation time of the ultrasonic signal from the emitter to the mobile receiver. This allows a complete 3D tracking system packed in a small module that can be placed in practically any environment. Of course, to increase the reliability of tracking in an environment with obstacles, one can place several such 3D tracking stationary modules in different places within the animal position measurement field.

BRIEF DESCRIPTION OF THE DRAWINGS

FIG. 13A shows an example of frequently used rectangular envelope of ultrasonic signal.

FIG. 13B shows a non-modulated ultrasonic signal, i.e. the signal with the rectangular envelope presented in FIG. 13A.

FIG. 13C shows the power spectrum of the ultrasonic signal shown in FIG. 13B. This power spectrum essentially propagates into the frequency range of animal hearing.

FIG. 13D shows an ultrasonic signal envelope with limited first derivative in accordance with the current invention.

FIG. 13E shows an ultrasonic signal modulated by the envelope shown in FIG. 13D.

FIG. 13F shows the power spectrum of the ultrasonic signal shown in FIG. 13E. Note highly diminished propagation of the spectral power into the low frequencies compared to FIG. 13C.

FIG. 13G shows an ultrasonic signal envelope with limited second derivative in accordance with another embodiment of the current invention.

FIG. 13H shows an ultrasonic signal modulated by the envelope shown in FIG. 13G.

FIG. 13I shows the power spectrum of the ultrasonic signal shown in FIG. 13H.

Note that the attenuation of power spectrum in this figure is similar to FIG. 13F for frequencies of animal hearing (below 10 kHz). Such ultrasonic signals are usually produced by wide-band ultrasonic emitters with negligible self-oscillatory properties. In such emitters, ultrasonic output is directly proportional to the energizing signal but is slightly delayed relative to it.

Figure 14A:
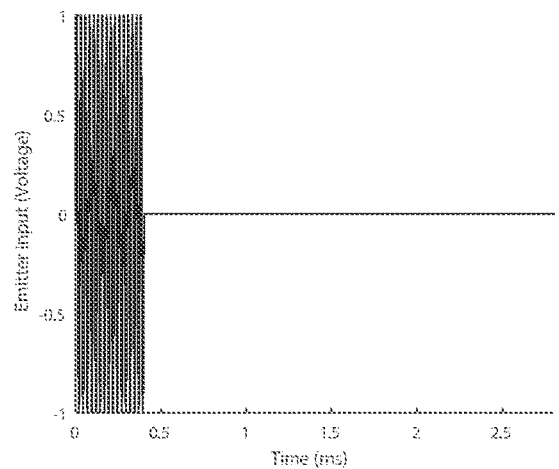

FIG. 14A shows an example of frequently used non-modulated burst for energizing of an ultrasonic emitter. This burst is identical to the one shown in FIG. 13B.

Figure 14B:
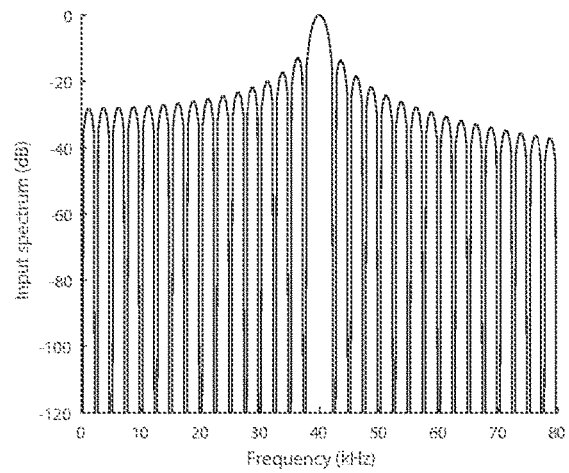

FIG. 14B shows the power spectrum of the energizing burst presented in FIG. 14A. It is identical to the spectrum shown in FIG. 13C. FIGS. 14A and 14B are given to simplify a comparison of the signals in these figures with the signals in the following FIGS. 14C and 14D.

Figure 14C:
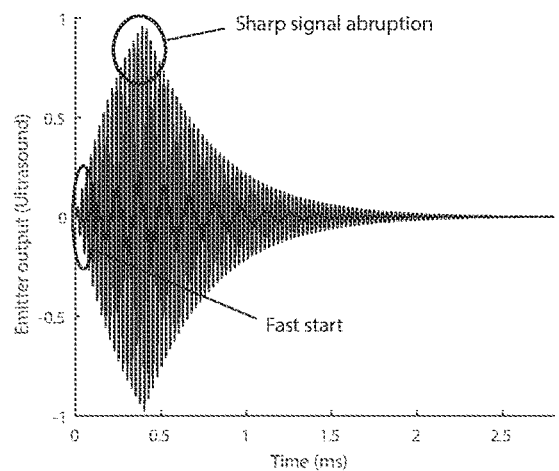

FIG. 14C shows the ultrasonic output of the ultrasonic emitter with significant self-oscillatory properties (Q factor 50).

Figure 14D:
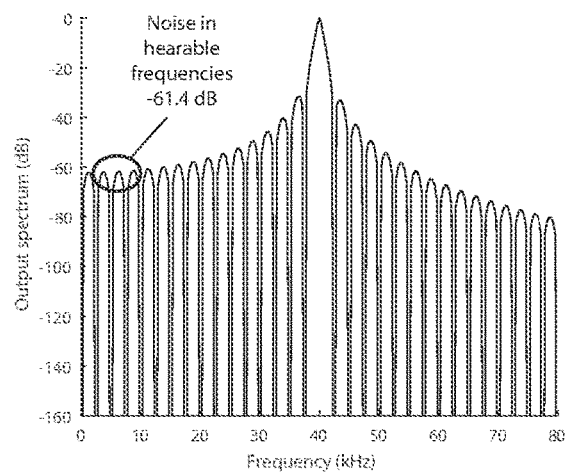

FIG. 14D shows the power spectrum of the ultrasonic signal presented in FIG. 14C. Note that even if the physical oscillatory properties of the sound-emitting element are decreasing the spectral power in the low frequencies of the ultrasonic signal output, the propagation of the spectral power into the frequency range of animal hearing (<10 kHz) is still essential.

Figure 15A:
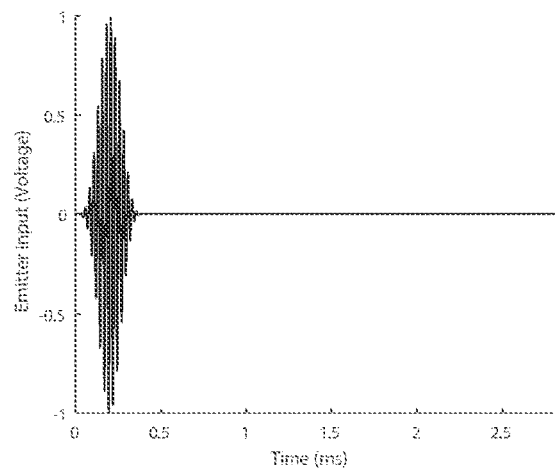

FIG. 15A shows the animal-friendly modulated burst for energizing an ultrasonic emitter proposed in the current invention.

Figure 15B:
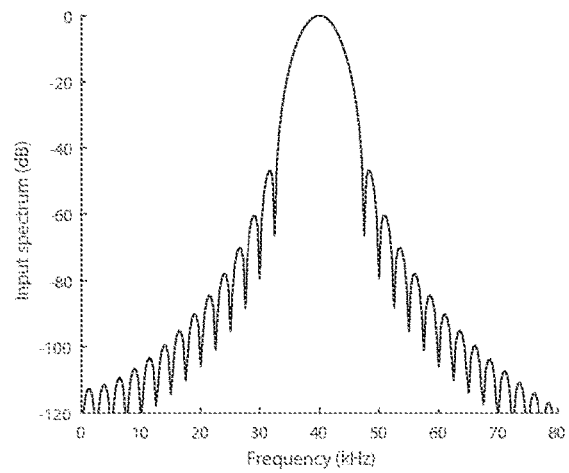

FIG. 15B shows the power spectrum of the animal-friendly modulated energizing burst presented in FIG. 15A.

Figure 15C:
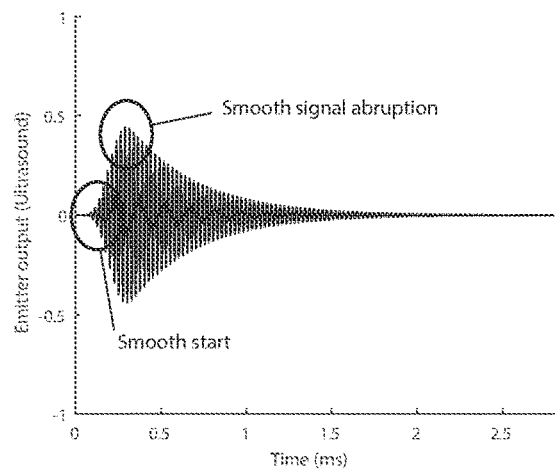

FIG. 15C shows the ultrasonic output of the ultrasonic emitter with significant self-oscillatory properties (Q factor 50) energized by the animal-friendly modulated burst presented in FIG. 15A.

Figure 15D:
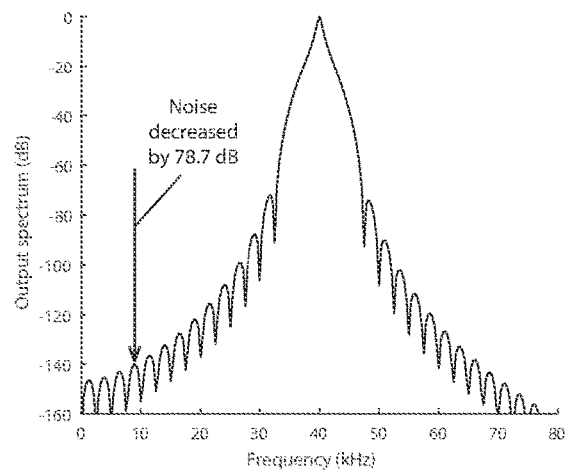

FIG. 15D shows the power spectrum of the ultrasonic signal presented in FIG. 15C. The power of this signal is strongly attenuated in the frequency band of animal hearing and it does not disturb the animal.

Figure 16A:
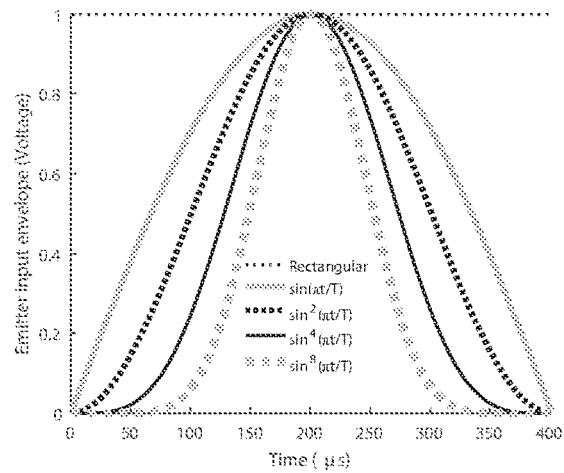

FIG. 16A shows the envelopes of the electrical signals energizing the ultrasonic emitter proposed in the current invention.

Figure 16B:
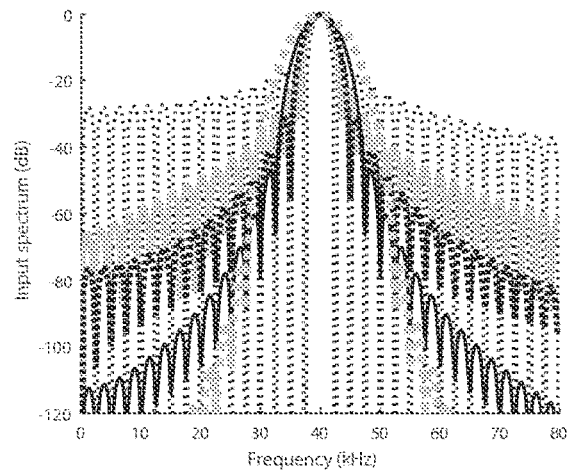

FIG. 16B shows the power spectrums of the electrical signals with the envelopes shown in FIG. 16A.

Figure 16C:
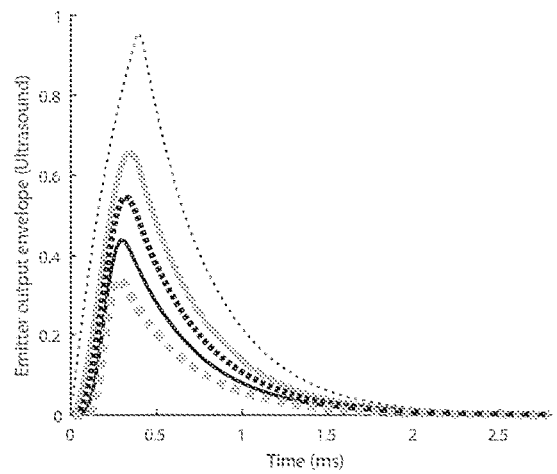

FIG. 16C shows the envelopes of the output ultrasonic signals produced by the emitter with self-oscillatory properties (Q=50) energized by the electrical signals with the envelopes presented in FIG. 16A.

Figure 16D:
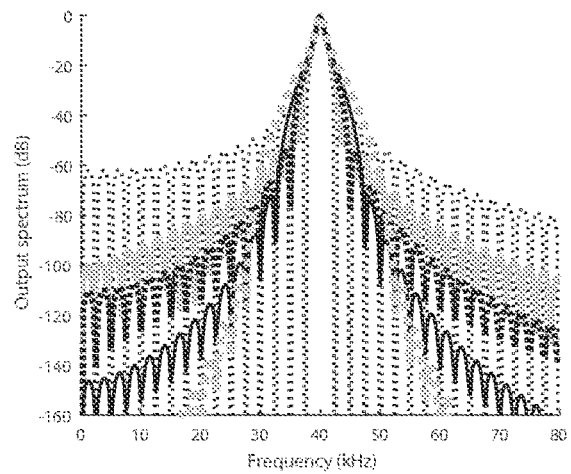

FIG. 16D shows the power spectrums of the ultrasonic signals presented in FIG. 16C. Note a very significant attenuation of the signal power in low frequencies with an increase of power of the sinusoidal function.

Figure 17:
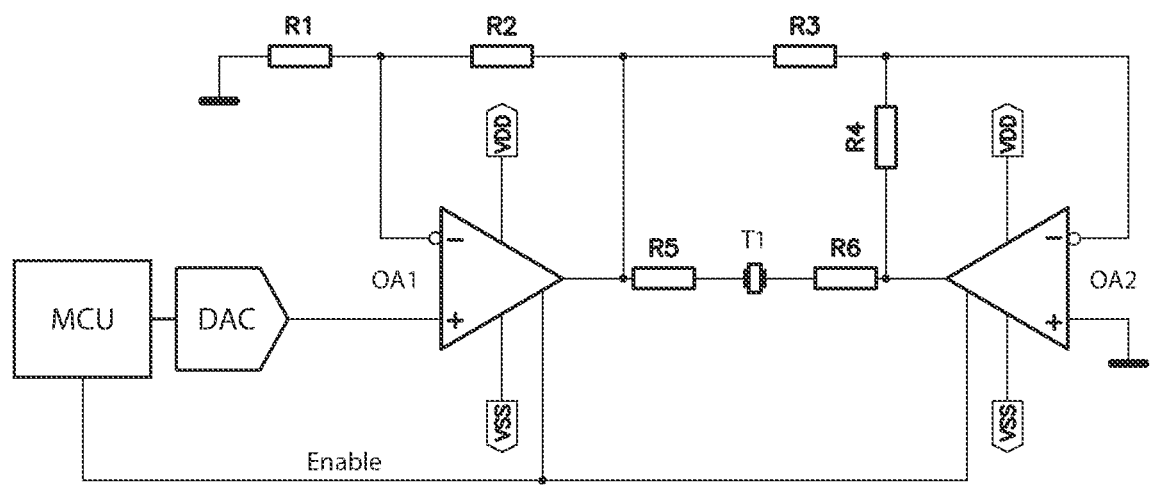

FIG. 17 is a circuit diagram of an ultrasonic driver on DAC and two bridged amplifiers to generate animal-friendly ultrasonic positioning bursts depicted in FIG. 15.

Figure 18A:
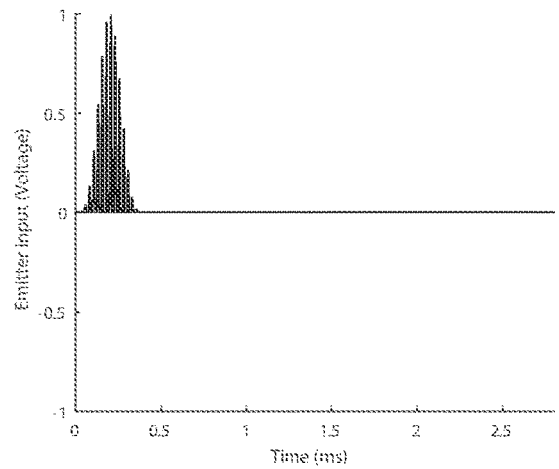

FIG. 18A shows an asymmetric (consisting of half-sine waves) burst for energizing of an ultrasonic emitter.

Figure 18B:
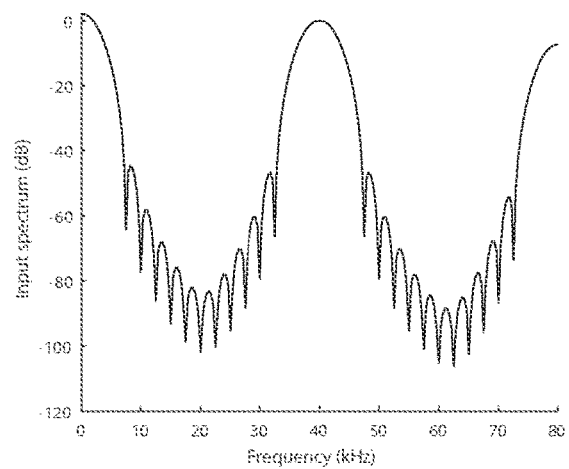

FIG. 18B shows the power spectrum of the asymmetric energizing burst presented in FIG. 18A.

Figure 18C:
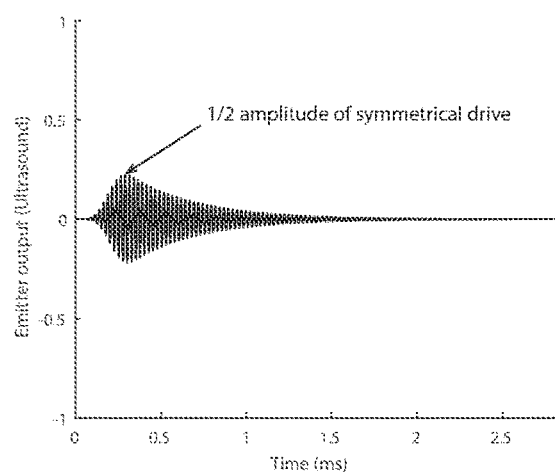

FIG. 18C shows the ultrasonic output of the ultrasonic emitter with significant self-oscillatory properties (Q factor 50) energized by the asymmetric modulated burst presented in FIG. 18A.

Figure 18D:
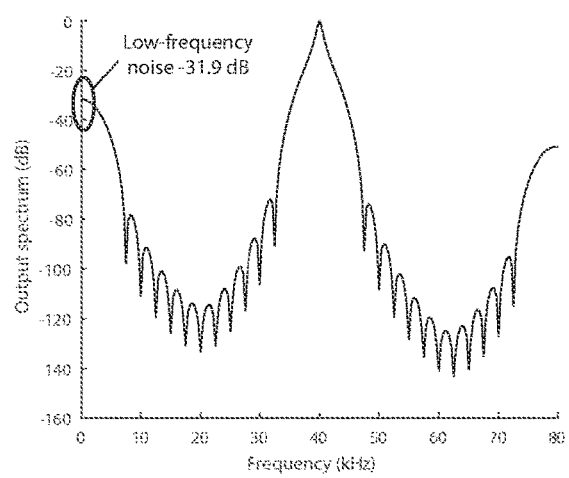

FIG. 18D shows the power spectrum of the ultrasonic signal presented in FIG. 18C. Asymmetry in the input generates asymmetry in the output. Although the asymmetry in the output is highly attenuated, the asymmetric drive can be used only in conditions of strong background noise that should mask all disturbances from the ultrasonic tracking system.

Figure 19:
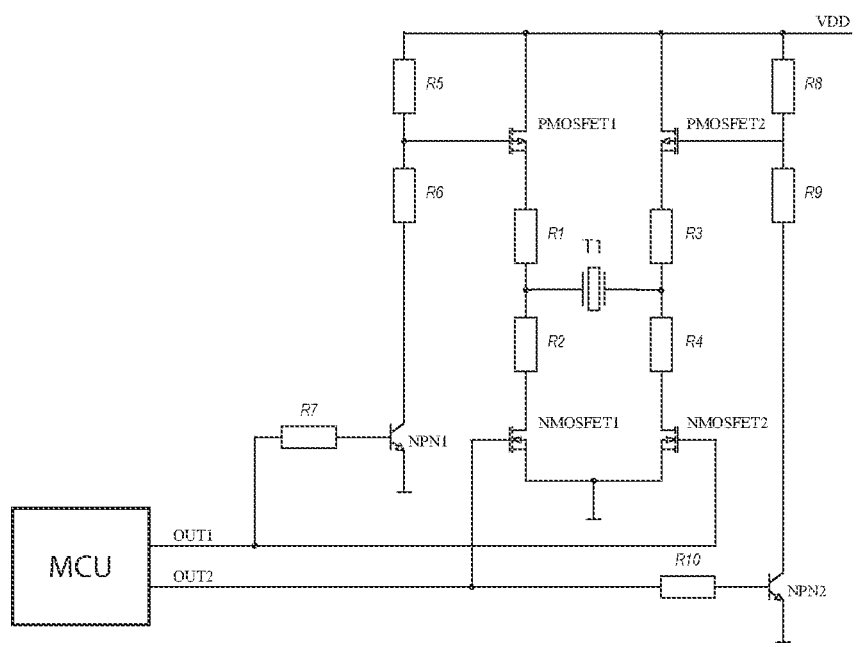
Figure 20:
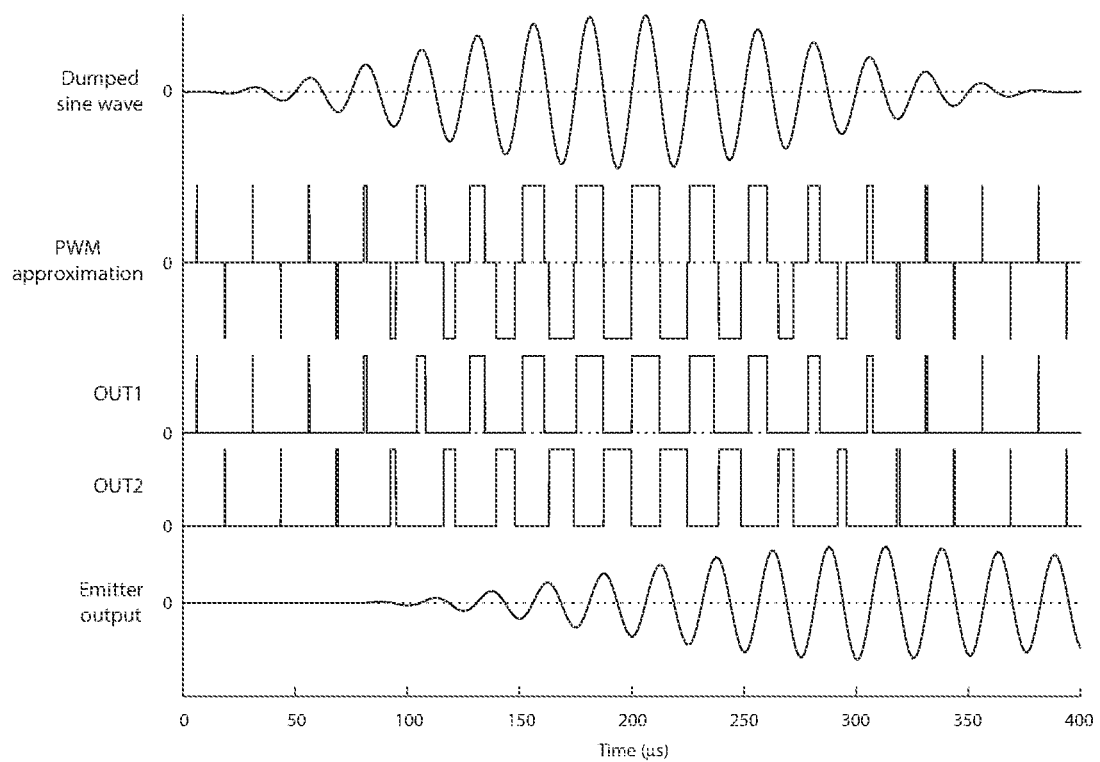

FIG. 19 is a circuit diagram of a high-voltage ultrasonic driver for biphasic pulse-width-modulated (PWM) generation of the ultrasonic signal shown in FIGS. 20, 21.

FIG. 20 shows from top to bottom: a temporal diagram of a dumped sine wave used for low-noise, animal-friendly energizing of an ultrasonic emitter; an alternative PWM approximation of this signal for energy-preserving energizing; and two outputs of the microcontroller used to get a symmetric PWM energizing of the emitter by circuitry in FIG. 19; and the output of the emitter with self-oscillatory properties with Q=50.

Figure 21A:
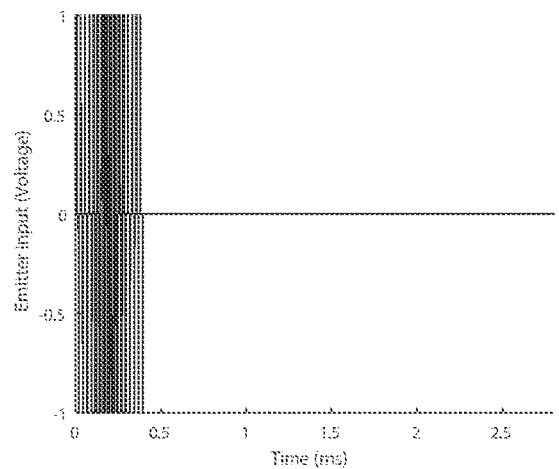

FIG. 21A shows PWM-modulated electrical signal energizing the ultrasonic emitter proposed in the current invention.

Figure 21B:
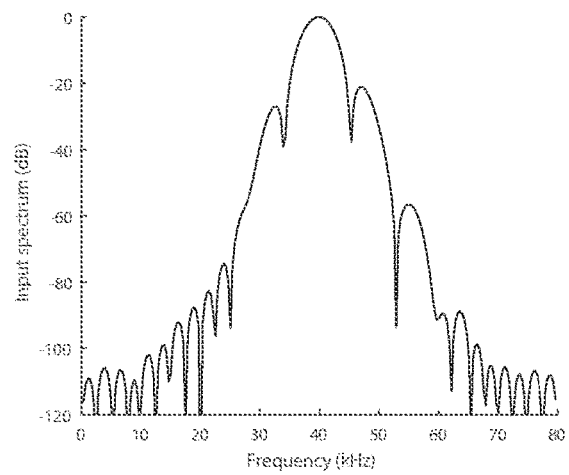

FIG. 21B shows the power spectrum of the PWM-modulated electrical signal presented in FIG. 21A.

Figure 21C:
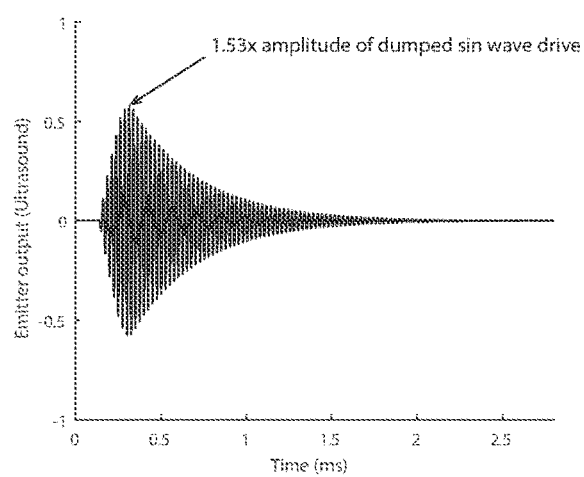

FIG. 21C shows the ultrasonic output of the ultrasonic emitter with significant self-oscillatory properties (Q factor 50) energized by the PWM-modulated electrical signal presented in FIG. 21A.

Figure 21D:
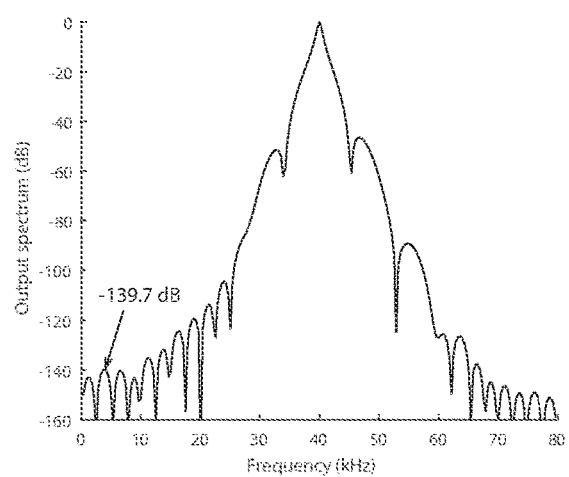

FIG. 21D shows the power spectrum of the ultrasonic signal presented in FIG. 21C. Note that the power spectra FIGS. 21B and 21D are very similar to the corresponding power spectra in FIGS. 15B and 15D, but the amplitude of ultrasonic signal is increased 1.53× relative to the output of the dumped sine wave drive.

Figure 22:
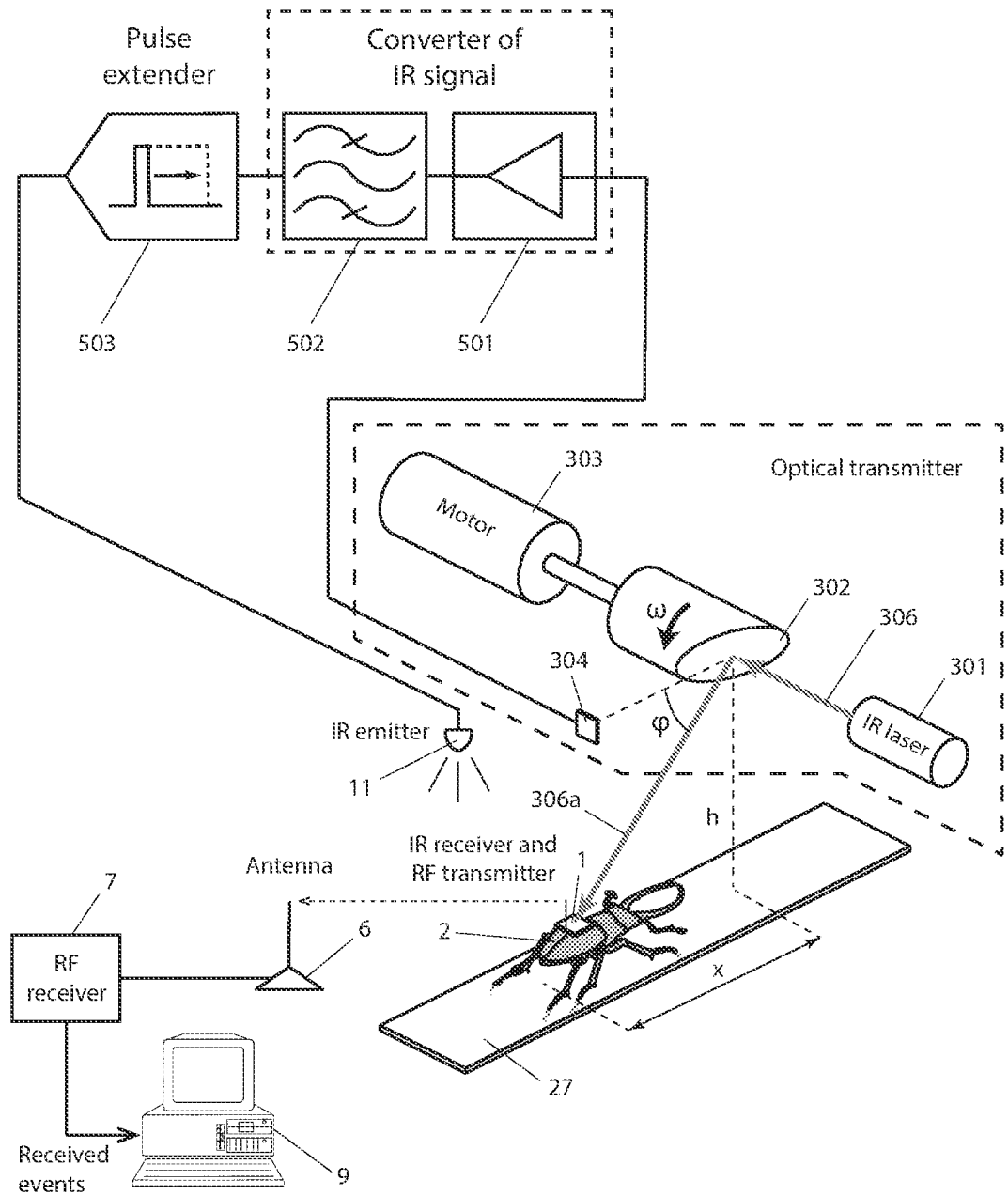

FIG. 22 illustrates the basic principle of optical animal tracking proposed in the current invention for single-dimensional tracking of a beetle on a runway with the help of a rotating anisotropic planar light beam.

Figure 23:
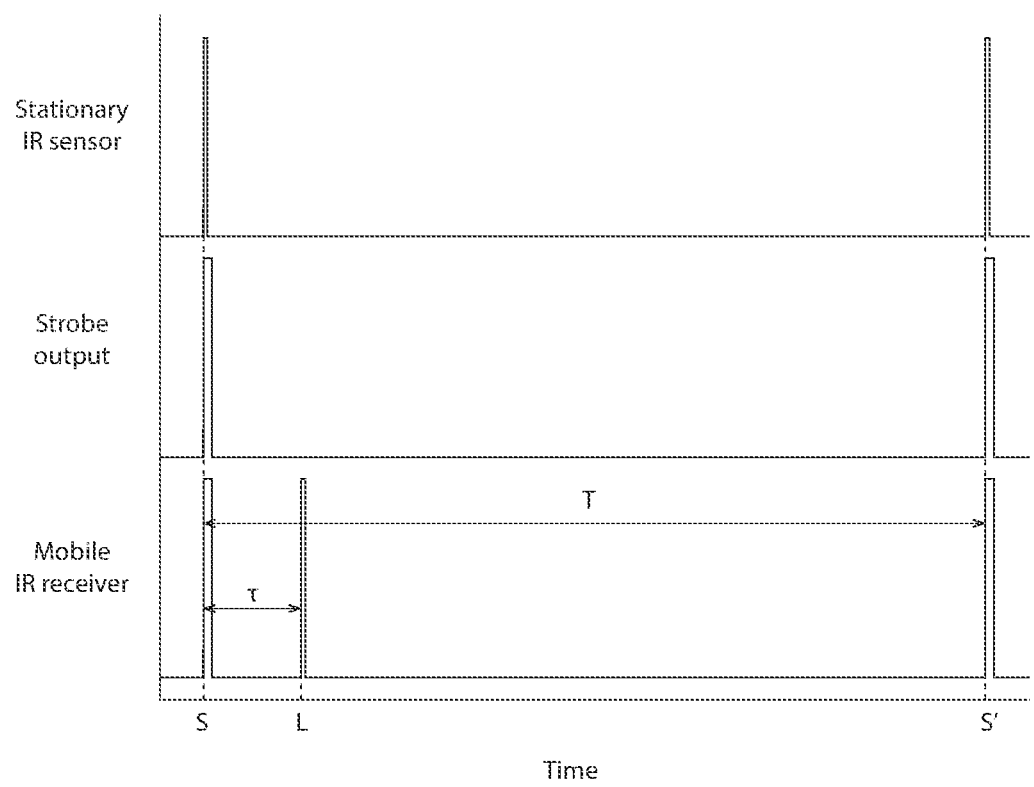

FIG. 23 shows the schematic temporal diagram of optical signals in the system of FIG. 22.

Figure 24:
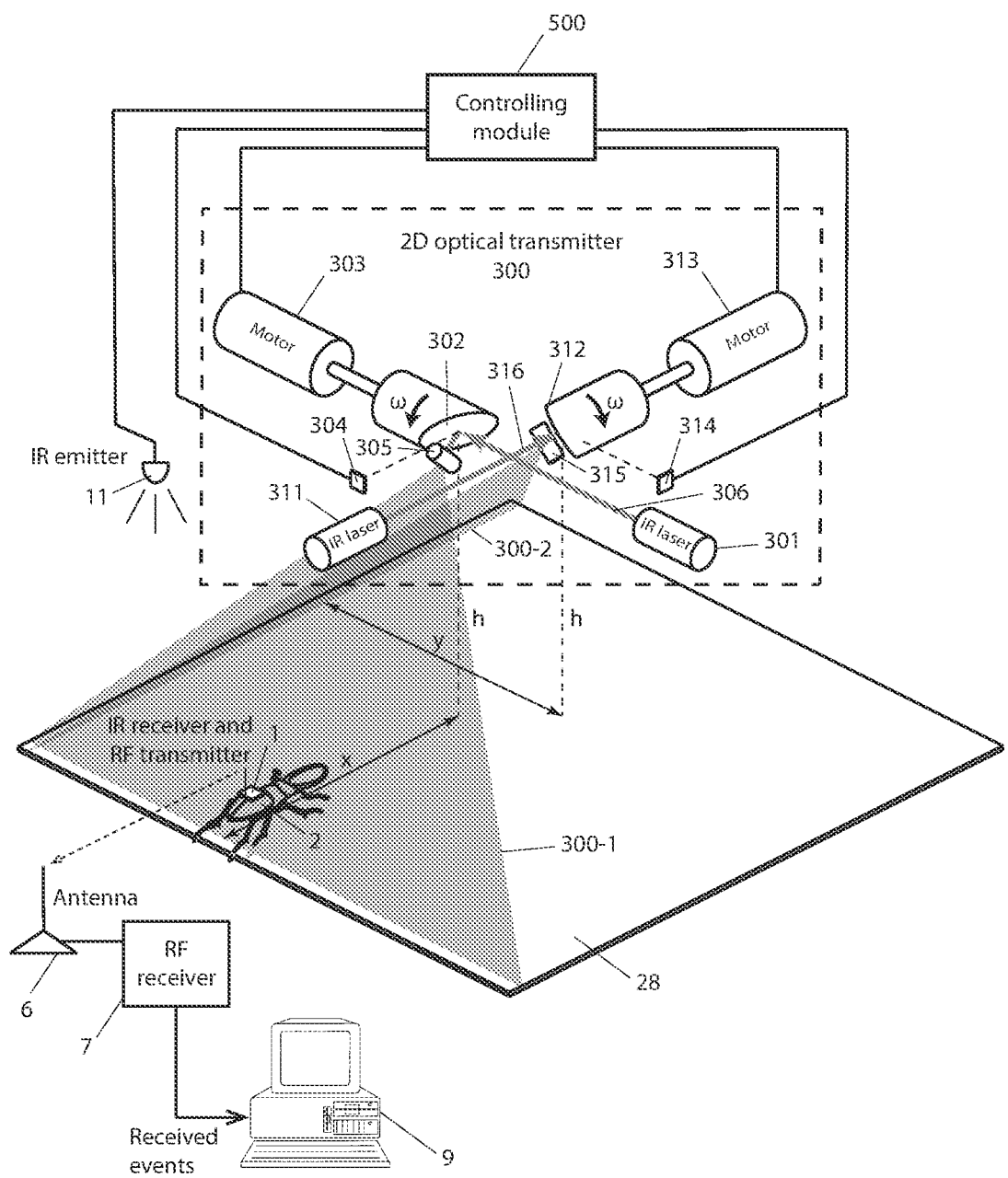

FIG. 24 depicts the realization of the optical system proposed in the current invention for two-dimensional tracking of a beetle on a flat surface. Two rotating anisotropic light beams are needed in this case.

Figure 25:
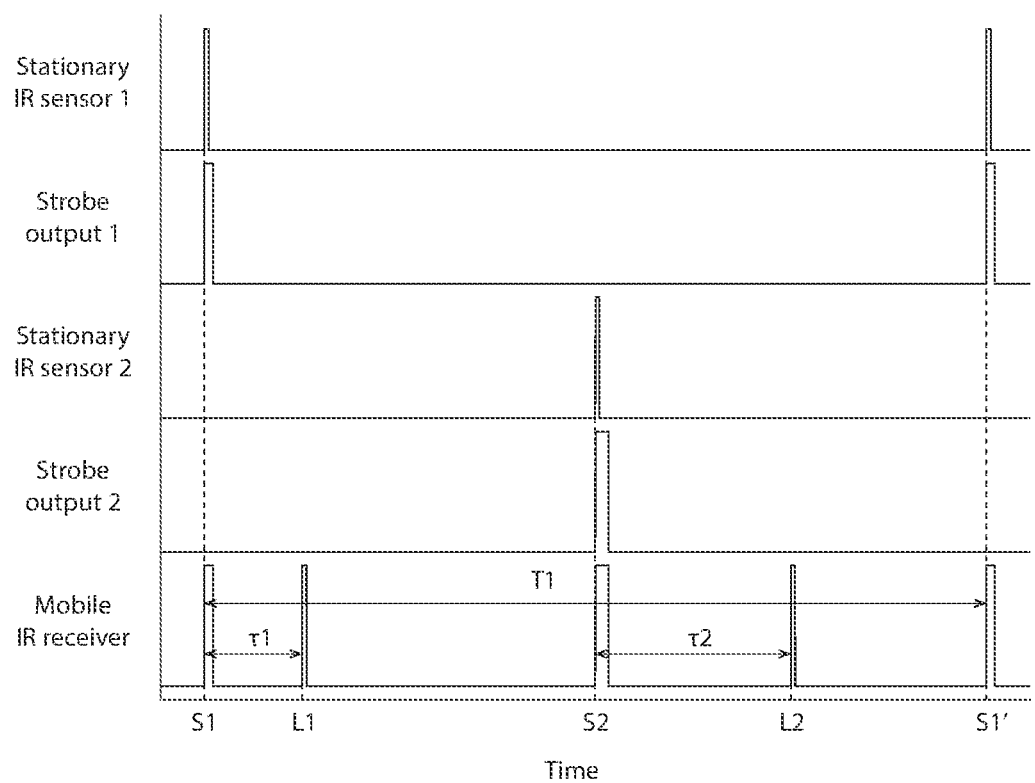

FIG. 25 shows the schematic temporal diagram of optical signals in the system of FIG. 24.

Figure 26:
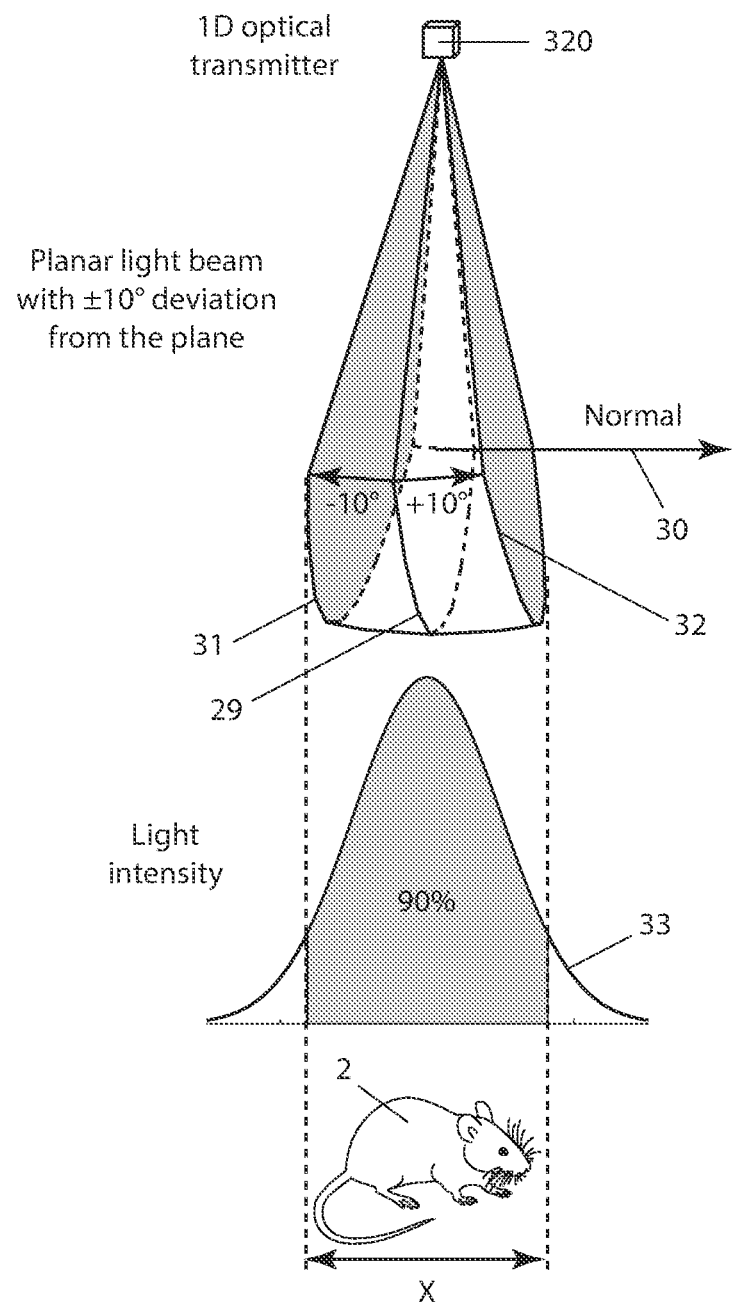

FIG. 26 shows the margins of acceptable angular divergence of the beam and the thickness of the light beam to be considered planar in the current invention. The angular divergence is expressed in absolute angular deviation (90% of light power is in the angle ±10°), and beam thickness is shown relative to the maximal dimension (length) of the tracked animal (90% of light power has thickness equal to animal length).

Figure 27:
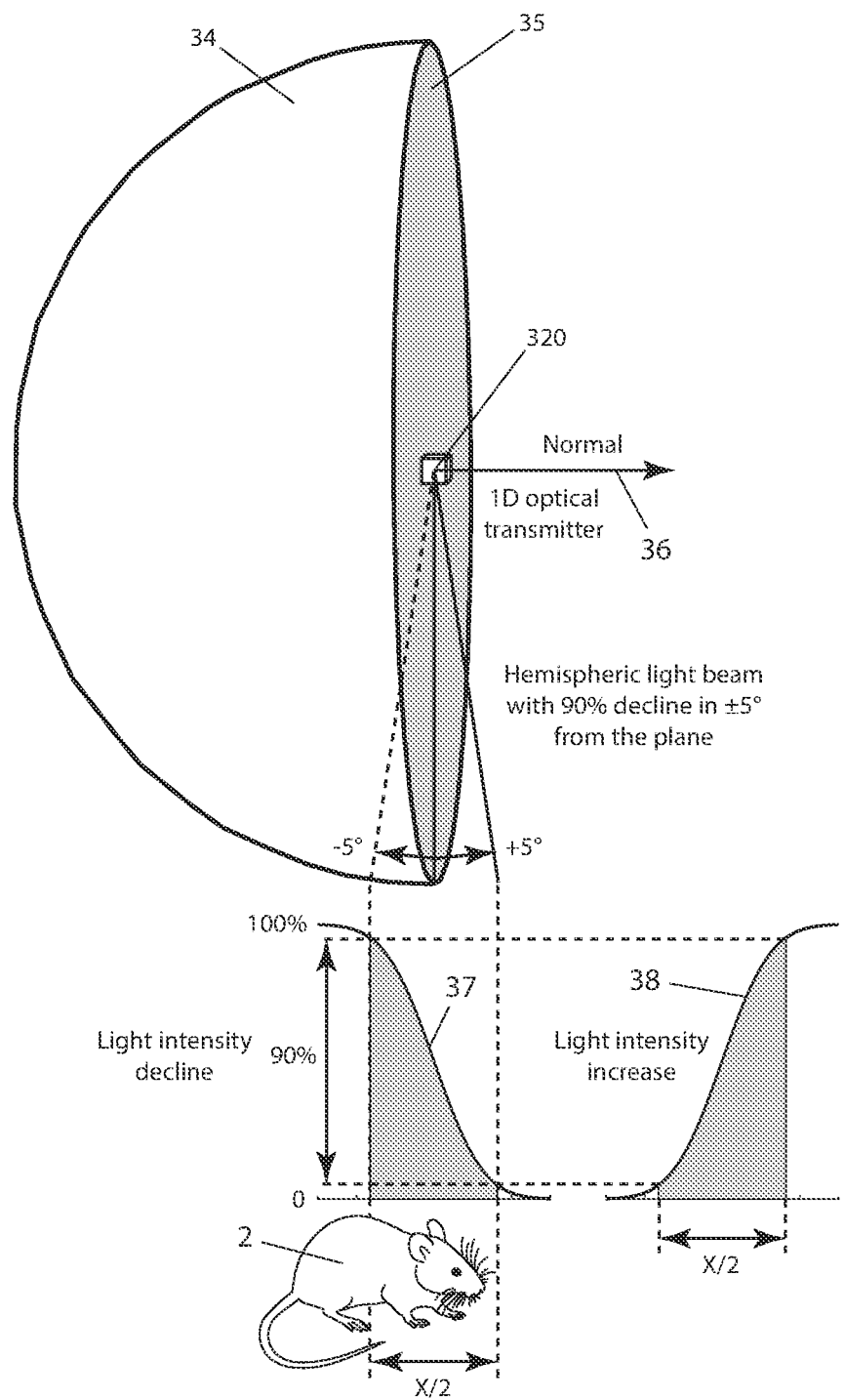

FIG. 27 shows an example of an anisotropic light beam with planar transverse gradient of light power. The localized light source illuminates only one hemisphere (shown), leaving the opposite hemisphere dark (not shown). The abrupt decline in light intensity at the border between these two hemispheres is considered a planar transverse gradient if 90% of light attenuation is in the ±5° margin of this border. The thickness of the layer where the light intensity declines or increases should not exceed one half of animal length for reliable animal tracking.

Figure 28:
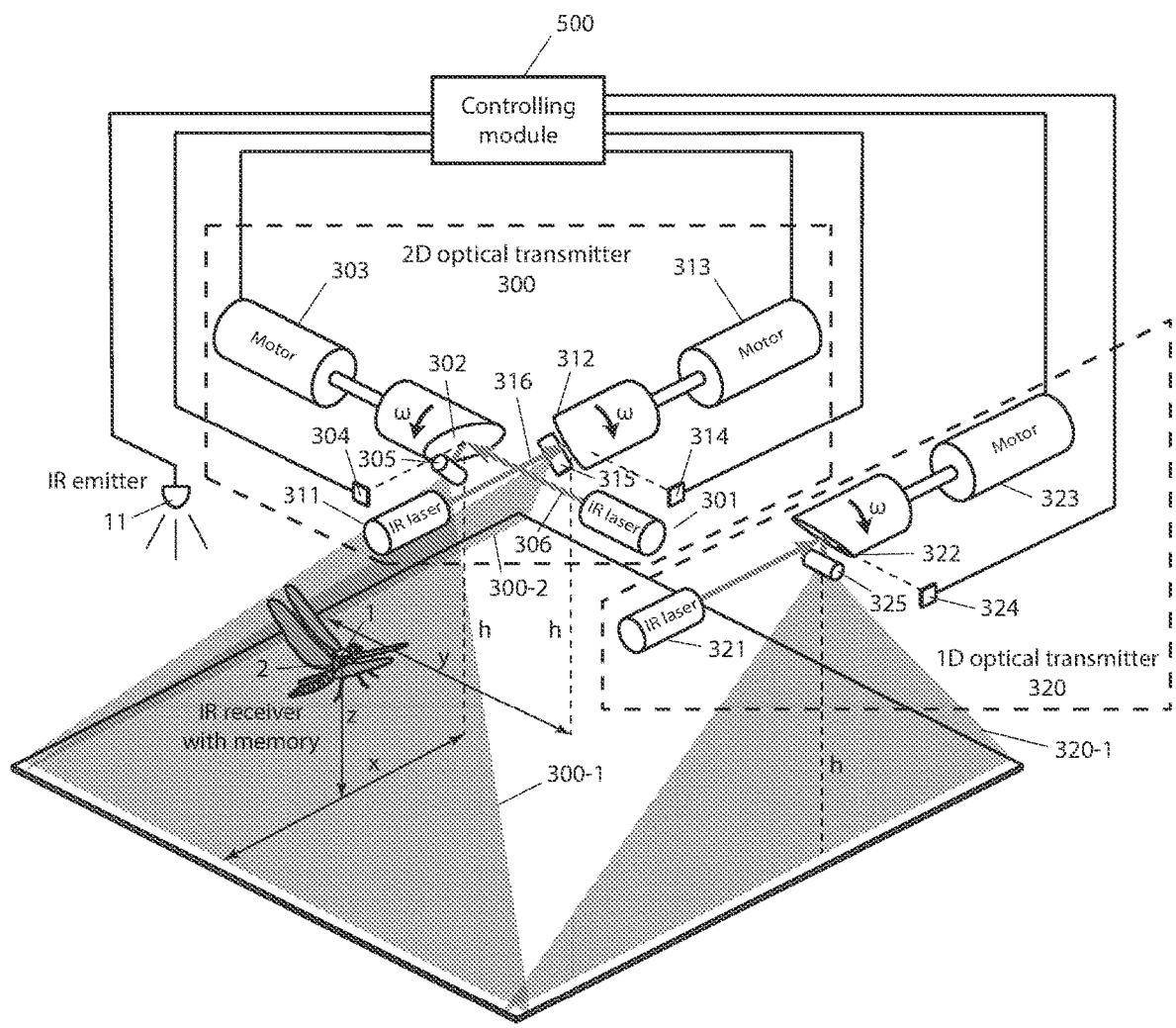

FIG. 28 shows the realization of the optical system of the current invention for three-dimensional tracking of a flying animal (a dragonfly). Three rotated anisotropic laser beams produced by three optical transmitters are needed for optical three-dimensional tracking. At least one transmitter should be spatially separated from the other two.

Figure 29:
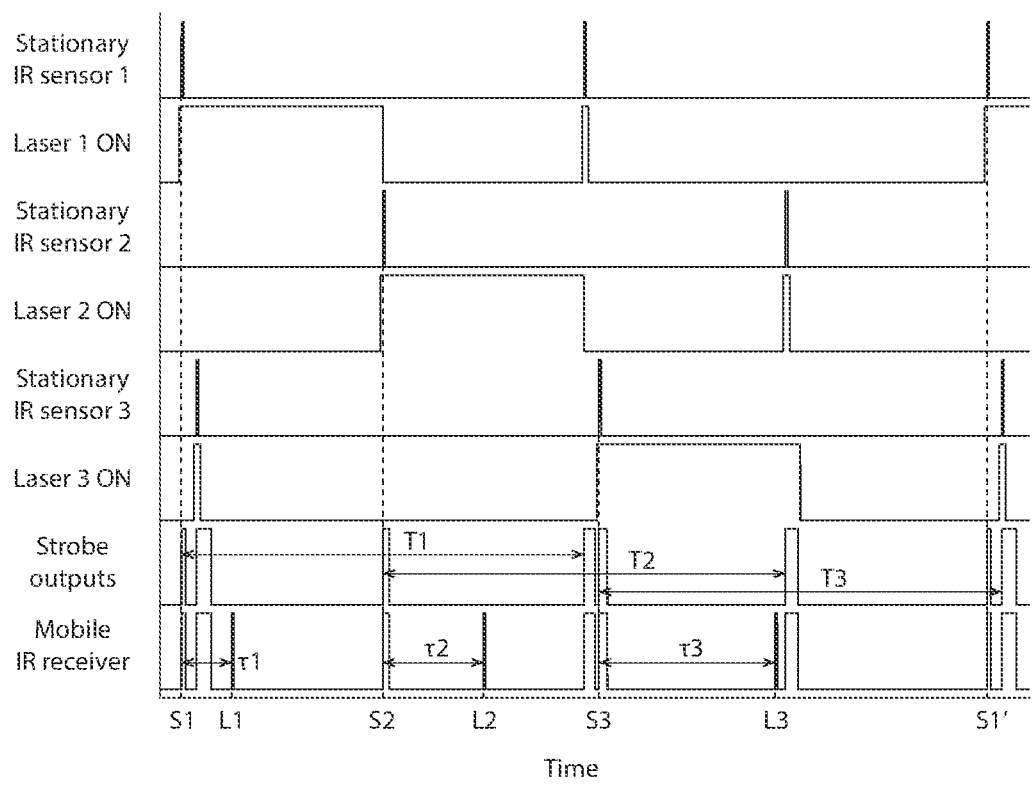

FIG. 29 shows a schematic temporal diagram of optical signals in the system of FIG. 28.

Figure 30:
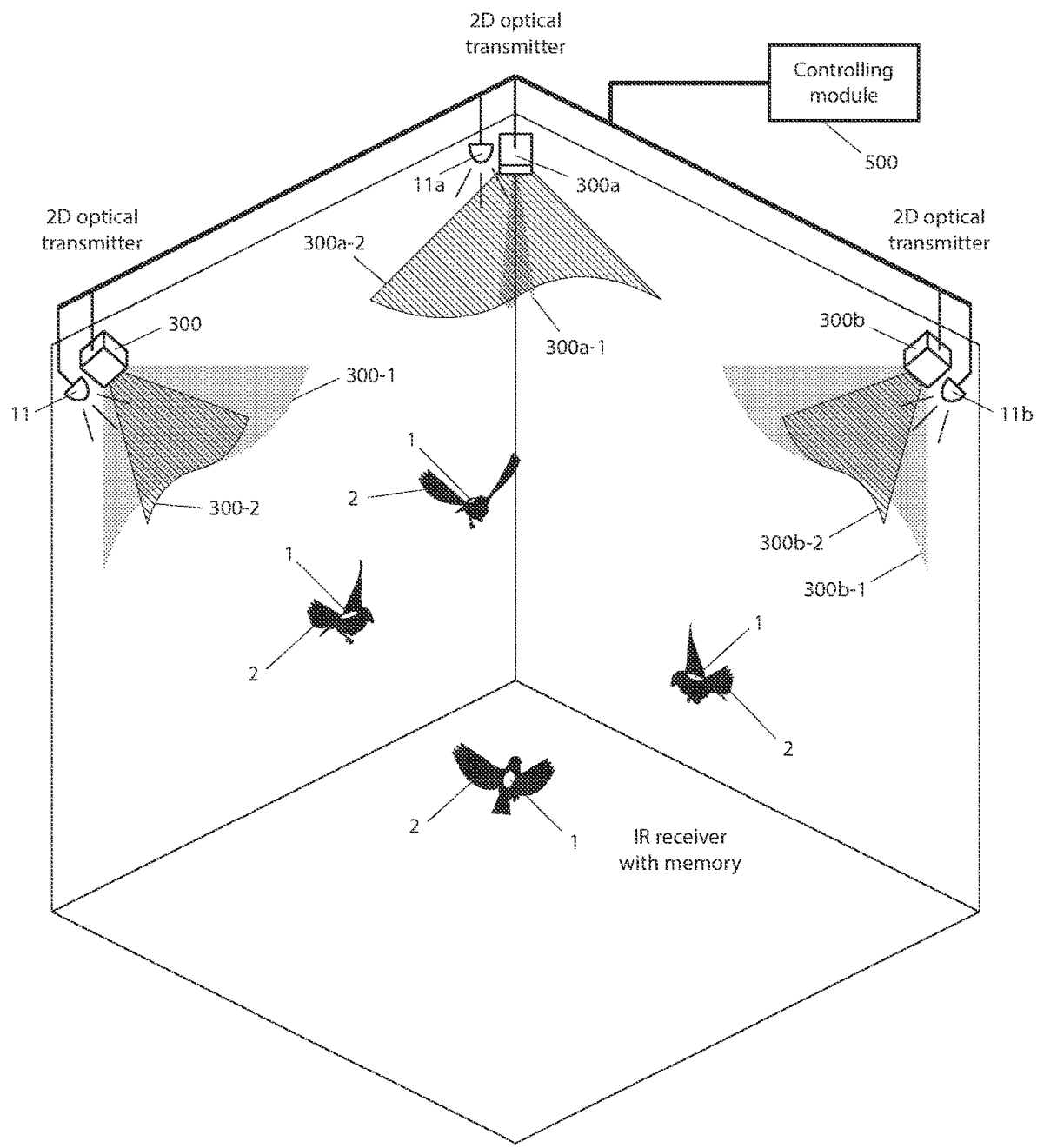

FIG. 30 shows the realization of the optical system of the current invention for three-dimensional tracking of multiple flying animals (birds). Note that the optical system needs direct visibility from stationary optical transmitters to animal-attached receivers. To permit tracking in the event of occasional occlusion of some optical paths by the animals, additional optical transmitters are introduced for redundancy.

Figure 31:
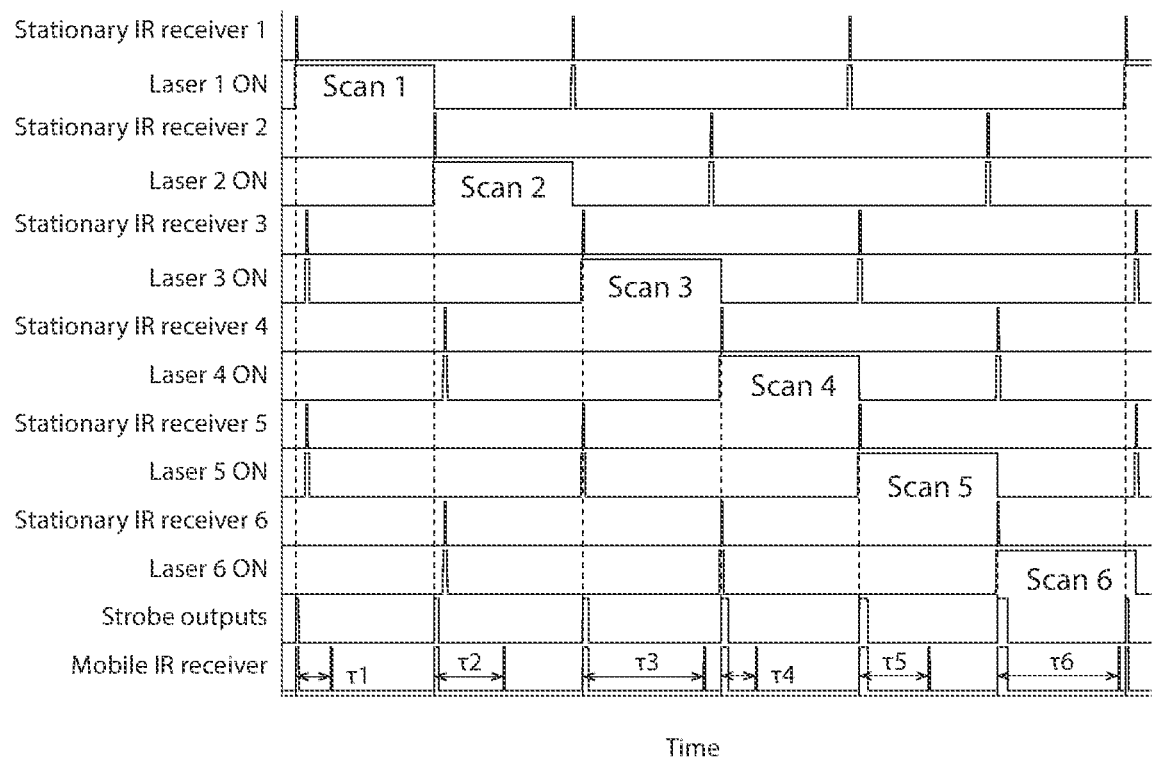

FIG. 31 shows the schematic temporal diagram of optical signals in the system of FIG. 30.

Figure 32:
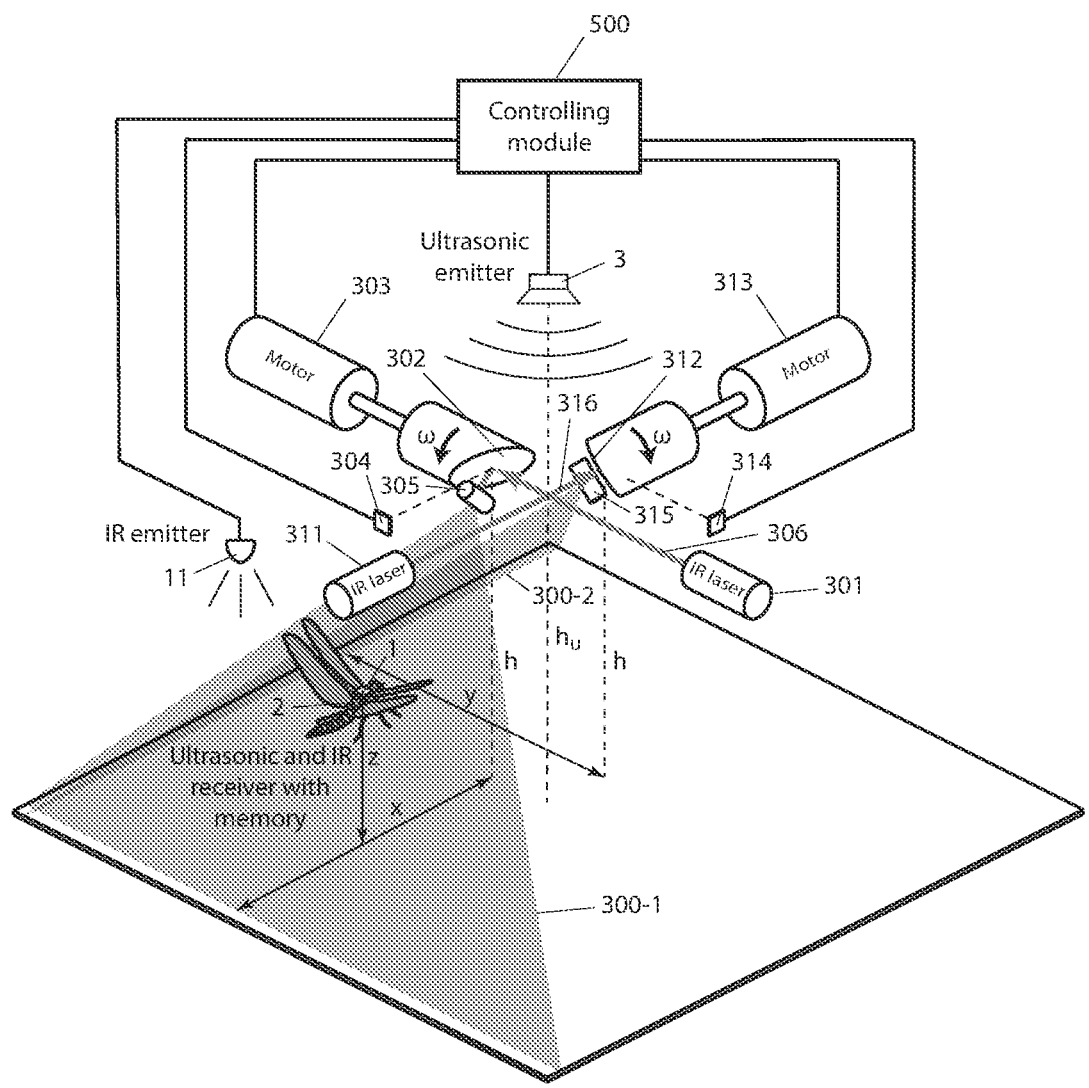

FIG. 32 presents the realization of a hybrid (ultrasonic and optical) 3D animal tracking system. Note that in this system all emitting devices—two optical transmitters and an ultrasonic emitter—can be spatially close to each other.

Figure 33:
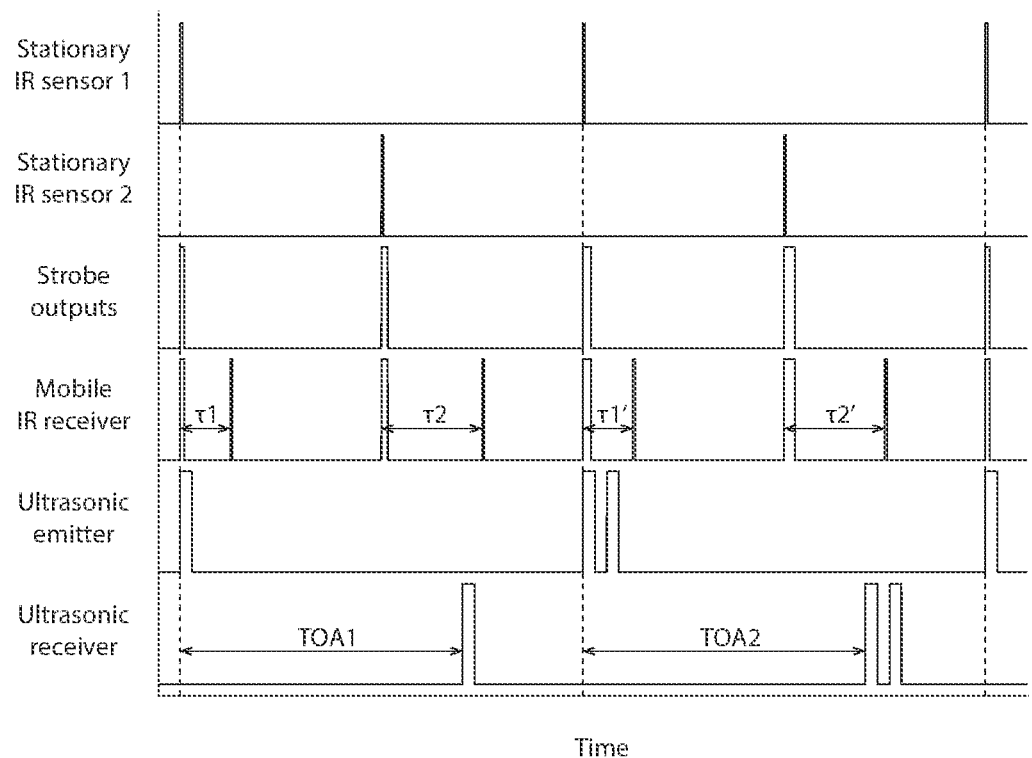

FIG. 33 shows the schematic temporal diagram of optical and ultrasonic signals in the system of FIG. 32.

Figure 34:
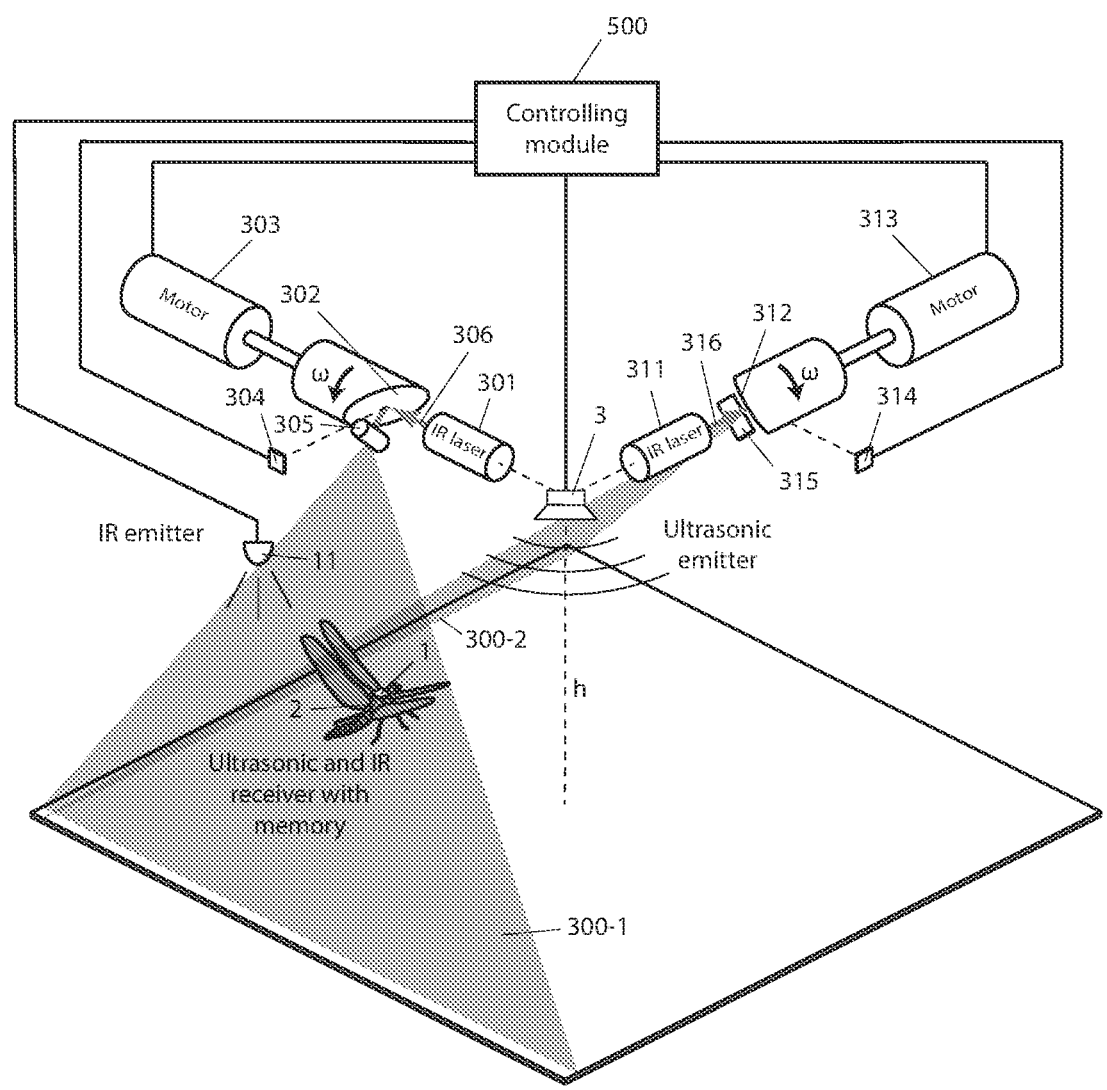

FIG. 34 presents another realization of a hybrid (ultrasonic and optical) 3D animal tracking system. In this system the ultrasonic emitter, being a center of origin of spherical ultrasonic waves, is placed at the intersection of the axes of rotation of two anisotropic light beams to simplify computation of position of the mobile device.

Figure 35:
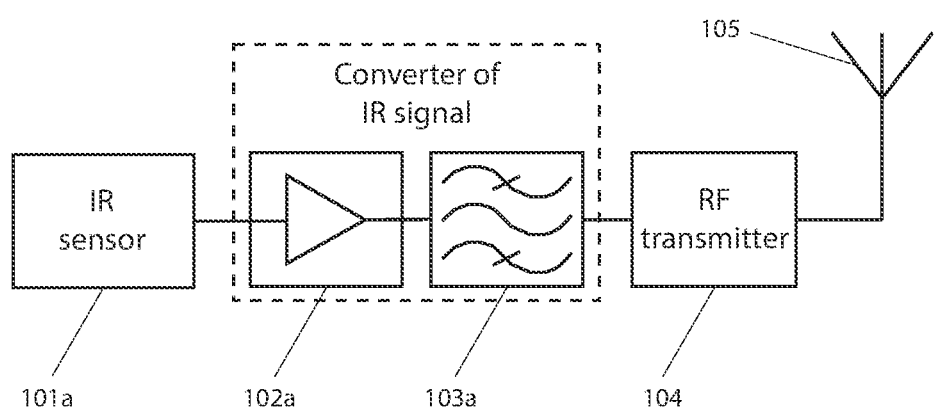

FIG. 35 is a schematic block diagram of the inner structure of a mobile, animal-attached optical receiving device with radio transmission to the data acquisition station.

Figure 36:
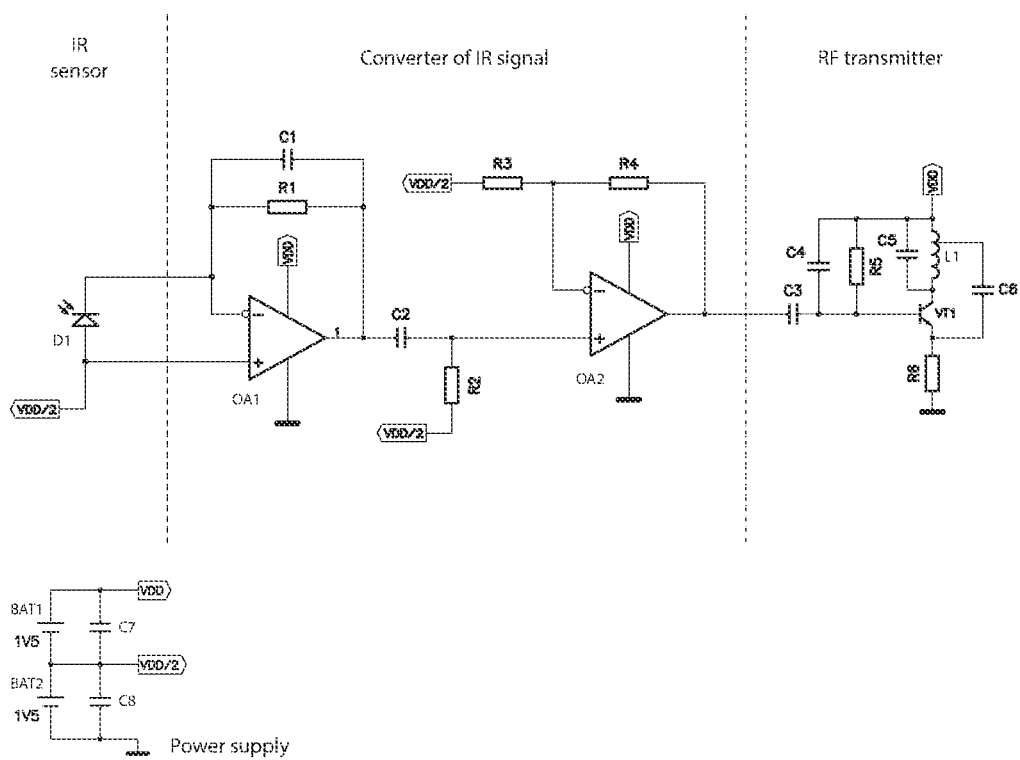

FIG. 36 is a circuit diagram of the mobile, animal-attached optical receiving device shown in FIG. 35.

Figure 37:
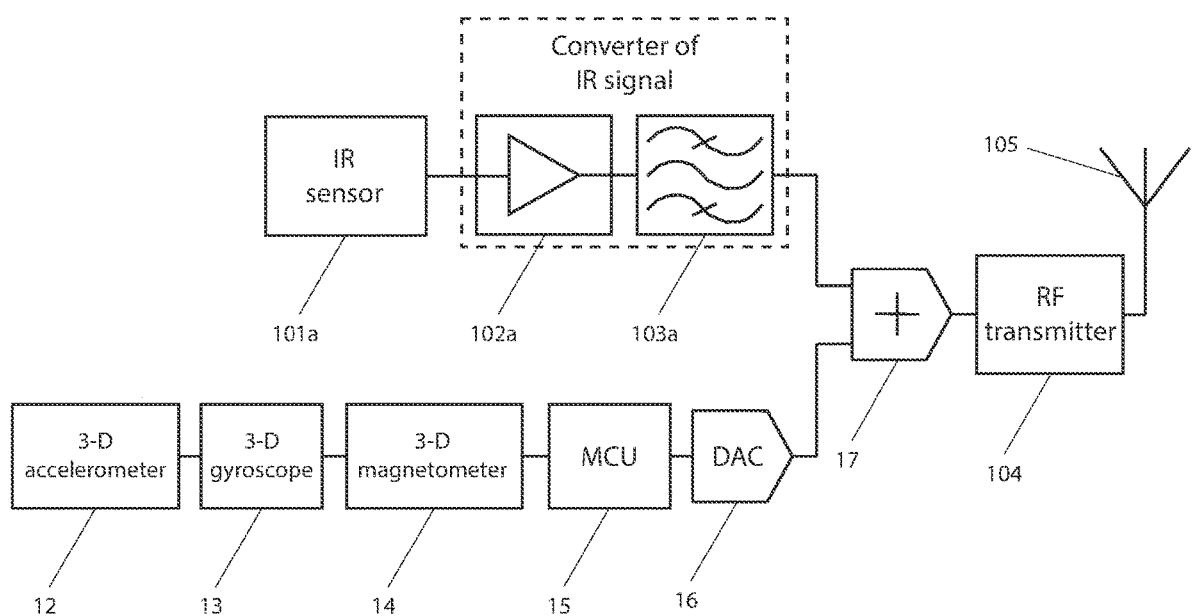

FIG. 37 is a schematic block diagram of the inner structure of a mobile, animal-attached optical receiving device with an integrated inertial tracking system consisting of 3D accelerometer, 3D gyroscope and 3D magnetic compass.

Figure 38:
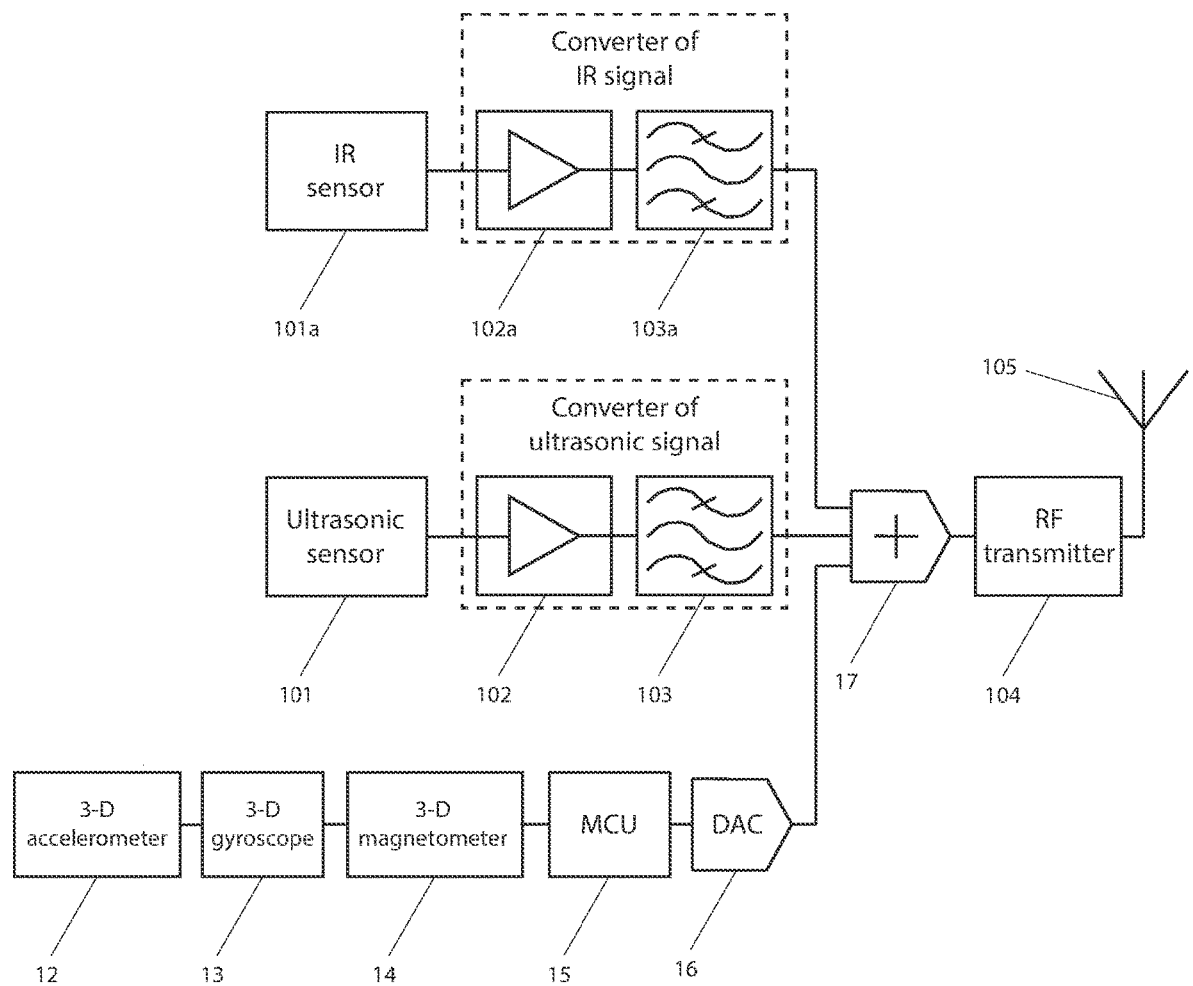

FIG. 38 is a schematic block diagram of the inner structure of a mobile, animal-attached, hybrid ultrasonic and optical receiving device with an integrated inertial tracking system consisting of 3D accelerometer, 3D gyroscope and 3D magnetic compass.

Figure 39:
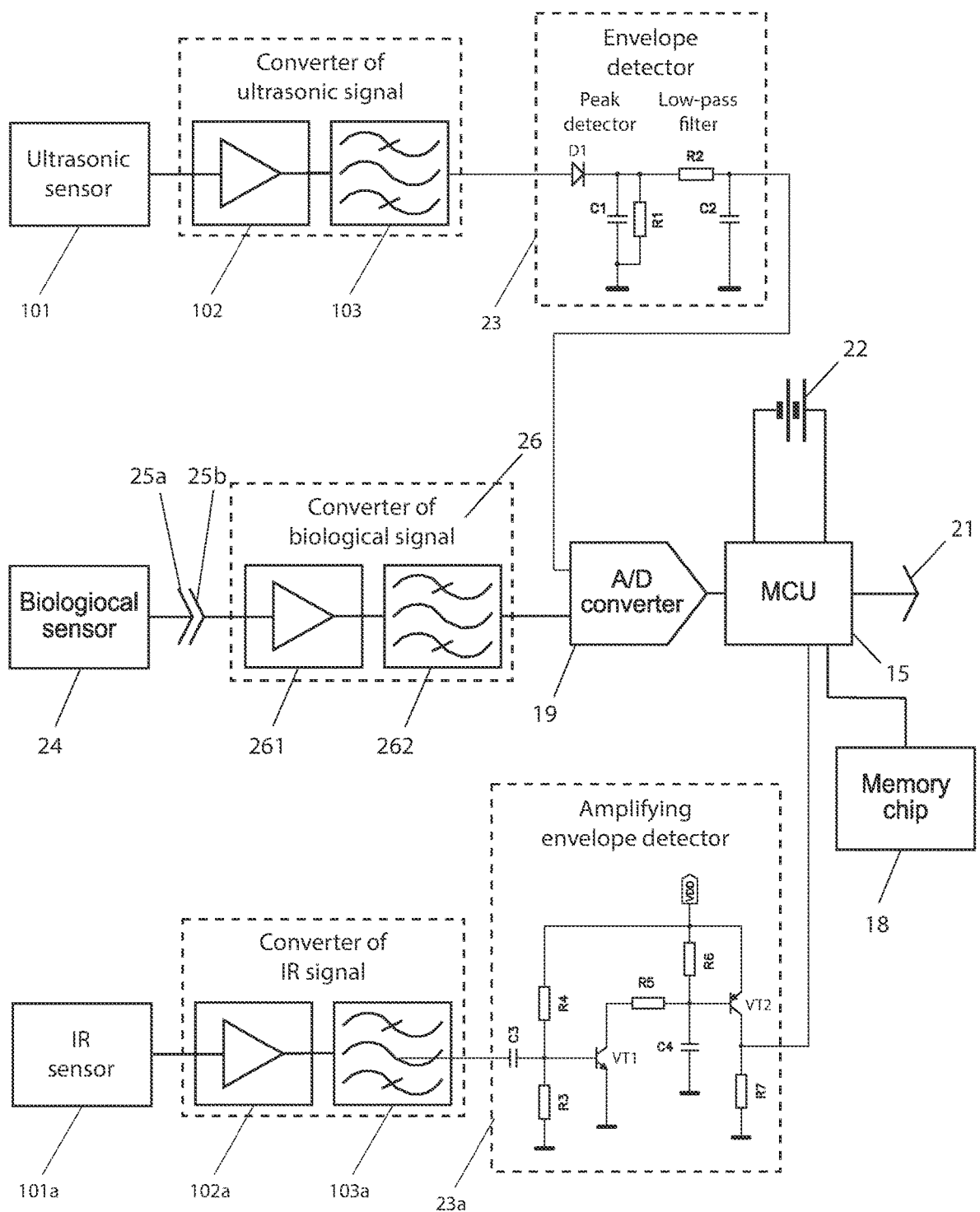

FIG. 39 is a schematic block diagram of the mobile, animal-attached, hybrid ultrasonic and optical receiving device with digitization and local storage of information from ultrasonic and IR sensors and from biological sensors in the mobile device.

Figure 40:
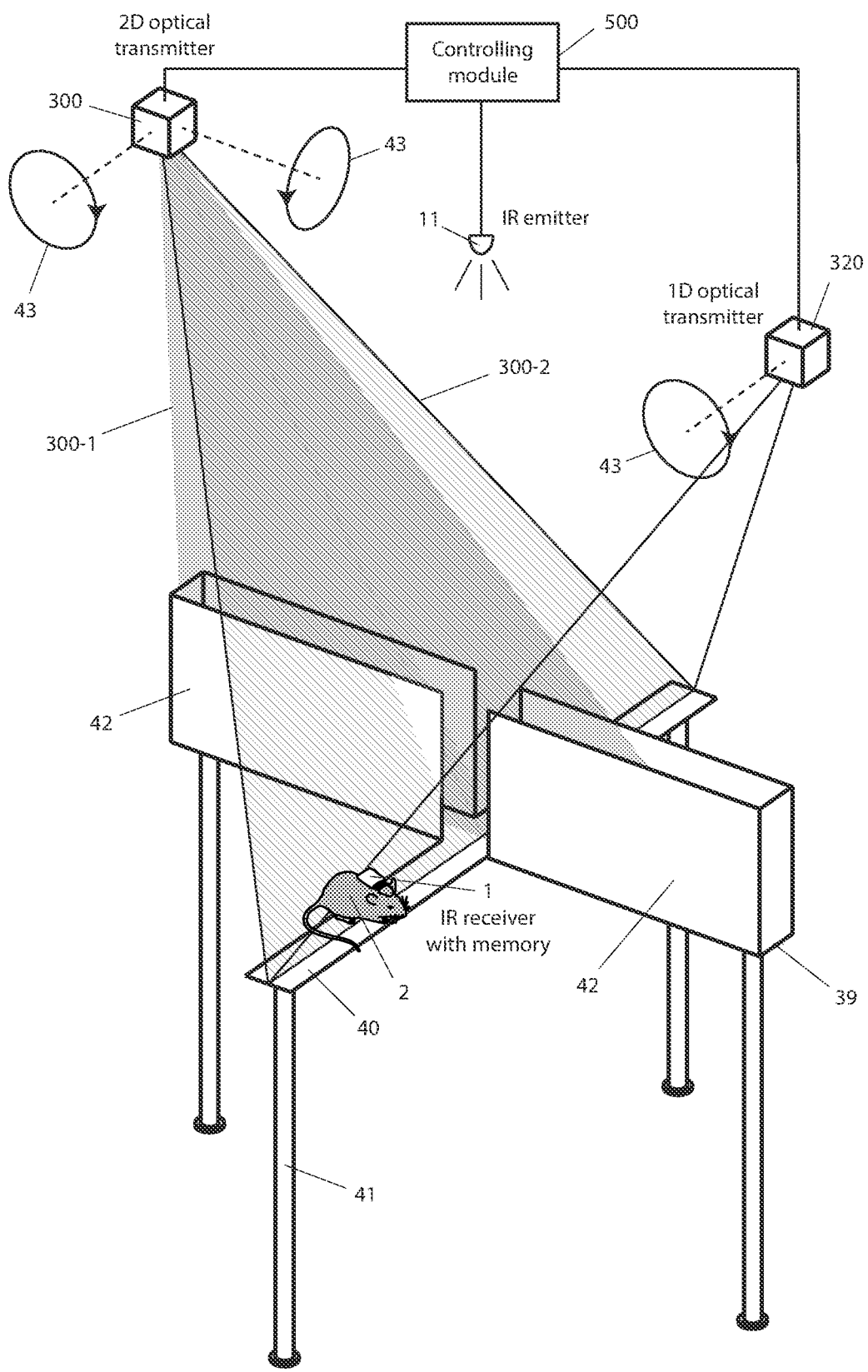

FIG. 40 shows the applicability of the current invention for optical 3D tracking of a laboratory mouse engaged in a popular behavioral task, an elevated plus-maze. The third vertical dimension is needed to register rears and head dips. To record these movements, the optical receiver with memory is attached to the head of the animal.

Figure 41:
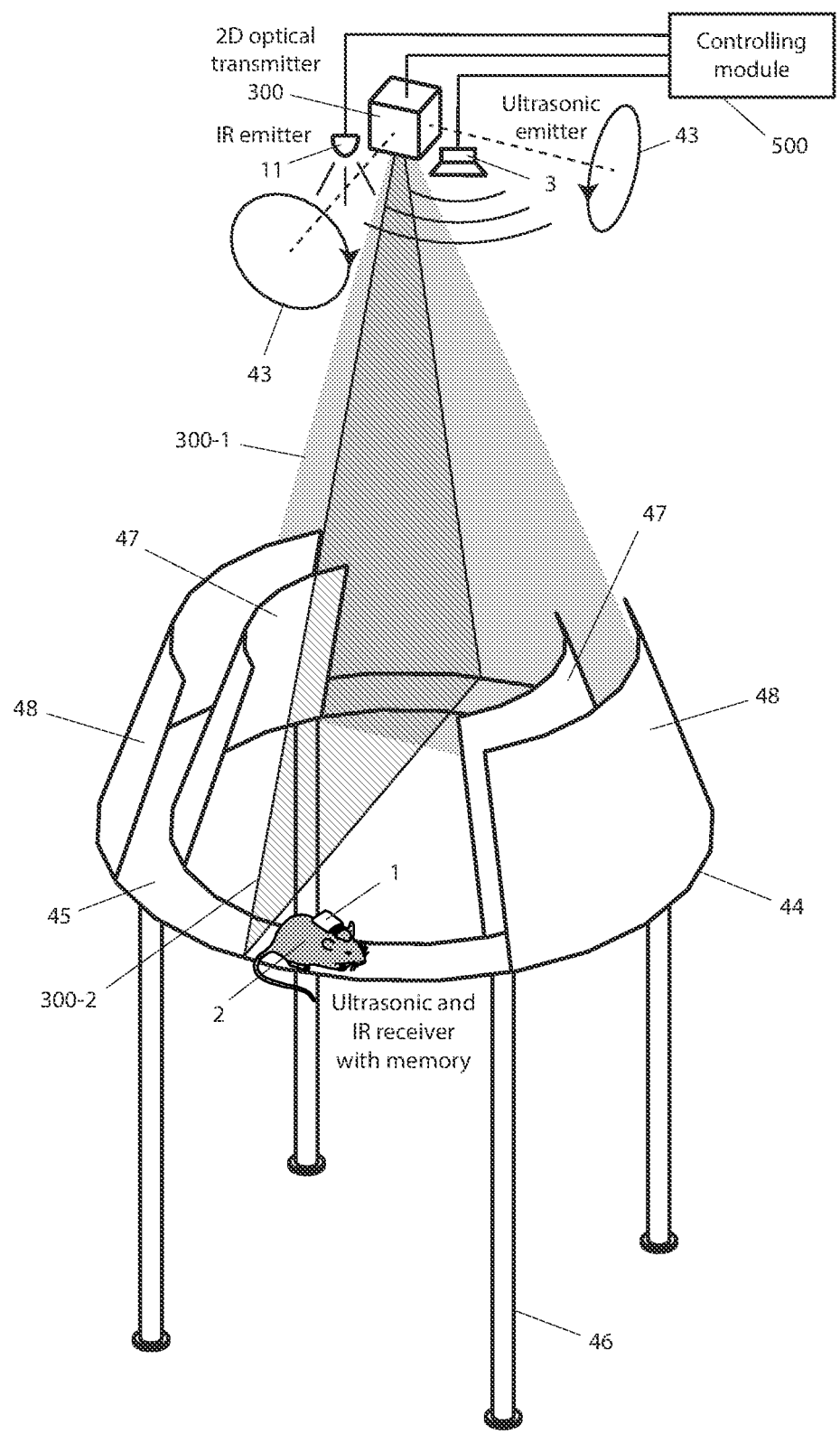

FIG. 41 shows the applicability of the current invention's hybrid ultrasonic and optical 3D tracking for monitoring a laboratory mouse engaged in another popular behavioral task, an elevated O-maze. This example shows the advantage of the hybrid tracking system. Neither optical nor ultrasonic systems can be used in the current behavioral task because of shadowing (occlusion) produced by the walls. The proposed hybrid tracking system, however, is capable of detecting rears and head dips with the help of an ultrasonic sensor incorporated in the head-mounted mobile device. Animal position in the horizontal plane is determined optically.

Figure 42:
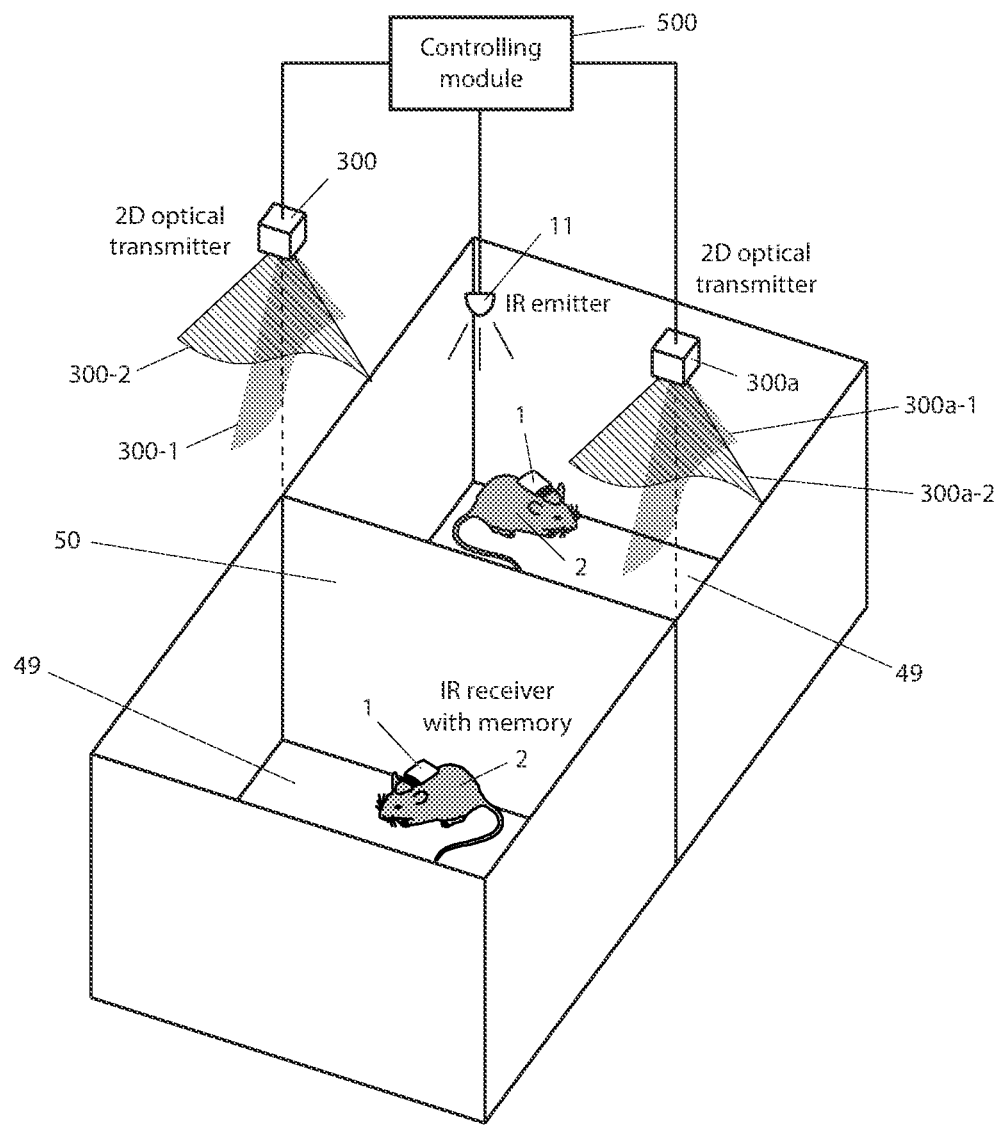

FIG. 42 shows the applicability of the current invention's optical 3D tracking for monitoring of two laboratory mice performing another popular behavioral task, an open-field test. Note that maximal number of mice that can be simultaneously monitored in two independent arenas by a couple of 2D optical transmitters is limited to two because of area shadowing by separators in the case of a larger number of arenas.

Figure 43:
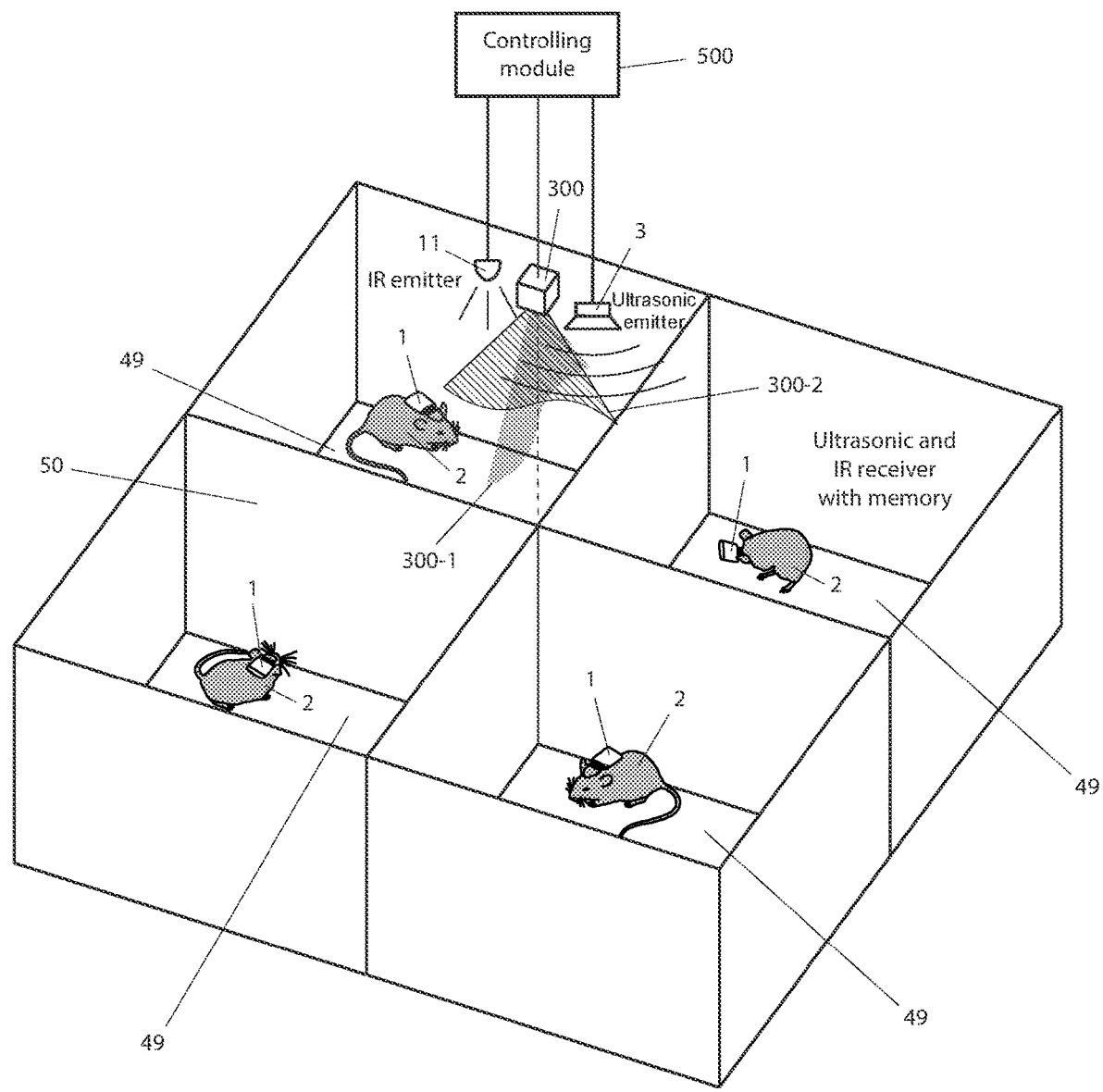

FIG. 43 demonstrates an advantage of the hybrid ultrasonic and optical tracking of four mice in four independent, open-field arenas. Note that one 2D optical transmitter and one ultrasonic emitter are sufficient for simultaneous 3D tracking of all four animals.

DETAILED DESCRIPTION OF THE INVENTION

Reference will now be made in detail to the preferred embodiments of the present invention, examples of which are illustrated in the accompanying drawings.

Figure 1:
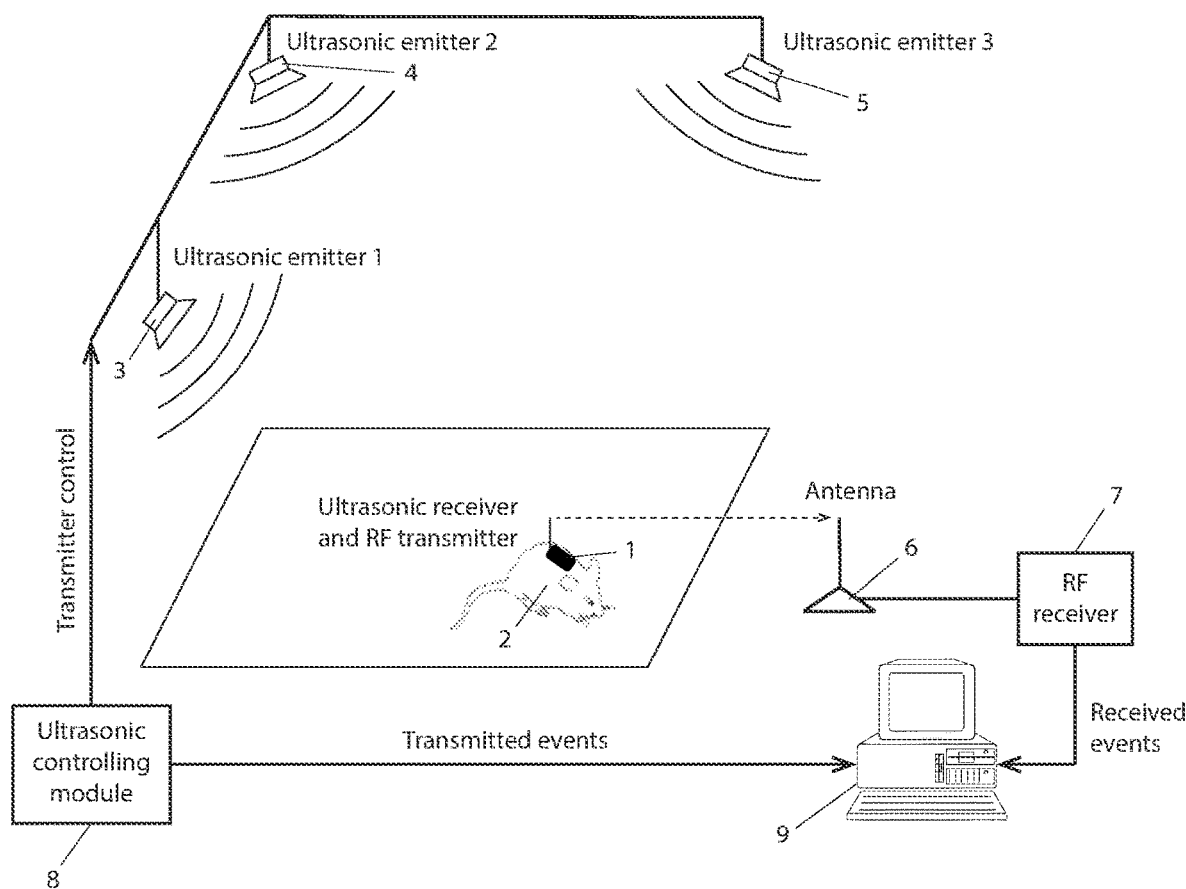
FIG. 1 is a configuration view showing the ultrasonic tracking system for small animal research. The system has a wired connection between three ultrasonic emitters and a data acquisition station, and a mobile, animal-attached device incorporating an ultrasonic receiver with a radio transmitter, according to one embodiment of the invention.
Figure 2:
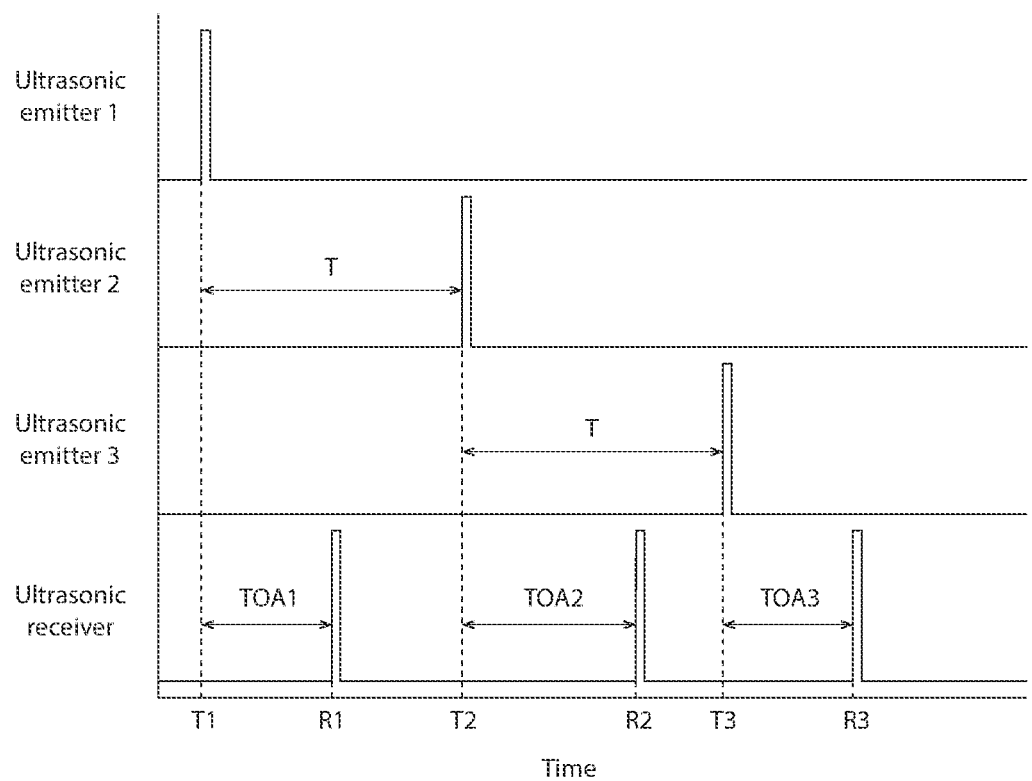
FIG. 2 shows a schematic temporal diagram of transmitted and received ultrasonic signals in the embodiment of the invention depicted in FIG. 1.

With reference to FIGS. 1-2, a method of ultrasonic detection of the position of an animal in a 3D space comprises attachment of a mobile device 1 to an animal 2, reception by the mobile device 1 at a receipt time R1 of an ultrasonic signal transmitted from a source location 3 at a transmission time T1. Reception by the mobile device 1 at an additional receipt time R2 of an additional ultrasonic signal transmitted from an additional source located at an additional source location 4 at an additional transmission time T2, wherein the transmission time and the additional transmission times each have a predetermined time interval from each T. The method can repeat the act of receiving a further additional ultrasonic signal from an additional ultrasonic emitter 5 with the reception time R3 and transmission time T3 accordingly. In the current embodiment of the invention, the mobile device separates the received ultrasonic signal from animal vocalizations, animal-produced noises and other noises. This separation can be also done later in the following stages of signal processing (e.g., at the receiver side) or can be split between the mobile device and stationary equipment, where a part of signal separation is done in the mobile device and another complementary part in the stationary equipment. Requirements for such signal separation and details of its realization will be described later in the detailed description of the invention. The mobile device 1 transmits a radio signal containing information about ultrasonic signal arrival at the time of signal arrival to the antenna 6 of a radio frequency receiver 7. The ultrasonic controlling module 8 sends information to the computer 9 at times when ultrasonic signals are transmitted. The computer, having an internal clock, computes time of information arrival and animal position from the TOAs TOA1=R1−T1, TOA2=R2−T2, TOA3=R3−T3 by well-known methods. For example, if the transmitter locations are described as vectors L1, L2 and L3 in a Cartesian coordinate system and sound speed v is known, vector X describing the unknown location of the animal will be found from the solution of the following system of equations:

$$|L1-X|=v \cdot TOA1$$

$$|L2-X|=v \cdot TOA2$$

$$|L3-X|=v \cdot TOA3$$

The speed of the sound in the air is computed by measuring ambient temperature, ambient humidity or both.

The solution of this system can be found by many numerical methods, for example, by the Newton method. To increase the robustness of perception of ultrasonic signals, one can use a greater number of ultrasonic emitters operated in a similar way. In this case, the system of equations will have more equations than the number of unknown variables (i.e., over-determined). An approximate solution of such a system can be found by numerical methods that minimize residuals. Alternatively, a subset of emitters with the best positions relative to the receiver can be selected, and TOAs from them can be used for calculation of animal position. Note that the sequence of ultrasonic signals can be repeated periodically to determine animal location with the desired periodicity, say 10 Hz. Only TOAs of direct, non-reflected ultrasonic signals are analyzed. Ultrasonic signals are transmitted with the time span sufficient for attenuation of ultrasonic waves reflected from the floor and other objects to avoid mixing of direct, useful signals with reflected signals from preceding ultrasonic emissions.

Figure 3:
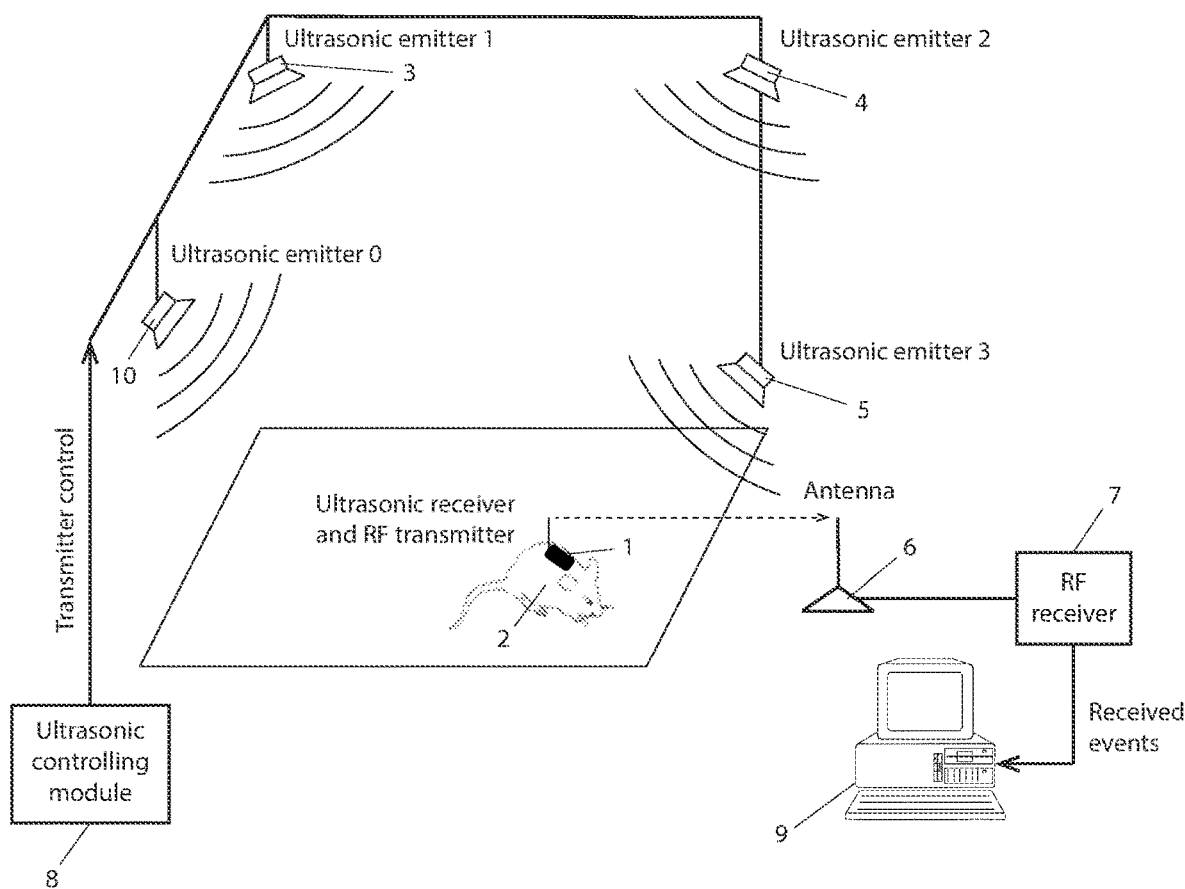
FIG. 3 represents an embodiment of the invention with four ultrasonic emitters and without any wired synchronizing link between the ultrasonic emitters and a data acquisition station.
Figure 4:
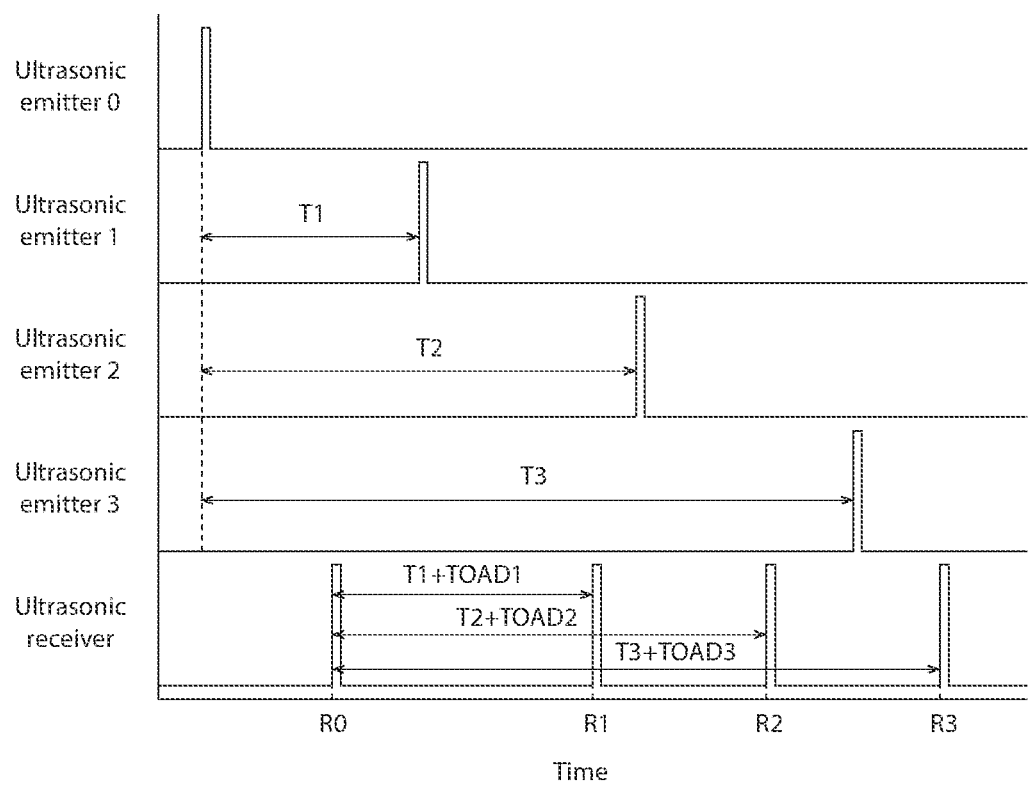
FIG. 4 shows a schematic temporal diagram of transmitted and received ultrasonic signals in the embodiment of the invention depicted in FIG. 3.

With reference to FIGS. 3-4, the second embodiment of the invention is similar to that previously described, but it consists of four ultrasonic emitters instead of three as before. As before, the system is designed for 3D tracking. Emitter 10 with the number 0 is added to eliminate the wired synchronization link between the ultrasonic controlling module 8 and the computer 9; the link can be inconvenient in some cases. Ultrasonic signals are emitted with the known time intervals T1, T2 and T3 between the first and the three following signals, respectively (FIG. 4). The mobile device receives these signals at reception times R0, R1, R2 and R3. Like in the previous embodiment, these signals should be separated from animal vocalizations and noise by the method that will be described later. When this is done, the receiver can compute time differences R1−R0, R2−R0 and R3−R0 between reception times. Knowing these differences and the time spacing T1, T2 and T3 of transmission times, one can get three TOADs: TOAD1=R1−R0−T1, TOAD2=R2−R0−T2 and TOAD3=R3−R0−T3. Knowing these TOADs, one can compute the position of the mobile device (and the animal) in a way similar to the computing of coordinates in a GPS receiver. For details of computation, please refer to (Z Daniel Deng et al., 2011) or (Yayan et al., 2015). If the animal moves in a 2D plane, one can decrease the number of ultrasonic emitters by one.

Figure 5:
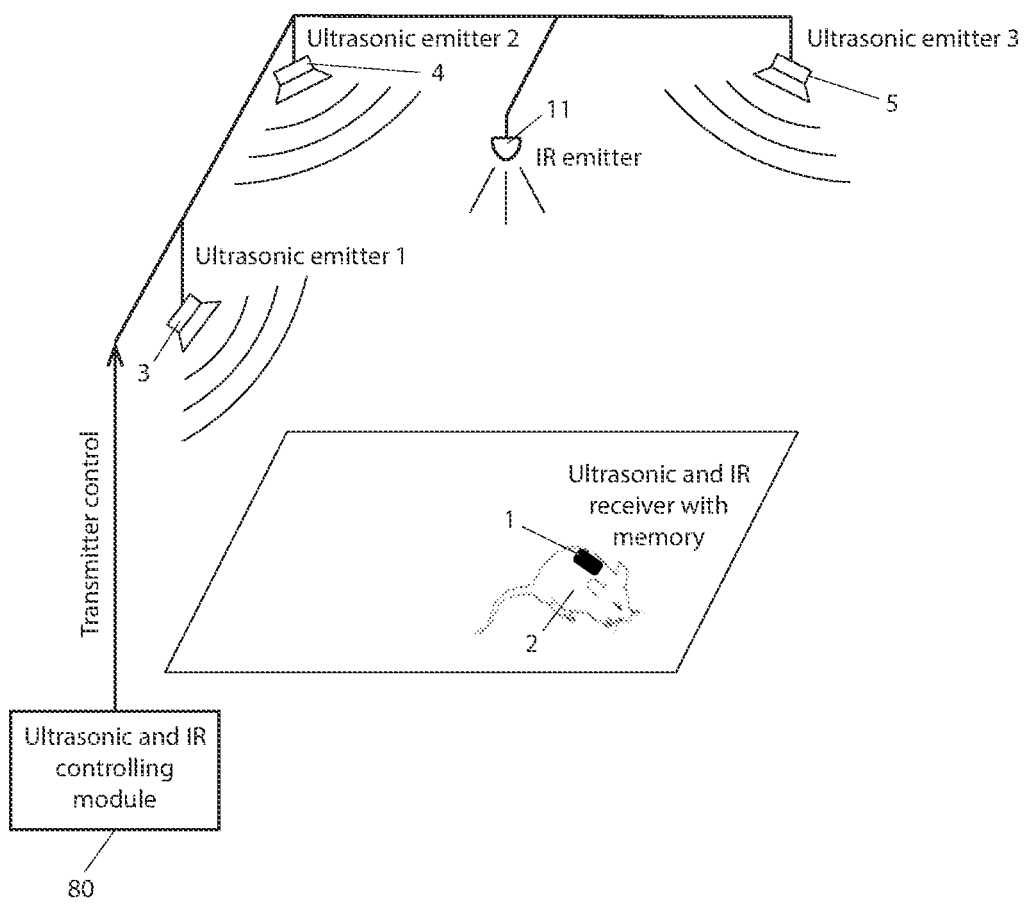
FIG. 5 represents an embodiment of the invention with three ultrasonic emitters and one IR emitter for synchronization. A mobile, animal-attached device receives ultrasonic and IR signals and stores information about them in local memory for further downloading and analysis.
Figure 6:
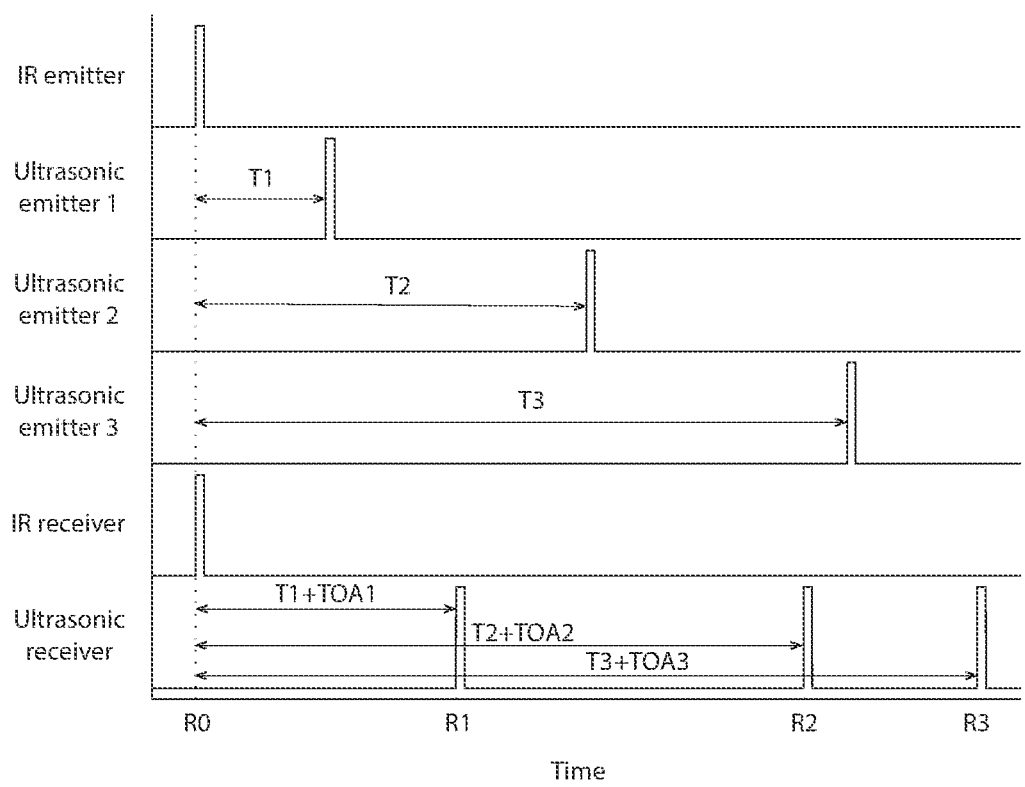
FIG. 6 shows a schematic temporal diagram of transmitted and received ultrasonic and IR signals in the embodiment of the invention depicted in FIG. 5.

With reference to FIGS. 5-6, the third embodiment of the invention has three ultrasonic emitters 3-5 and one synchronizing IR emitter 11 for sending an IR synchronizing (strobe) pulse to the mobile device 1. The mobile device incorporates amplification and ultrasonic separation cascades like in the previous two embodiments, but it also has an analog-digital converter (ADC), a microprocessor and a non-volatile memory for the data storage. The microprocessor should have a clock to detect times of different events or a timer to measure time intervals between events. Details of the realization of the mobile module in this embodiment are given later. The sequence of events for determining the position of the animal starts with transmission of an IR signal by a IR emitter 11 and, practically simultaneously without a measurable delay, reception of this IR signal by an IR receiver incorporated in the animal-attached, mobile device 1 (FIG. 6). Ultrasonic signals are emitted by the emitters at positions 3, 4 and 5 at transmission times T1, T2 and T3 relative to reception of an IR signal. The receiver receives these signals at reception times R1, R2 and R3, respectively. TOAs are computed as TOA1=R1−R0−T1, TOA2=R2−R0−T2 and TOA3=R3−R0−T3. Knowing the TOAs, the coordinates of the mobile device are computed as is described in the first embodiment of the invention. The main benefit of this embodiment is its simplicity, because the mobile module does not have a radio transmitter, and the radio receiver with the computer for data acquisition is absent. Also, this system will not have the signal disturbances and noise that can be observed in analog radio transmission. A small disadvantage is that the user receives information about animal location not in a real time but after the end of the recording session, when the mobile module is taken from the animal for wired data downloading. To cope with this disadvantage, one can implement a wireless transmission of small pieces of data for on-line monitoring.

Figure 7:
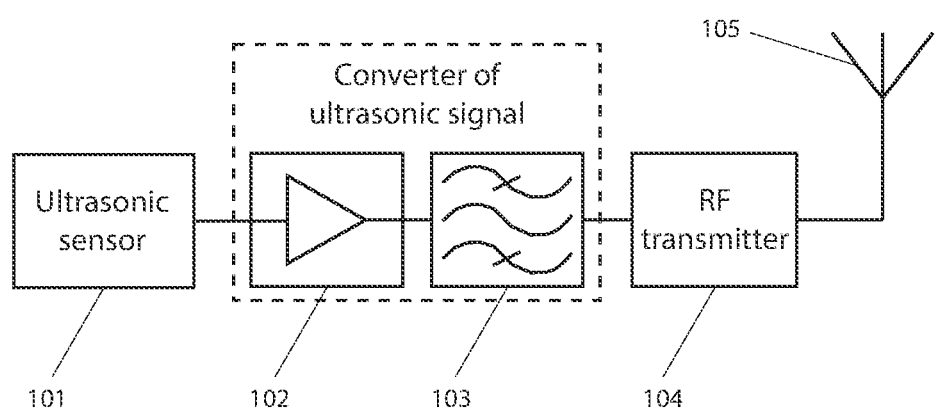
FIG. 7 is a schematic block diagram of the inner structure of a mobile, animal-attached ultrasonic receiving device.

Note that an alternative embodiment is possible in which the IR emitter is controlled by an independent controlling module that does not necessarily have a wired connection to an ultrasonic controlling module. In such a realization, the ultrasonic controlling module can be equipped with an IR receiver similar to that of the animal-attached, mobile module. The reception of IR strobe pulses sent from the independent controlling module by the ultrasonic controlling module can evoke a sequence of emission of ultrasonic signals by the ultrasonic controlling module. Alternatively, the ultrasonic controlling module can be equipped with memory and a clock to detect the time of IR signal arrival. The memory can be used to store information about the arrival time of the IR signal and the emission time of ultrasonic signals. Both types of signals, IR and ultrasonic, can be generated independently by the independent controlling module and the ultrasonic controlling module, respectively. The IR strobe pulses simultaneously arriving to both systems can be used for precise synchronization of arrays of ultrasonic emission and reception timing events. With reference to FIG. 7, the mobile device 1 contains ultrasonic sensor 101 for conversion of ultrasonic signal to electrical signal, an analog conditioning circuitry for amplification 102 and filtering 103 of electrical signals and a radio frequency transmitter 104 with an integrated antenna 105 for radio broadcasting of ultrasonic signals to the stationary data acquisition system.

Figure 8:
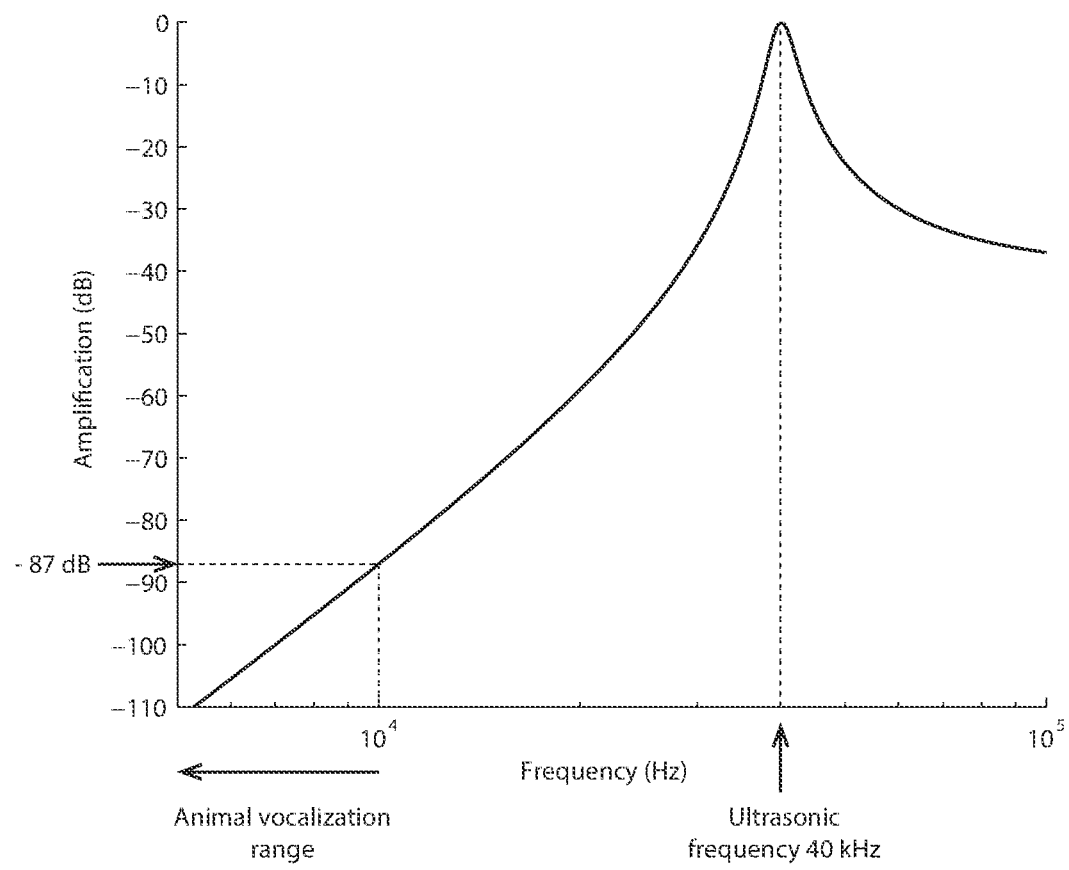
FIG. 8 is an example of the magnitude response of the transfer function of a filter separating ultrasonic signals from animal vocalizations.
Figure 9:
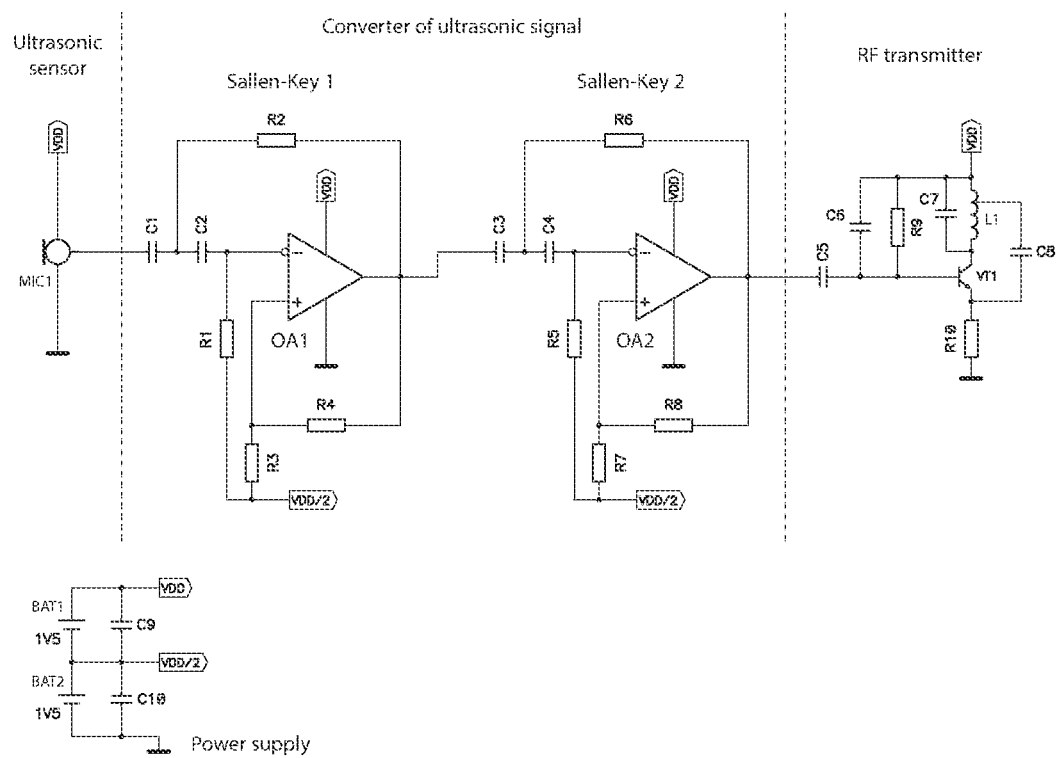
FIG. 9 is a circuit diagram of the mobile, animal-attached ultrasonic receiving device with radio transmission to the data acquisition station.

A typical laboratory bird, the zebra finch, can emit sounds with frequencies up to 10 kHz (FIG. 8). The most widespread ultrasonic emitters have a transmitting frequency of 40 kHz. Thus, the receiving mobile module should be able to receive 40 kHz ultrasonic signals with 10 kHz disturbing signals in the background. A bird can produce sound with intensity up to 100 dB (relative to 20 pPa standard sound pressure level). Ultrasonic emitters usually have similar loudness. However, the animal's head may be within 1 cm of the ultrasonic receiver, whereas typical distance from the ultrasonic emitter is about 1 m. While sound amplitude attenuates linearly with distance from the source, a 1:100 distance ratio will lead to amplitude of animal vocalization signal at the ultrasonic receiver that is 100× greater than amplitude of the ultrasonic transmitter signal. To equalize amplitudes, one has to suppress the animal vocalization signal by 40 dB. If we assume that disturbances <1% in amplitude are acceptable, we have to suppress further the animal vocalization signal by 40 dB, to have total suppression of 80 dB. Essentially, this suppression should be achieved in a narrow frequency range of 10-40 kHz. The absolute value of a transfer function satisfying these requirements is shown in FIG. 8. The transfer function is normalized to have zero attenuation at the ultrasonic frequency 40 kHz. This function is constructed by sequential cascading of two second-order high-pass filters with the quality factor Q=10 in each of them. One can see that attenuation in frequencies below 10 kHz is 87 dB better. The second-order high-pass filters can be realized by analog cascades (e.g., by Sallen-Key or multiple feedback structures). The complete electrical scheme of the mobile module with the signal separation cascade based on Sallen-Key filters is shown in FIG. 9. Alternatively, the filter could be a finite impulse response (FIR) filter, an infinite impulse response (IIR) filter or a combination of both. The ultrasonic signal is received by a microphone MIC1. The output of the microphone is connected to the input of the first Sallen-Key filter based on operational amplifier OA1 that also amplifies the signal. Output of the first amplification and filtration cascade is routed to the second, similar amplification cascade based on operational amplifier OA2. The combination of these two Sallen-Key structures represents a converter of the ultrasonic signal. The output of this converter is routed to the input of the radio frequency transmitter. In this particular case, this is a simple, single-transistor, frequency-modulation (FM) transmitter. Its main benefit is low power consumption, but a capacitive link between the transmitting coil antenna L1 and objects in the vicinity of the transmitter can degrade stability of the carrier frequency. The carrier frequency F is determined by inductance L1 and capacitance C7 as $F=1/(2\pi\sqrt{LC})$. Stability of the carrier frequency can be improved by implementation of a two-transistor transmitter with independent cascades for carrier frequency generation and signal transmission. The circuit is powered by a bipolar power supply consisting of two batteries BAT1 and BAT2 (1.5 V) with the capacitors C9 and C10. One can use several transmitters simultaneously with several animals in one chamber. To do this, the transmitters should have slightly different carrier frequencies determined by slightly different inductances L1 or capacitances C7. Modern SDRs are capable of receiving signals from several transmitters simultaneously. Thus, only one digital receiver is needed for handling radio signals from several animals. This shrinks the system cost significantly.

Figure 10:
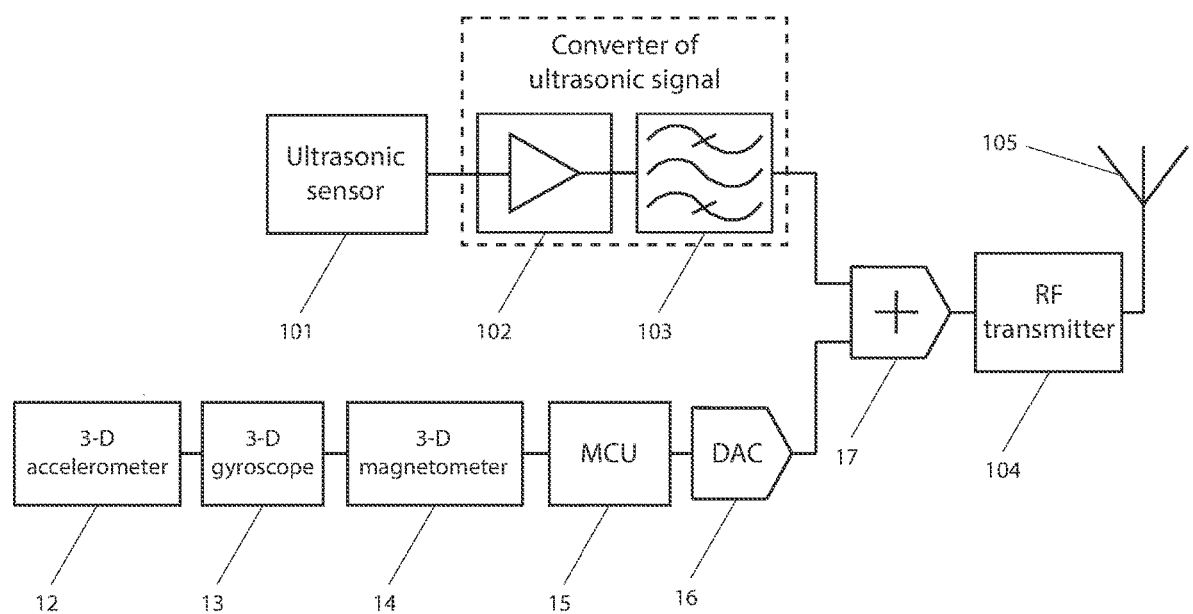
FIG. 10 is a schematic block diagram of the inner structure of a mobile, animal-attached ultrasonic receiving device with an integrated inertial tracking system consisting of 3D accelerometer, 3D gyroscope and 3D magnetic compass.
Figure 11:
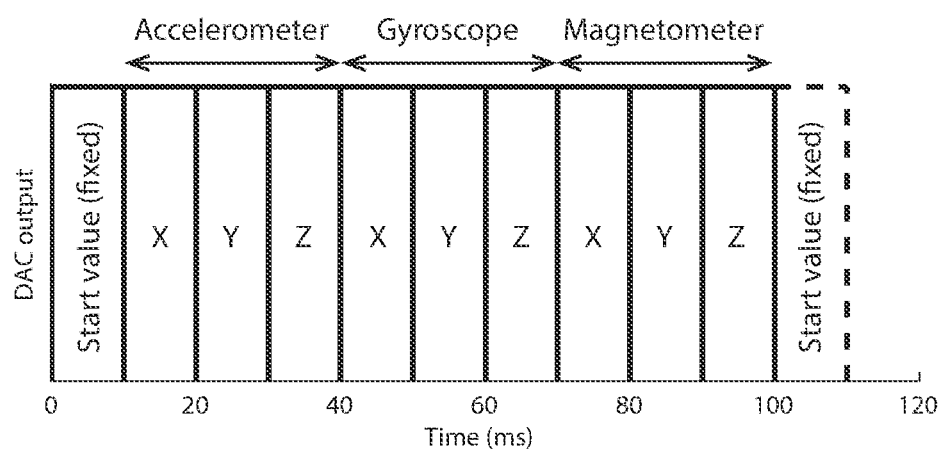
FIG. 11 shows a temporal pattern of a digital-to-analog converter (DAC) output coding information from the inertial tracking system of FIG. 10.

With reference to FIG. 10, the mobile device 1 can additionally contain a 3D accelerometer 12, a 3D gyroscope 13 and a 3D magnetometer 14. These sensors constitute a complete 9D inertial tracking system that will allow tracking of animal movements during short periods when ultrasonic signals can be temporally obscured and between ultrasonic signals to increase the temporal resolution of tracking. All 9D tracking sensors can be digital and can be connected to an MCU 15 through an I²C communication bus. MCU 15 receives information from these sensors and converts them sequentially back to analog via DAC 16. The DAC 16 can also be built inside the MCU 15. The output of DAC 16 is routed to an analog adder 17 that adds 9D short-term tracked values to the ultrasonic values and possibly to animal vocalization information received through the ultrasonic sensor 101 and the converter of ultrasonic signals 102,103. Opportunity for further separation of ultrasonic, vocalization and 9D positioning signals is given by the different frequency bands that all these signals occupy. The 9D signals can be samples with a slow sampling rate, 10 Hz for example. All nine values (accelerometer X, Y, Z; gyroscope X, Y, Z; magnetometer X, Y, Z) can be transmitted sequentially with the addition of one fixed start value (FIG. 11). Thus, DAC output values will be changed sequentially with a time step of 10 ms giving an update rate 100 Hz, which is lower than the lowest frequency of vocalization of many animals (300-500 Hz). Thus, information from 9D sensors can be mixed with audio information, if the latter does not spread to the low frequencies. Switching of DAC also can produce harmonics of higher frequencies that potentially can interfere with the animal vocalization signal, but this effect can be combated by limiting the DAC output slope. If the recording of animal vocalizations is not needed, this problem will not appear at all. The ultrasonic signal has frequencies selected especially to be higher than the animal vocalization frequencies and the DAC output rate and will not interfere with any of them. The analog adder 17 can be economically implemented on a summating operational amplifier. The mixed output of the analog adder 17 is routed to a radio frequency (RF) transmitter 104 with an integrated antenna 105. After reception of the radio signal by an RF receiver, all mixed signals can be separated by a set of digital band-pass filters for further analysis. Information that can be mixed with the ultrasonic and audio information in the above-described way is not limited to acceleration, rotation and direction of Earth's magnetic pole; signals from biological sensors of different kinds also can be added, if needed.

Figure 12:
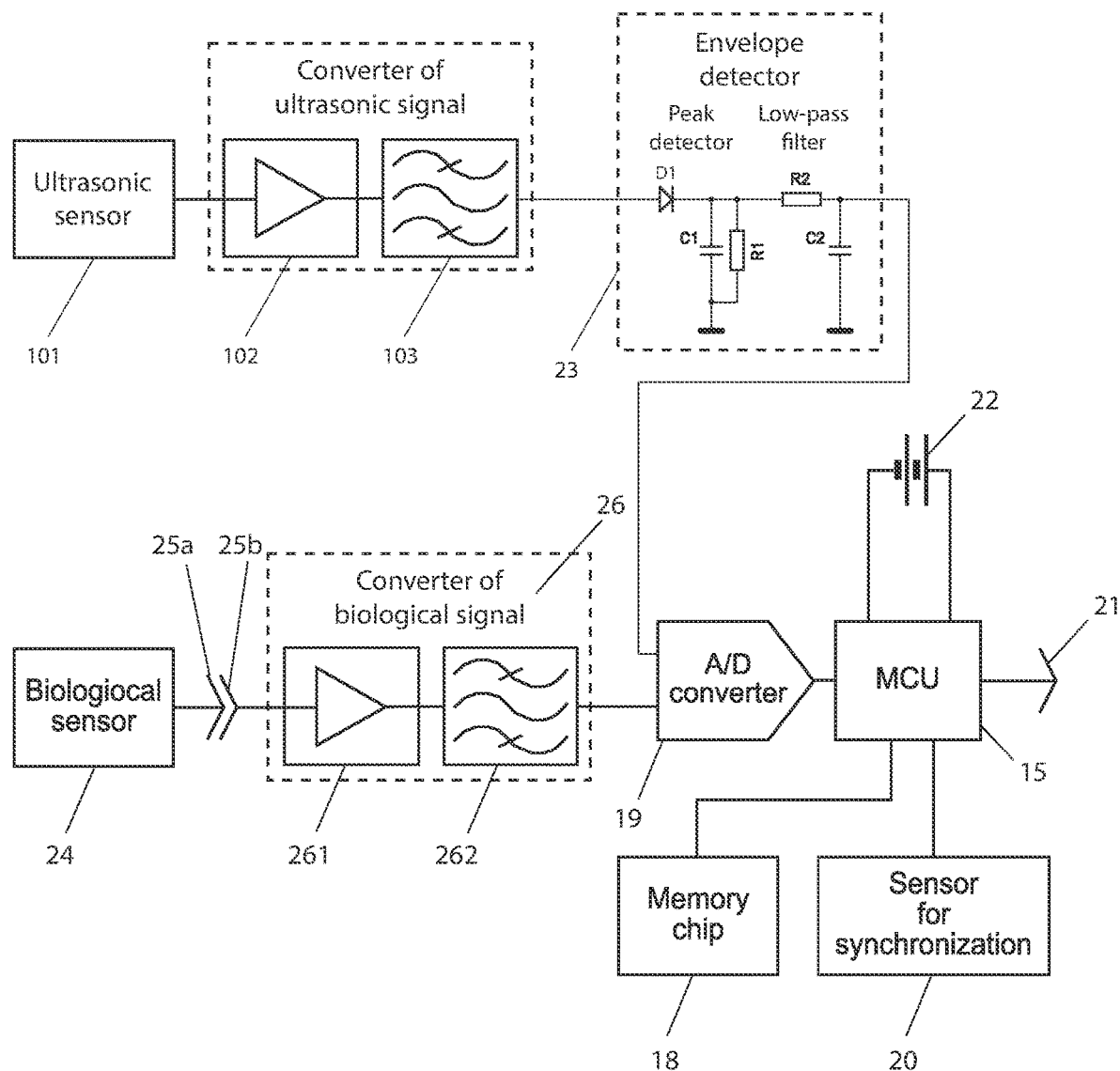
FIG. 12 is a schematic block diagram of the mobile, animal-attached ultrasonic receiving device with digitization and local storage of information about ultrasonic and IR signals and signals from biological sensors in the mobile device.

In the third embodiment, with reference to FIG. 12, the mobile device 1 depicted in FIG. 5., instead of on-line transmission of ultrasonic information to the stationary data acquisition station, stores data locally in an on-board memory chip 18. Like in the previous embodiments, the mobile device 1 includes an ultrasonic sensor 101 and convertor of ultrasonic signals 102-103. However, instead of wireless transmission of the original ultrasonic signal, the signal is digitized by an ADC 19 under control of the MCU 15. The MCU stores received information about ultrasonic signals in the on-board memory 18 and can be connected to a sensor for synchronization 20 (e.g., an IR sensor). The mobile module is also equipped with a connector 21 for data downloading after recording sessions. The unit module includes a power source 22 that provides power for all schematics. While ultrasonic oscillations are fast, their direct digitization by ADC 19 may be power demanding. To decrease sampling rate requirements, digitization of its envelope (contour), which does not contain such high frequencies, is suggested instead of digitization of the original ultrasonic signal. To extract an envelope of an ultrasonic packet, one can use an envelope detector 23 based on a peak detector with a discharging circuitry and a smoothing cascade after it. The simplest peak detector is based on diode D1 and capacitor C1. Discharging of the capacitor after ultrasonic peak is done through the resistor R1. For proper digitization of the falling edge of the ultrasonic packet, the rate of discharge R1 C1 should not be slower than the ultrasonic signal decay. The low-pass filter based on resistor R2 and capacitor C2 removes high-frequency, saw-like noise from the peak detector output. After this cascade, the signal can be digitized with a significantly decreased sampling rate (e.g., 10 kHz) compared to the >80 kHz digitization necessary for the original 40 kHz signal. This embodiment of the invention allows us to save significant costs because an expensive radio receiver is not needed. In addition, direct storing of signals in memory without intermediate radio transmission allows us to avoid possible contamination of signals by the noise inherent to analog data transmission. Finally, the biggest advantage of this solution is that the data rate of information transfer is not limited by the bandwidth of the radio channel. The bandwidth of modern FLASH non-volatile memory is sufficient for storing dozens of megabytes per second. Thus, a practically unlimited amount of biological data can be stored synchronously with position information. Such biological information can include neuronal activity, local field potentials of the brain, electroencephalogram (EEG), electrocardiogram (ECG), electromyogram (EMG) and other signals. To acquire, process and store these data, the mobile module includes one or several biological sensors 24, which may be connected to the module through the connector 25a-25b, and a converter of biological signals 26 including amplifier 261 and a band-pass filter 262. The output of this cascade is routed to the ADC 19, which can also be used for digitization of the data from the ultrasonic positioning sensor 101.

Normal animal behavior should not be disturbed by the ultrasonic tracking system. This means that the ultrasonic signals of the system should not be heard by the animal under any circumstances. The ultrasonic emitter is typically energized by a burst of rectangular or sinusoidal pulses of equal amplitude. In other words, the envelope of such a signal is a rectangle, as shown in FIG. 13A. An example of the burst shaped by a rectangular envelope consisting of 16 sinusoidal, 40 kHz cycles is shown in FIG. 13B. The power spectrum of this signal is also shown in FIG. 13B. The spectrum is normalized to have 0 dB at its peak at 40 kHz. The spectrum has very notable leakage in the frequency band of animal heading. In the frequencies below 10 kHz, the signal attenuates only by 27.6 dB. Taking into account that the power of the main spectral peak can be 100 dB (at 1 m) relative to the standard hearing threshold and that the transducer used for conversion of the electrical signal to the acoustical signal has negligible oscillatory properties (i.e., it does not change the shape of the signal), the power of the signal in the frequency band of animal hearing will be 72.4 dB. Such a signal definitely will be heard by many animal species; thus, it is not animal friendly. For this reason, the standard way of energizing an emitter via a signal with rectangular envelope cannot be used with animals. Of course, one can decrease the power of the ultrasonic emitter, making it below 27 dB. However, such low intensity will be impractical because it will strongly limit the distances at which the animals can be tracked.

To decrease the influence of the ultrasonic signal on the animals and preserve reasonably high signal intensity, we propose to limit the first derivative of the signal envelope by the equation |dE/dt|<A/T at each time point of the envelope, wherein E(t) is the envelope curve, t is time, A is the maximum amplitude of the ultrasonic signal and T is the period of the base frequency of the ultrasonic signal. The signal envelope satisfying this condition is shown in FIG. 13D. The ultrasonic signal shaped by this envelope is presented in FIG. 13E, and the power spectrum of this signal is given in FIG. 13D. The proposed shaping of the ultrasonic signal strongly decreases the spread of the signal into the lower frequencies of animal hearing. For example, attenuation in the frequency band below 10 kHz is 46.4 dB, that is, 18.8 dB more than with the standard rectangular window. Such attenuation already permits usage of moderate intensities of ultrasonic signals that will not be heard by animals. For example, if the emitter produces a 45 dB ultrasonic signal (relative to standard hearing level), the leakage into the frequency band of animal hearing below 10 kHz will have an intensity of −1.4 dB—that is, it will be below the level of human hearing, and it will not be heard by the majority of animal species.

A similar result can be obtained by limiting the second derivative of the signal envelope. This is proposed in the alternative embodiment of the invention. The signal envelope with a limited second derivative by equation $|d^2E/dt^2|<A/T^2$ is shown in FIG. 13G. All abbreviations are as previously defined. The ultrasonic signal shaped by this envelope is presented in FIG. 13H, and the power spectrum of this signal in FIG. 13I. Like in the previous embodiment, significant (45.3 dB) signal attenuation in low (<10 kHz) frequencies permits exploitation of ultrasonic signals with moderate (≤45 dB) intensities for animal tracking without affecting animal behavior.

The above given estimations were done with the assumption that the transducer transforming the electrical signal to the acoustic does not change the shape of the signal. The wideband ultrasonic emitters used for scientific research in acoustics indeed perform very close to this assumption. However, many common-purpose ultrasonic emitters are especially constructed to magnify oscillations at a particular frequency. As a result, they have significant resonating properties at the given frequency. Their quality factor, or Q factor, defined as $$Q \stackrel{def}{=} 2\pi \times \frac{\text{Energy stored}}{\text{Energy dissipated per cycle}}$$

can be about 50. When such an emitter is energized by a burst, shown in FIG. 14A, it will generate an ultrasonic output shown in FIG. 14C. The power spectrum of this ultrasonic signal is shown in FIG. 14D. As one can see, the resonating emitter itself attenuates oscillations in the low-frequency range quite effectively. If a non-resonating emitter had an attenuation of oscillation 27.6 dB below 10 kHz (FIG. 13C), the resonating emitter with Q=50 would attenuate this frequency range by 61.4 dB (i.e., more effectively by 36.5 dB). The ultrasonic pulses of moderate (≤61 dB) intensities will not be heard by the animals. However, the typical output power of an ultrasonic emitter is 100 dB relative to standard hearing threshold (at 1 m distance). The output of such an emitter will exceed the standard hearing threshold by 38.6 dB and will be heard by humans and possibly by animals (if one supposes that they have hearing of similar quality). Thus, such ultrasonic emitters can disturb the animal in a quite environment and cannot be used in a behavioral experiment for this reason.

Designing an animal-friendly method of ultrasonic tracking is an aspect of the current invention. One can note that the majority of low-frequency disturbances in FIG. 14D are produced by sharp signal onset (switching on) and offset (switching of) of the ultrasonic emitter (FIG. 14C). FIGS. 15A-15D show the energizing signal with its spectrum as well as the output ultrasonic signal with its spectrum as proposed in the current invention. To decrease spreading of the power in the side bands, especially in the frequencies below 10 kHz of animal hearing, the amplitude of the energizing signal is decreased toward the ends of the burst (FIG. 15A). To get this decrease, the amplitude of the sinusoidal wave has been modulated by the window function (envelope)

$$A(t) = \sin^\alpha\left(\frac{\pi t}{T}\right),$$

where α is a positive constant (in this particular case, α=4), π is the mathematical constant 3.14159 . . . , T is the duration of ultrasonic burst (0.4 ms) and time t is calculated from the start of ultrasonic burst, t ∈ [0,T]. Such modulation leads to a 78.7 dB power decrease in frequencies below 10 kHz in the spectrum of this energizing signal (compare FIG. 15B with FIG. 14B). The ultrasonic signal generated by the resonating (Q=50) transducer with such modulated energizing is shown in FIG. 15C, and its power spectrum in FIG. 15D. Essentially, the maximal power of the signal in frequencies below 10 kHz decreased from −61.4 dB down to −140.1 dB (by a substantial 78.7 dB). Thus, if the output power of the ultrasonic emitter is 100 dB (at 1 m), the intensity of sound in the hearing range below 10 kHz will be 40.1 dB below the human hearing threshold. Thus, such a signal cannot be detected by humans and possibly by many animals. Such a type of ultrasonic signal can be classified as animal friendly and can be used in animal experiments. Moreover, effective attenuation of low frequencies allows us to increase the power of the ultrasonic emitter, thereby increasing the effective range of animal tracking. Increasing power by 40 dB from 100 dB to 140 dB will increase the effective tracking range 100× without increasing the sensitivity of the receiver. Notably, some animals, like rodents, have a hearing range that propagates into the human ultrasonic range. The described approach is also applicable to these animals, but the ultrasonic frequency of the tracking system should be increased accordingly from standard 40 kHz to higher values, say 250 kHz.

A family of window functions with different parameters a is shown in FIG. 16A. Parameter α=0 corresponds to a rectangular window (i.e., no modulation), parameter α=1 corresponds to a cosine window and parameter α=2 corresponds to a Hanning (or Hann) window. Attenuation of spectral power in low frequencies (<10 kHz) grows with the parameter α (FIG. 16B). However, the width of the peak at 40 kHz also increases (FIG. 16B), and the maximal ultrasonic amplitude at the emitter decreases (FIG. 16C). The last two phenomena are not desired. Thus, an optimal value of a should be chosen to keep the attenuation in low frequencies at a desirable level (−140.1 dB) and simultaneously not dump the amplitude below some threshold (45.92% from non-modulated burst) to keep the range of animal tracking reasonably large. Alphas of around 4 seem to satisfy both requirements. To preserve generality, and taking into account the limited accuracy of measurements and possible disturbances and non-linearity in the signal paths, we described the envelope by the function $$E(t) = B \cdot \left( \left( \sin^\alpha \left( \frac{\pi t}{T} \right) + \delta(t) \right) \right),$$

where E(t) is the instantaneous amplitude of voltage or current at the ultrasonic emitter, t is time counted from the start of the sound envelope, B is the maximum amplitude of voltage or current at the ultrasonic emitter, $\alpha$ is a positive constant, $\pi$ is the mathematical constant 3.14159 . . . , T is duration of the envelope and $\delta(t)$ is any function of time or random noise with an absolute value smaller 0.25 (i.e., $|\delta(t)|<0.25$) for any t from the interval [0, T].

The required modulated energizing signal shown in FIG. 15A can be easily generated by a DAC under microprocessor (MCU) control (FIG. 17). However, DAC output is usually not strong enough to drive an ultrasonic emitter T1 directly. Thus, the signal should be amplified by the operational amplifier OA1 with amplification coefficient determined by the ratio of resistors (R2+R1)/R1. A typical operational amplifier works with a power supply of ±15 V. However, an ultrasonic emitter may require voltages up to 60 V peak-to peak. To achieve such a voltage span, the second amplifier OA2 can be bridged with the first amplifier in a counter-phase way to double the effective amplitude on the emitter T1. Resistors R3 and R4 should be equal. Optional resistors R5 and R6 typically have values of 51 Ohm. They are introduced to decrease the capacitive load on the outputs of the amplifiers if they drive ultrasonic emitter T1 though a long coaxial cable. The signal "Enable" that is routed from the microcontroller to the amplifiers activates the amplifiers only when signal transmission is needed. This decreases the power consumption of the circuitry.

The ultrasonic emitter also can be asymmetrically driven—for example, only by the positive half of a sinusoidal wave (FIG. 18A). The spectrum of energizing signal is shown in FIG. 18B. The benefit of this approach is the simplicity of its schematic realization. One input of the ultrasonic emitter can be connected to a positive rail of the power supply, and another can be driven down by an NPN transistor in open collector configuration or by an N-MOSFET transistor with its drain attached to the ultrasonic emitter, possibly through a current-limiting resistor. The base of the NPN transistor or the gate of the N-MOSFET can be controlled by an MCU through a DAC or directly by a digital pin using the pulse-width-modulation (PWM) approach. However, an asymmetrical drive will produce only half of the ultrasonic amplitude compared to a symmetrical drive (FIG. 18C). Also, the spectrum of ultrasonic signal (FIG. 18D) will have noise in a low-frequency (<10 kHz) band at the level −31.9.0 dB. This is 108.2 dB larger than in the case of the symmetrical drive (−140.1 dB, FIG. 15D) and is 68.1 dB above the human hearing threshold, if we assume that the ultrasonic emitter generates a 100 dB signal. The asymmetrical drive also can be used for animal tracking—for example, in cases when natural background noise is substantial (68 dB) and masks the noise produced by the ultrasonic tracking system. It is not recommended in all other cases.

Some ultrasonic emitters require high voltage that cannot be provided by operational amplifiers in the scheme of FIG. 17. In such cases, a bridged operational amplifier can be replaced with a bipolar or MOSFET transistor bridge driver. An example of a MOSFET transistor driver is shown in FIG. 19. The bridge driver is controlled by two digital outputs, OUT1 and OUT2, of a microcontroller (MCU). When OUT1 has a high level, transistors NPN1, PMOSFET1 and NMOSFET2 are closed, and current passes through the ultrasonic emitter T1 and the resistors R1 and R4. When OUT2 has a high level, transistors NPN2, PMOSFET2 and NMOSFET1 are closed, and current passes through the ultrasonic emitter T1 and resistors R2 and R3. By activating OUT1 and OUT2 sequentially, it is possible to generate a biphasic rectangular wave driving the emitter T1. Resistors R1, R2, R3 and R4 are optional. They are introduced to limit peak current in the cascade. In a practical realization of the circuitry, the lines OUT1 and OUT2 should have pulling to the ground resistors to eliminate floating of these lines during powering on; these resistors are not shown for simplicity. A dumped sine wave used for animal-friendly, noise-free ultrasonic signal generation can be approximated by a sequence of pulses with different duration (PWM). Such approximation is shown in FIG. 20. In a sequence of rectangular pulses, the duration of each pulse is proportional to the amplitude of the sinusoidal signal in the current time point. The lowest chart in FIG. 20 shows the output of the ultrasonic emitter with Q factor 50. An advantage of the method of ultrasonic wave generation described in FIGS. 19, 20 is low power dissipation in the elements of this cascade: It is the most power-saving approach of ultrasound generation. The PWM signal at the emitter is shown in FIG. 21A. The spectrum of this signal is represented in FIG. 21B. It is interesting to note that such a PWM signal has strong (139.7 dB) attenuation of power in low frequencies (<10 kHz). The attenuation is almost as good as in the case of the original dumped sinusoidal signal in FIG. 15B (140.1 dB). A small decrease in attenuation (0.4 dB) is compensated by an increased 1.53× amplitude of PWM signal compared to the dumped sine wave drive of equal maximal amplitude. This allows us additionally to increase the tracking distance by 1.53× without increasing voltage at the signal generator or the receiver sensitivity. The spectrum of ultrasonic output is shown in FIG. 21D. Attenuation by 139.7 dB will allow us to use a strong (≤140 dB) emitter without disrupting normal animal behavior by extraneous sound and with minimal energy losses in the transmitting cascade.

The discussed ultrasonic animal tracking has two disadvantages. First, sound amplitude attenuates rapidly with distance from the source (~1/x, where x is distance). Thus, the ultrasonic mobile receiver should have a large dynamic input range to provide reliable tracking at different distances from the ultrasonic emitter; this requirement can increase the complexity of the receiver. Second, limited sound speed in the air can limit the maximal animal position sampling rate. In the simplest realization, echoes from preceding ultrasonic signals should be attenuated at the moment the current ultrasonic packet is received to avoid unwanted interferences. One can generate a sequence of different ultrasonic signals of a special structure that will allow their reconstruction after overlapping, but this again can lead to an undesirable increase in system complexity.

Both disadvantages of ultrasonic tracking are eliminated in the optical tracking system described further. The main idea of optical tracking in the current invention is illustrated by reading the position of a beetle 2 on a runway 27 in FIG. 22. An ultra-miniature mobile device 1 is attached to beetle 2. The mobile device incorporates an IR receiver and an RF transmitter. When an IR beam is detected by the IR receiver, information about this event is broadcasted by the RF transmitter. The stationary RF receiver 7 receives information via antenna 6 and transfers it to a personal computer 9. The computer 9 has a built-in clock system that allows it to detect precisely the TOA of the light beam to the mobile device 1. The wavelength of the light beam should not necessarily be in the IR part of the spectrum. The single requirement is that this light beam should not interfere with the normal animal behavior that is studied. For this reason, one should select a wavelength and intensity of light invisible to the investigated animal. The majority of animals, similar to humans, do not see in the IR part of the spectrum. Thus, the IR light is selected for all examples of the current invention specification. Alternatively, for the majority of animals, an ultraviolet light that is invisible to them can be used with the same success. Thus, the invention does not claim to explicitly restrict possible wavelengths, but rather to specify that the light should not be visible by the animals and should not disturb their usual behavior.

The mobile device 1 can receive IR signals from two sources: IR emitter 11, producing strobe light pulse to illuminate the animal position measurement field, and a localized source of anisotropic light beam called the "optical transmitter," which consists of an IR laser 301 emitting a laser beam 306, a rotating mirror 302 and a motor 303 for the rotating mirror 302. The rotating mirror 302 can be substituted with a rotating reflecting prism. The typical frequency of motor rotation is 60 Hz.

The mirror 302 is rotated with angular velocity $\omega$ and is oriented in a way that the laser beam 306a reflected from it scans along the runway where the animal is located. When this light beam 306a intersects with the mobile device 1, the computer 9 receives information about this event. Animal position x on the runway can be computed from the declination angle $\varphi$ of the light beam from the horizontal plane as $x=h\cdot\cos(\varphi)$, where h is the distance from the rotating mirror 302 to the runway 27. To do such computation, information about the phase of the rotating mirror 302 should be available to the computer 9. The easiest way to measure the phase of rotation is to detect the time when the reflected light beam 306a has a particular (e.g., horizontal) orientation by means of a stationary IR sensor 304 with a known location. The IR sensor 304 is considered an integrated part of the optical transmitter. The sensor can play a role as an IR photodiode or a phototransistor. The signal from IR sensor 304 goes to the converter of IR signals consisting of amplifier 501 and band-pass filter 502. The amplifier 501 is needed to amplify the weak signal from the photodiode of the stationary IR sensor 304. The band-pass filter 502 is needed to separate useful signal and suppress background noise. The output of the converter of IR signals can be directed to the IR emitter 11 to send an IR pulse to the mobile device 1 at the moment when the reflected light beam 306a passers the IR sensor 304, or when it has a horizontal orientation (because we positioned IR sensor 304 in this way). Then the computer 9 will receive two events: one from direct illumination of the mobile device by the IR laser 301 through the mirror 302, and the second from the IR emitter 11. To simplify discrimination of two signals by the computer, we propose to make these signals slightly different. In particular, we suggest elongating the pulse from the converter of IR signals 501, 502 using the pulse extender 503.

The pulse extender can be constructed on the basis of a simple RC-delay circuit, the timer chip NE555 or by other means. Having received two sequential pulses, the computer 9 can compare their duration and discriminate the extended pulse produced by the IR emitter 11 from the pulses from the laser 301. The schematic temporal diagram of pulses in the system of FIG. 22 is shown in FIG. 23. The stationary sensor 304 detects the pulses at time points S and S'. The strobe pulses produced by the IR emitter 11 rise synchronously (or with a negligible delay) with the stationary sensor pulses at time points S and S'. However, the strobe pulses are elongated by the pulse extender 503. The pulses received by the IR receiver of the mobile device 1 are shown at the bottom in FIG. 23. The period of mirror rotation T can be precisely measured as the difference T=S'−S.

Thus, the phase $\varphi$ can be computed as $$\varphi = 2\pi\frac{\tau}{T},$$

$\tau=L-S$, where L is the time at which the scanning beam from the laser 301 is detected by the mobile device 1. Consequently, the mobile device's 1 location and the animal 2 location associated with it will be computed as $$x = h\cdot\cos\left(2\pi\frac{L-S}{S'-S}\right).$$

As one can see, this method effectively converts difficult to measure animal location to easy to handle and transmit time intervals. In some ways, this approach is similar to the measurement of TOA of ultrasonic waves described above. However, the main advantage of the optical system is that the angular speed $\omega$ and, consequently, the animal position scanning rate, is freely selectable. Thus, it is possible to select an angular speed $\omega$ sufficient for the desired temporal resolution of animal tracking and, simultaneously, to keep angular speed moderate for economical realization of electrical circuitry from commonly available parts.

An optical system for two-dimensional tracking of an animal on the plane is shown in FIG. 24. Similar to the single-dimensional tracking system of FIG. 22, the mobile device 1 identical to the mobile device in FIG. 22 is attached to the tracked animal 2 (a beetle). As before, the mobile device 1 contains IR receiver and RF transmitter broadcasting information to the RF receiver 7 with the antenna 6. The final recipient of this information is the computer 9. However, for two-dimensional tracking, two optical transmitters that emit anisotropic light beams are used. This pair of 1D transmitters is called the 2D optical transmitter 300. The first 1D transmitter consists of an IR laser 301 emitting a laser beam 306, a rotating mirror 302, motor 303 and IR sensor 304. The second optical transmitter includes an IR laser 311 emitting a laser beam 316, a rotating mirror 312, motor 313 and IR sensor 314. In addition, each of the optical transmitters incorporates cylindrical lenses 305 and 315, respectively. These lenses convert narrow parallel beams 306 and 316 of the lasers 301 and 311 into planar light beams 300-1 and 300-2 to scan the animal position measurement field in two orthogonal directions x and y. These cylindrical lenses 305 and 315 are attached to mirrors 302 and 312, respectively, and rotate together with them. Alternatively, instead of using flat rotating mirrors 302 and 312 with cylindrical lenses 305 and 315, use of curved mirrors to produce planar light beams 300-1 and 300-2 is possible. Similar to the single-dimension system of FIG. 22, two built-in stationary IR sensors 304 and 314 detect the time of reflection of rotating mirrors 302 and 312 in the horizontal direction. The controlling module 500 receives signals from IR sensors 304 and 314 and emits IR pulses by IR emitter 11 when these IR sensors are eliminated by the corresponding rotating laser beams 300-1 and 300-2. The controlling module 500 also includes the pulse-extension circuitry described earlier, which extends the duration of pulses given by IR sensors 304 and 314. However, to simplify data analysis, the pulse-extension circuitry extends the pulse from the second stationary IR sensor 314 more than that from the first IR stationary sensor 304 (see FIG. 25).

In addition, the task of the controlling module 500 is to introduce an approximately 180° phase shift between rotation of mirrors 302 and 312. This phase shift is not used in position calculation; it is needed to avoid temporal overlap in the scanning of the animal position measurement field by lasers 301 and 311. Similar to FIG. 23, the two-dimensional position of the mobile device 1 is determined from the time differences in pulses onsets (FIG. 25):

$$x = h \cdot \cos\left(2\pi \frac{L1 - S1}{S1' - S1}\right) \text{ and } y = h \cdot \cos\left(2\pi \frac{L2 - S2}{S2' - S2}\right).$$

The pulse S2' is not displayed in FIG. 25. It follows S2 similar to the way that S1' follows S1. Note that axes of rotation of mirrors 302 and 312 need not be orthogonal; they also can lie at different altitudes h from the animal position measurement plane. The single requirement is that these axes should not be collinear.

The planar light beam is, in fact, a theoretical abstraction. There is always some divergence of the beam due to the wave nature of light (i.e., the light beam is indeed never planar). To account for the divergence phenomenon and for other non-idealities, the margins of acceptable spreading of the light beam are postulated in the current specification. The light beam is considered planar if 90% of its power is concentrated in a narrow angle ±10° from the plane. FIG. 26 illustrates this definition. The planar light beam is emitted by the optical transmitter 320, symbolically drawn as a cube. The ideal planar beam should be concentrated in a plane 29 with a normal 30. The optical transmitter 320 rotates the planar beam with the center of rotation 320. The instantaneous tangential speed of the planar beam 29 coincides with the normal 30. The grey sectors 31 and 32 denote the ±10° margin of deviation from the plane 29. The distribution of light intensity is approximated by Gaussian function 33 in FIG. 26. Let us determine the thickness of a light beam as the distance through the beam in the direction that gives the smallest value from all possible directions. The thickness of the planar beam should not exceed the maximal size (length) X of the tracked animal 2 to provide accuracy sufficient for recognition of relative positions of several simultaneously tracked animals.

One can note that the slope of the light intensity curve 33 in FIG. 26, rather than the total thickness of the planar light beam, determines the temporal accuracy of the rising edge of the pulse used for animal position calculation. Thus, the edges of the light beam should be sharp, but it is not necessary for the light beam itself to be thin or planar. FIG. 27 depicts another realization of the light beam: The localized optical transmitter 320 radially emits light in the left hemisphere 34 only, leaving the opposite hemisphere dark (not shown). The transverse gradient of light intensity (i.e., the gradient in the plane orthogonal to the beam propagation path) in such a beam is zero everywhere except the greyed plane 35. Thus, we can call this a beam with planar gradient distribution, or just a "planar gradient" (although the transverse gradient itself is orthogonal to this plane, collinear with the vector 36). To account for natural beam divergence, we shall consider the transverse gradient planar if 90% of light intensity decline falls within a ±5° angle from the plane (FIG. 27). The light intensity decline profile 37 is approximated by a left-right flipped integral of Gaussian function. If we look from the side of another non-illuminated hemisphere, there will be a 90% increase in light intensity at the border of the two hemispheres. The light intensity increase profile 38 is approximated by an integral of Gaussian function. In this example, the profiles of the decline 37 and the increase 38 in light intensity are described by the same function, but these profiles also can have different shapes. Furthermore, in the scope of the current invention, there can be several planes with non-zero transverse gradients—planes can be parallel to each other or intersect with each other. For example, the segments of two planes with the planar distribution of the gradient can constitute a configuration as grey sectors 31 and 32 in FIG. 26. To achieve the same level of accuracy as before in the vicinity of the animal, we consider the transverse gradient as planar if 90% of light intensity change is observed at half the length of the tracked animal 2 (FIG. 27).

FIG. 28 shows an optical three-dimensional tracking system for monitoring of a flying animal, for example, a dragonfly. As in the previous embodiments of the invention in FIGS. 22 and 24, the dragonfly carries the mobile device that includes the IR receiver. However, instead of the previously used radio transmitter, the device incorporates local memory for storing events (light beam detections) and a clock or a timer for assigning time stamps to detected events. As before in FIG. 24, the stationary part is represented by the 2D optical transmitter 300 comprising two 1D optical transmitters, but to implement tracking in the third dimension, an additional optical transmitter 320, similar to other two, is added. It consists of the laser 321, rotating mirror 322, motor 323, IR sensor 324 and cylindrical lens 325. At least one optical transmitter should be spatially separated from the other two for 3D tracking. In this case, the third transmitter is separated from other two by distance D (see FIG. 28). The following computation of animal position assumes for simplicity that mirrors 302 and 312 are so close to each other that the distance between them can be neglected. As before, the common controlling module 500 receives signals from three stationary IR sensors 304, 314 and 324, emits the strobe light pulse to illuminate the animal position measurement field by IR emitter 11 and finally checks and, if necessary, corrects the phase shifts between rotating mirrors 302, 312 and 322. Note that cylindrical lenses 305, 315 and 325 are fixed to the corresponding mirrors and rotate with them. The relative phases of the mirrors are set to allow three 1D optical transmitters to scan the animal position measurement field by the planar light beams 300-1, 300-2 and 320-1 sequentially without temporal overlapping of the scans. To simplify temporal separation of the scans in certain environments, the controlling module 500 can sequentially switch off and then on IR lasers 301, 311 and 321 emitting laser beams 306, 316 and 326, respectively.

The schematic temporal diagram of pulses in the system of FIG. 28 is shown in FIG. 29. The time period corresponding to two revolutions of the mirrors is shown. The first pair of 1D optical transmitters work as before in FIG. 27, with the exception of switching off their emitting lasers on every second revolution to give time for the third optical 1D transmitter 320 to make a scan. In addition, the lasers are switched off during half of the revolution, during which time they emit light just to preserve energy and extend the lasers' lifespan. The lasers also are kept on during small time periods around detection times of corresponding stationary IR sensors for precise measurement of revolution periods T1, T2 and T3. Similar to the previously described embodiment, different strobe pulses are extended by the pulse extending circuitry 503 to different extents to help to differentiate the pulses. The state of the laser (ON or OFF) is also coded by the length of the corresponding strobe pulse. The controlling module 500 introduces a small phase shift between mirrors 302 and 322 to avoid overlapping of corresponding strobe pulses in FIG. 29.

To compute animal position in Cartesian coordinates, let us denote the angles at which scanning beams intersect with the animal as $\varphi_1$, $\varphi_2$ and $\varphi_3$ for optical transmitters 1, 2 and 3, respectively. All angles are counted from the horizon, as shown in FIG. 22. These angles are determined from time intervals $\tau_1$, $\tau_2$ and $\tau_3$ in FIG. 29, similar to FIG. 25:

$$\varphi_1 = 2\pi \frac{L1 - S1}{S1' - S1};$$
$$\varphi_2 = 2\pi \frac{L2 - S2}{S12' - S2};$$
$$\varphi_3 = 2\pi \frac{L3 - S3}{S3' - S3}.$$

The angles $\varphi_1$, $\varphi_2$ and $\varphi_3$ determine animal position relative to the optical transmitters in 3D space. The specially chosen configuration of transmitters in FIG. 28 allows recalculation of angles $\varphi_1$, $\varphi_2$ and $\varphi_3$ to more common Cartesian coordinates x, y and z, shown in FIG. 28, using simple trigonometric relations:

$$\tan(\varphi_1) = \frac{h-z}{x};$$
$$\tan(\varphi_2) = \frac{h-z}{y};$$
$$\tan(\varphi_3) = \frac{h-z}{x+D}.$$

After simple algebraic transformations, we get the following equations for Cartesian coordinates of the animal:

$$x = D\frac{\tan(\varphi_3)}{\tan(\varphi_1) - \tan(\varphi_3)};$$
$$y = D\frac{\tan(\varphi_1) \cdot \tan(\varphi_3)}{\tan(\varphi_2) \cdot [\tan(\varphi_1) - \tan(\varphi_3)]};$$
$$z = h - D\frac{\tan(\varphi_1) \cdot \tan(\varphi_3)}{\tan(\varphi_1) - \tan(\varphi_3)}.$$

To study social interactions in birds, one needs to track several animals simultaneously in 3D space (FIG. 30). The optical tracking approach shown in FIG. 28 is also applicable to multiple animals. However, optical tracking needs direct visibility between the IR sensor of the mobile device and at least three 1D optical transmitters, shown in FIG. 28, or if we aggregate 1D optical transmitters in 2D optical transmitters, from one pair of 2D optical transmitters symbolically shown by cubes 300, 300a and 300b in FIG. 30. Thus, each 2D optical transmitter emits two planar laser beams: 300-1, 300-2, 300a-1, 300a-2, 300b-1 and 300b-2. These planar beams scan the animal position measurement field sequentially. Each 2D optical transmitter is complemented by corresponding emitter 11, 11a or 11b. These strobe pulse emitters are synchronously activated by the controlling module 500. In fact, one strobe pulse emitter might be sufficient because illumination of the entire animal position measurement field produces strong reflections that are sufficient for activating the IR sensors of the mobile device 1, even in the absence of direct visibility from the emitter to the sensor if it is obscured by, for example, another animal. Contrary to strobe pulse emitters, direct visibility of at least two 2D optical transmitters is essential.

Doubling the number of optical transmitters in FIG. 30 comparative to FIG. 28 should increase the robustness of tracking multiple animals, thereby decreasing the probability of the event that an insufficient number of 2D optical transmitters are in direct visibility (i.e., no transmitters or only one transmitter). The scanning rate of each 2D optical transmitter should be decreased to avoid temporal overlapping of light beams from different optical transmitters (if the angular speed of scanning is preserved). A simple way to realize this is a sequential switching on and off of the lasers shown in the schematic diagram FIG. 31. Here, contrary to the diagram in FIG. 29, only a strobe pulse associated with the active transmitter is generated to avoid overlapping of such pulses. While the strobe pulse emitters 11, 11a and 11b are activated only every third revolution of the selected rotated mirror, the three periods depicted in FIG. 31 are needed to measure the average angular velocity of the mirror by the mobile devices. Contrary to the mobile devices, the signals from the stationary IR sensors incorporated in 2D optical transmitters 300, 300a and 300b go through separate electrical lines to the controlling module 500, and all of them can be used to correct the phases of the rotating mirrors if needed. As before, the strobe pulses associated with the different scans can have different durations to simplify their classification after reception.

It is important to note that in the configuration FIG. 30, multiple redundant optical transmitters do not reduce the resulting animal position sampling rate compared to the minimal configuration in FIG. 28. In the configuration FIG. 30, each transmitter scans less often, but the total rate of scans remains the same. At the same time, the robustness of tracking in this configuration is drastically increased because in practice the chance of occasional simultaneous occlusion of two optical paths (or more) from three is much smaller than the chance of occlusion of any one or both from the two paths to optical transmitters 300 and 320 in FIG. 28: If the probability of occasional occlusion of one optical path is p, the probability of having one or two passes occluded (i.e., tracking failure) is $2p(1-p)+p^2 \approx 2p$ if p is small. The probability of having two (or more) paths occluded from three possible is $3p^2(1-p)+p^3 \approx 3p^2$ if p is small. If we assume p=0.01, we see that adding one additional 2D optical transmitter (FIG. 30) to the minimal configuration of two 2D transmitters decreases the number of non-recognized animal positions by the factor $$\frac{2p}{4p^3} = 5000$$

Adding the fourth 2D optical transmitter will lead to the probability of tracking failure of $4p^3(1-p)+p^4 \approx 4p^3$ if p is small. Thus, a system with four 2D optical transmitters will decrease the number of non-recognized animal positions by the factor $$\frac{2p}{3p^2} \approx 66.6.$$

compared to the minimalistic system with two 2D optical transmitters. Further increase in the number of 2D optical transmitters in the system will increase the robustness of the tracking, but with a smaller performance gain because in the system with multiple transmitters occlusions of different paths can no longer be treated as independent events.

Positioning of several spatially separated optical transmitters within the animal position measurement field is a good solution for tracking if the geometrical constraints of the environment allow it. However, sometimes this may be impossible or problematic. In such cases, 3D tracking by a single compact module may be the desired solution. An additional advantage of such an approach is the absence of a need to calibrate such a system after its transportation from one place to another because all parts of the system will be permanently connected with each other inside one transportable module. Neither the discussed ultrasonic nor optical tracking systems can be encapsulated in one compact module capable of 3D tracking. However, a hybrid system presented in FIG. 32 achieves this. This solution is novel not only in the field of animal tracking, but may be a worthy addition for tracking objects of different natures in general. The system in FIG. 32 represents a combination of 2D optical transmitter with the ultrasonic emitter complementing the 2D tracking with the third dimension. The optical part of the system in FIG. 32 is identical to the 2D tracking system in FIG. 24. The ultrasonic emitter 3 is inherited from the ultrasonic tracking system in FIG. 5. The strobe pulse IR emitter 11 is common for both parts in FIG. 32.

FIG. 33 shows a schematic temporal diagram of signals in the system of FIG. 32. The controlling module 500 detects the time points of horizontal orientation of the reflected beams by the stationary IR sensors 304 and 314. At that moment, strobe pulses of different durations are emitted by the IR emitter 11. The mobile device has an IR sensor that receives the strobe pulses and scanning laser beams to compute two angles $\varphi_1$ and $\varphi_2$ from the time intervals $\tau_1$ and $\tau_2$ by the equations given for FIGS. 24, 25. In addition, when the light beam is detected by the stationary IR sensor 304 (the first in FIG. 33), the ultrasonic emitter 3 produces an ultrasonic signal that is detected by the ultrasonic receiver of the mobile device 1 with the TOA delay TOA1 (FIG. 33). The missed the third coordinate for 3D tracking can be obtained from the distance from the ultrasonic emitter to the mobile receiver computed from TOA1 and known speed of sound in the air. Assuming the proximity of two rotating mirrors 302 and 312 to be as before, positioning the ultrasonic emitter above them at altitude $h_u$ over the ground plane and placing zero of the Cartesian coordinate system at the ground plane just under these mirrors, we can get the following equations for computing the 3D position of the animal in FIG. 32:

$$\tan(\varphi_1) = \frac{h-z}{x};$$

$$\tan(\varphi_2) = \frac{h-z}{y};$$

$$(v \cdot TOA1)^2 = x^2 + y^2 + (h_u - z)^2;$$

where v is the known speed of sound in the air. Let us suppose for simplicity that the ultrasonic emitter 3 is very close to the mirrors 302 and 312, and thus $h_u$=h. Under such assumptions, we get the following final equations after simple algebraic transformations:

$$x = \frac{1}{\tan(\varphi_1)} \cdot \frac{v \cdot TOA1}{\sqrt{\frac{1}{\tan^2(\varphi_1)} + \frac{1}{\tan^2(\varphi_2)} + 1}};$$

$$y = \frac{1}{\tan(\varphi_2)} \cdot \frac{v \cdot TOA1}{\sqrt{\frac{1}{\tan^2(\varphi_1)} + \frac{1}{\tan^2(\varphi_2)} + 1}};$$

$$z = h - \frac{v \cdot TOA1}{\sqrt{\frac{1}{\tan^2(\varphi_1)} + \frac{1}{\tan^2(\varphi_2)} + 1}}.$$

These equations are exact when the center of origin of spherical ultrasonic waves generated by the ultrasonic emitter is located at the intersection of the axes of rotation of two anisotropic light beams (FIG. 34). The advantage of this geometrical arrangement is simplicity of computation of position of the mobile device. The axes of rotation of two anisotropic light beams 300-1 and 300-2 coincide with laser beams 306 and 316. These axes intersect and the ultrasonic emitter 3 is placed at their intersection. The rotating elements 302 and 305, together with motor 303 are on the same side as laser 301, relatively to the point of intersection of the axes of rotation of two anisotropic light beams 300-1 and 300-2. A group of elements 312,315 and 313 is placed on the same side as laser 311, relatively to the point of intersection of the axes of rotation of two anisotropic light beams 300-1 and 300-2. Thus, the point of intersection of the axes of rotation of two anisotropic light beams is free of any elements of optical system (including laser beams) and an ultrasonic emitter of any size and geometry can be placed at this intersection.

A typical commercially available air ultrasonic emitter (e.g. Air Ultrasonic Transducer EC4018) has the center of origin of spherical ultrasonic waves, generated by it, inside its body. Such ultrasonic emitter can be placed at the point of intersection of the axes of rotation of two anisotropic light beams only if no other material objects are there, as it was discussed above. However, it is possible to design a special ultrasonic emitter that will have the center of origin of spherical ultrasonic waves, generated by the device, outside of the body of the device. The vibrating surface of such emitter should be manufactured in the form of an inverted cone, i.e. empty cone, directed towards medium, like in a set of devices, engineered to produce a cumulative effect. All other parts of the device, other than the cone, should be insulated from the medium to avoid unnecessary interference. The emitter with the external center of origin of spherical ultrasonic waves can be placed outside of the point of intersection of the axes of rotation of two anisotropic light beams, whereas the center of origin of spherical ultrasonic waves generated by this emitter can be exactly at the point of intersection of the axes of rotation of two anisotropic light beams. The emitter of the above-mentioned type can be used together with the intersecting laser beams 306 and 316, shown in FIG. 32.

Precise optical systems are known to be sensitive to vibration. The standard ultrasonic transmitter can produce mechanical vibration with a wide spectrum shown in FIG. 14D. Some frequencies in this spectrum can have negative influence on the accuracy of optical transmitters. However, the animal-friendly ultrasonic transmitter proposed in the current invention has significantly suppressed side bands in its power spectrum (FIG. 15D). Thus, the animal-friendly ultrasonic transmitter (FIG. 15A-15D) and the ultrasonic emitter driven by pulse-width modulated signal (FIGS. 20-21D) proposed in the current invention allow to place into the same enclosure a precise optical system and a powerful ultrasonic one. With a standard ultrasonic transmitter any hybrid (optical and ultrasonic) system would have significantly decreased reliability. The increase of reliability, achieved due to animal-friendly properties of ultrasonic transmitter and its decreased interference with optical components, is important not only for animal tracking, but for tracking of any objects. An advantage of the above-mentioned side band suppression is the essentially reduced unwanted mechanical influence of the ultrasonic emitter on neighboring optical transmitters. This influence can be further decreased by the emitting of an ultrasonic signal only at a time when the rotating light beams 300-1 and 300-2 do not scan critical areas such as the animal position measurement field or stationary IR sensors 304 and 314.

The scanning rate of the ultrasonic part does not need to coincide with the scanning rate of the optical part, although this may be convenient. If the mirrors have 60 revolutions per second, the optical part of the tracking system acquires positional information at the rate 60 Hz (i.e., every 16.6 ms). In such a time interval, sound in the air propagates over 5.72 m. If the distance between the emitter and the receiver does not exceed this value, the detection of the previous ultrasonic signal will always happen before generation of the following signal, and unwanted overlapping of events will never happen (see FIG. 33 as an example). However, how do we discriminate between receptions of sequentially generated events if the animals are at distances greater than 5.72 m from the ultrasonic emitter? To resolve ambiguity of assignment of sequential ultrasonic signals to sequential strobe IR pulses, we propose to use a set of strobe pulses of different durations and a corresponding set of non-identical ultrasonic signals. In FIG. 33, such a set of strobe pulses consists of pulses of four different durations. Note the increasing strobe pulse width from the first pulse to the fourth. Two types of ultrasonic signals are used: a single-pulse signal and a double-pulse signal (FIG. 33). Two types of ultrasonic signals are temporarily locked to the IR strobe outputs and are generated sequentially. The mobile receiver, having received the set of IR strobe pulses shown and the set of ultrasonic signals, will be able to find matching pairs of synchronously generated signals up to double the distance: 2×5.72=11.44 m. If tracking at larger distances is desired, larger sets of non-identical IR and ultrasonic signals should be used.

With reference to FIG. 35, the mobile device 1 designed for the optical tracking system contains an IR sensor 101$a$ for conversion of IR signal to electrical signal, an analog conditioning circuitry for amplification 102$a$ and filtering 103$a$ of electrical signals and a radio frequency transmitter 104 with an integrated antenna 105 for radio broadcasting of information about received IR signals to a stationary data acquisition system.

The complete electrical scheme of the mobile device 1 designed for the optical tracking system is shown in FIG. 36. The IR signal is received by a photodiode D1. The photocurrent generated by the photodiode D1 in zero-bias mode is converted to voltage by an operational amplifier OA1. The output voltage of OA1 is defined by the equation U=R1·$I_p$, where $I_p$ is the current produced by the photodiode, and R1 is the resistance in the feedback of OA1. A capacitor C1 is introduced to suppress high-frequency noise. Together with the resistor R1, it forms the first-order low-pass filter with the cutoff frequency $F_1=1/(2\pi R1C1)$. The output of the operational amplifier OA1 is routed to an optional passive high-pass filter based on resistor R2 and capacitor C2 with the cutoff frequency $F_2=1/(2\pi R2C2)$. The goal of this high-pass filter is to filter out slow changes in photodiode illumination caused by animal movements that might disturb IR communication, especially if disruptive unwanted light sources (e.g., incandescent light bulbs) are present in the animal position measurement field. Another way to increase the robustness of transmission is to use modulated IR light. The carrier frequency should be relatively high, about 2 MHz, because duration of illumination of the photodiode by the planar light beam can be relatively short—about 3-5 µs. To make modulation effective, a minimum of several cycles should fall into the 3-5 µs time interval. If IR light modulation is used, the band-pass filter created by sequential cascading of the low-pass and high-pass filters should pass the carrier frequency. For example, if the carrier frequency is 2 MHz, the passing frequency interval can be 1-4 MHz. After band-pass filtration, the signal is routed to the second amplification cascade based on operational amplifier OA2 with the amplification (R3+R4)/R3. The goal of this cascade is to match the output range of the IR signal converter to the input range of the following RF transmitter and to decrease the output impedance of the IR signal converter to drive the input cascade of the RF transmitter reliably. The RF transmitter shown has a classic, single-transistor design that was discussed earlier in the description of FIG. 9. A more complicated RF transmitter may be desired to improve signal reception stability or to increase communication range. If the IR signal is modulated, an envelope-detecting cascade can be useful before RF modulation to decrease transmitted frequencies and, thus, to limit the necessary reception frequency band. The envelope detector can be diode-based like in FIG. 12 or less precise but providing some amplification as discussed in FIG. 39. The circuit is powered by the bipolar power supply BAT1 and BAT2 (1.5 V) with the capacitors C7 and C8.

With reference to FIG. 37, the mobile device 1 can additionally contain a 3D accelerometer 12, a 3D gyroscope 13 and a 3D magnetometer 14. These sensors constitute a complete 9D inertial tracking system that will allow tracking of animal movements during short periods when IR signals can be temporally obscured and between IR signals to increase temporal resolution of tracking. All 9D tracking sensors can be digital and can be connected to an MCU 15 through an I²C communication bus. The MCU 15 receives information from these sensors and converts them sequentially back to analog via DAC 16. The DAC 16 can also be built inside the MCU 15. The output of DAC 16 is routed to an analog adder 17 that adds 9D short-term tracked values to the IR values. Opportunity for further separation of IR and 9D positioning signals is given by the different frequency bands that these signals occupy.

With reference to FIG. 38, the mobile device can contain the previously described in FIG. 10 part for ultrasonic tracking, which also can be used for recording of animal vocalizations. This part consists of an ultrasonic sensor 101 that potentially can be used for recording ordinary audible frequencies and a converter of ultrasonic signals consisting of an amplifier 102 and a band-pass filter 103. While the output of the IR signal converter, the output of the ultrasonic signal converter and the output of the DAC 16 have non-overlapping frequencies (small overlapping of high-order sidebands can be neglected), these outputs can be summated by the analog adder 17 with the possibility of separation after RF transmission. If an IR signal has a 2 MHz carrier, its spectrum will be concentrated around this frequency. The frequency interval of animal vocalization for the majority of species lies in the range of 0.5-10 kHz. The frequencies in ultrasonic tracking are typically 40-250 kHz. Furthermore, 9D animal body orientation signals can be sampled with a slow sampling rate (e.g., 10 Hz) and added to the IR and ultrasonic information by the method illustrated in the previously described FIG. 11.

With reference to FIG. 39, instead of on-line transmission of the information provided by the ultrasonic and IR sensors and other data to the stationary data acquisition station, the mobile device in this embodiment stores data locally in an on-board memory chip 18. The mobile device of FIG. 39 aggregates parts of the mobile devices of the ultrasonic tracking system (FIG. 12) and the optical tracking system (FIG. 35). The majority of parts represented in FIG. 39 are identical to those of the ultrasonic tracking mobile device shown in FIG. 12. Functioning of these parts was discussed earlier. While most parts were discussed previously, we shall concentrate on their method of connection now. The IR pulses have much more abrupt edges than the ultrasonic signals discussed earlier. For this reason, they can be detected by a comparator, and the A/D converter that was desired for precise quantization of ultrasonic on- and off-sets is needed no longer. For this reason, if the IR signal is not modulated, the output of the converter of IR signals 102a, 103a can be routed directly to a comparator that is typically built in MCU 15. However, if the IR signal is modulated, the signal envelope should be detected and directed to the comparator instead of the output of the IR signal converter. One can use either a simple diode-based envelope detector 23 described earlier or a transistor-based envelope detector 23a. To rectify the signal by NPN transistor VT1, the potential of its base determined by the ratio of resistors R3 and R4 should be selected at the beginning of the linear part of the transistor transfer characteristic, when the transistor starts to conduct current (i.e., at about 0.67 V), calculated from the ground potential connected with the emitter. The capacitor C4 is needed for signal smoothing. It is charged by the pulling up resistor R6 and is discharged through the resistor R5 when the transistor VT1 is in a conducting state. The following PNP transistor VT2 with the resistor R7 is needed to invert (relatively averaged or static potential) and amplify the potential at smoothing capacitor C4. To use the non-linear properties of transistor VT1 effectively, the amplitude of the input signal to the transistor envelope detector should not be very small: a good range of amplitudes is 0.1-0.6 V. If the amplification of the final (VT2-based) amplification cascade is large enough, the comparator can be omitted, and a digital input of MCU 15 can be used to acquire information from the IR sensor.

In many behavioral experiments, an animal can interact with an experimental environment, for example, by making a nose-poke (putting its nose into a wall cavity with an optical sensor) to get a reward or by pressing a lever to avoid a negative reinforcement such as an electric shock. In other experiments, some sensory stimulation, audial or visual, can be presented to an animal for research purposes, or the animal can be recorded by a video camera for further behavioral analysis. In all such cases, precise synchronization between the data in the internal memory 18 of the mobile device 1 and the externally stored data and/or sensory stimulation provided to the animal is needed.

The desired precise synchronization can be realized by sending synchronizing signals from the stationary equipment to the mobile device 1 and storing information about these events in the local memory 18 together with the animal position data and the data from the biological sensors 24 of the mobile device 1. The IR emitter 11 can be used for broadcasting the synchronizing signal in the form of a fixed sequence of IR pulses. Different events can be coded by unique sequences. The IR sensor 101a of the mobile device 1 can receive synchronizing sequences of IR pulses and store information about them in local memory 18.

FIGS. 40-43 represent popular behavioral tests for rodents (mice, rats, etc.) and how the solutions proposed in the current invention help to automate them.

FIG. 40 shows the elevated Plus-maze, a test used for investigation of anxiety and exploratory behavior. We shall give the geometry of the Plus-maze for mice: The maze 39 has four arms, each 30 cm in length and 5 cm in width. The bottom 40 of the maze is placed 40 cm above the floor on four legs 41. Two opposing arms are protected by 15.25-cm-high walls 42. To perform behavioral testing, a rat or a mouse is placed at the junction of the four arms of the maze, facing an open arm, and entries/duration in each arm are recorded for 5 min. Other ethological parameters such as rears, head dips (when an animal looks down from the maze) and stretched-attend postures can also be observed. In spite of some constraints on visibility posed by the walls 42, the entire surface of the bottom 40 is observed from positions 300 and 320 above the ends of two protected arms (FIG. 40). This allows us to use the optical tracking approach for 3D tracking by placing a 2D optical transmitter in position 300 and an additional 1D optical transmitter in position 320. The 2D optical transmitter 300 emits planar light beams 300-1 and 300-2, and the 1D optical transmitter 320 emits the planar light beam 320-1. The planar beams are symbolically shown by divergent differently colored sectors. The IR emitter 11 for the generation of the strobe pulse for illumination of the maze 39 can be placed over the junction of the four arms. Circles with arrow heads 43 symbolically show the direction of the rotation of planar light beams 300-1, 300-2 and 320-1. Controlling module 500 controls optical transmitters 300 and 320 and IR emitter 11. The mobile device 1 comprising IR receiver and memory for data storage is attached to the head of the animal 2. The attachment to the head is not only done to simplify detection of rears and head dips, but also to collect information about brain activity via the proper biological sensors with corresponding converters of biological signals (see FIG. 18) implemented in mobile device 1.

Another methodologically similar test for studying anxiety and exploratory behavior is the elevated O-maze test shown in FIG. 41. A main part of the elevated O-maze 44 for mice is a 5.5-cm-wide ring runway 45 constructed using grey plastic. It has an outer diameter of 46 cm and is placed 40 cm above the floor on four legs 46. Two opposing 90° sectors are protected by 16-cm-high inner 47 and outer 48 walls of grey polyvinyl chloride. To make the protected sectors visible from one single position 300 where a video camera or an optical transmitter 300 for animal tracking can be placed, the side walls are slightly tilted toward the center. During an experiment, an animal is released in one of the protected sectors and is observed for 10 min. As one can note, the design of this test apparatus restricts the plurality of possible zones from which the entire area of the runway 45 can be observed. In particular, only one small zone around position 300 can be used for placing a video camera or an optical transmitter for animal tracking as in the current invention. Such geometrical constraints preclude exploiting fully ultrasonic or fully optical variants of the current invention. However, this behavioral test nicely illustrates the advantage of the proposed hybrid (ultrasonic and optical) 3D tracking solution shown in FIGS. 32, 34 and 41. In this realization, all emitting elements of the tracking system, such as 2D optical transmitter 300, IR emitter 11 and ultrasonic emitter 3, can be placed close to each other and be encapsulated in one protective enclosure to simplify use of the tracking system.

The open-field test shown in FIGS. 42, 43 is clearly the most frequently used of all behavioral tests in pharmacology and neuroscience. Despite the simplicity of the apparatus, however, open field behavior is complex. Consequently, it has been used to study a variety of behavioral traits, including general motor function, exploratory activity and anxiety-related behaviors. In the open-field test, an animal is placed in an open arena 49 for 30 min and its behavior is observed during this time. While the duration of the test is significant and a number of animals should be tested for reliable statistical comparisons, researchers prefer to test several animals in adjacent isolated open fields 49; this is shown in FIGS. 42, 43. The quadratic arenas typically have a size of 50×50 cm with walls 37 cm tall 50. The quantified behaviors usually include time of immobility, total travel distance and number of rears and stretched-attend postures. An optical tracking system containing two 2D optical transmitters 300 and 300a that emit two planar light beams each (300-1, 300-2, 300a-1, 300a-2) can be used with a maximum of two animals simultaneously (FIG. 42). One 2D optical transmitter and one 1D optical transmitter could be sufficient for this task. However, having two identical transmitting modules can decrease the system cost in case of mass production. In addition, having one additional 1D optical transmitter (inside the second 2D transmitter) allows us to check the accuracy of position measurement constantly and reject data points with excessively low accuracy during data analysis. More than two square arenas 49 with walls 50 cannot be entirely visible from two different locations, as required for 3D tracking by the optical tracking approach of the current invention. One can multiply the total number of independently working optical tracking systems, but this will increase equipment cost. An alternative solution is to use the hybrid (ultrasonic and optical) tracking system proposed in the current invention and shown in FIGS. 32, 34, 41 and 43. Having a compact aggregation of transmitting elements (2D optical transmitter 300, IR emitter 11 and ultrasonic emitter 3), one can place all of them over the center of four adjacent square open fields 49 to track four animals simultaneously (FIG. 43).

The last example of usage demonstrates that the hybrid tracking approach proposed in the current invention allows not only tracking of animals in challenging environments with geometrical restrains, or several animals in one arena, but also helps to track multiple animals in separated environments (compartments) in an economical way.

We expect that the hybrid (ultrasonic and optical) position measurement method proposed in the current invention will be useful not only for animal tracking as described in detail here, but also for position determination of a larger class of objects of different natures.

It should be understood that the foregoing relates only to preferred embodiments of the present invention and that numerous modifications or alterations may be made without departing from the spirit and scope of the invention as set forth in the appended claims.

What is claimed is:

1. A method of detecting a position of an animal, the method comprising:
attaching a mobile device to the animal, wherein the mobile device comprises an ultrasonic receiver;
emitting at least one ultrasonic signal as a pulse from at least one ultrasonic emitter at a known location at a transmission time, wherein the at least one ultrasonic signal has an envelope with a shape that is chosen with the first derivative restricted by condition $|dE/dt|<A/T$ and/or with the second derivative restricted by condition $|d^2E/dt^2|<A/T^2$ in each time point of the envelope, wherein $E(t)$ is the envelope curve, t is time, A is the maximum amplitude of the at least one ultrasonic signal and T is the period of the base frequency of the at least one ultrasonic signal;
receiving the at least one ultrasonic signal by the mobile device at a receipt time, and
determining the animal position using:
the known location of the at least one ultrasonic emitter and
a time difference between emission and reception of the at least one ultrasonic signal emitted from the at least one ultrasonic emitter.

2. A method of detecting a position of an animal, the method comprising:
attaching a mobile device to the animal, wherein the mobile device comprises an ultrasonic receiver;
emitting at least one ultrasonic signal as a pulse from at least one ultrasonic emitter at a known location at a transmission time, wherein oscillations of voltage or current at the at least one ultrasonic emitter during pulse transmission has an envelope described by the function $$E(t) = B \cdot \left( \left( \sin^\alpha\left(\frac{\pi t}{T}\right) \right) + \delta(t) \right),$$

where $E(t)$ is the instantaneous amplitude of voltage or current at the at least one ultrasonic emitter, t is time counted from the start of the envelope, B is the maximum amplitude of voltage or current at the at least one ultrasonic emitter, $\alpha$ is a positive constant, $\pi$ is the mathematical constant 3.14159 . . . , T is the duration of the envelope and $\delta(t)$ is any function of time or random noise with an absolute value smaller than 0.25 (i.e., $|\delta(t)|<0.25$ for any t from the interval $[0, T]$);
receiving the at least one ultrasonic signal by the mobile device at a receipt time,
determining the animal position using:
the known location of the at least one ultrasonic emitter and
a time difference between the transmission time and the receipt time of the at least one ultrasonic signal.

3. The method of claim 1 or 2, wherein the at least one ultrasonic emitter with the known location, is stationary.

4. The method of claim 1 or 2, wherein ambient temperature, ambient humidity or both are measured to compute sound speed in the air.

5. The method of claim 1 or 2, wherein the mobile device comprises a radio transmitter, wherein the at least one ultrasonic emitter has a wired connection with a computer, and wherein the radio transmitter transmits a radio signal containing information on the at least one ultrasonic signal arrival to the computer.

6. The method of claim 5, wherein the at least one ultrasonic emitter comprises three ultrasonic emitters which are connected to a controlling module that periodically activates the ultrasonic emitters in a known fixed sequence.

7. The method of claim 5, wherein the method is performed for several animals using more than one ultrasonic emitter and more than one radio transmitter with slightly different carrier frequencies.

8. The method of claim 1 or 2, wherein the mobile device comprises local memory and an IR receiver, and wherein a synchronizing IR emitter is used for sending an IR strobe pulse to the mobile device, and wherein the mobile device stores information on the at least one ultrasonic signal and the IR synchronizing strobe pulse in its local memory for further downloading and analysis.

9. The method of claim 8, wherein the at least one ultrasonic emitter comprises three ultrasonic emitters, providing 3D tracking of the animal.

10. The method of claim 1 or 2 wherein the at least one ultrasonic emitter comprises four ultrasonic emitters generating ultrasonic signals, and wherein a computer computes the position of the mobile device from the stored information on the ultrasonic signals in a way similar to computing coordinates in a GPS receiver.

11. The method of claim 10 wherein the mobile device comprises a local memory and the stored information on the ultrasonic signal arrivals is stored in the local memory of the mobile device for further downloading and analysis.

12. The method of claim 10 wherein the mobile device comprises a radio transmitter, and the radio transmitter transmits a radio signal containing information on the ultrasonic signal arrivals to the computer, and the computer stores information on the ultrasonic signal arrivals.

13. The method of claim 1 or 2, wherein the ultrasonic receiver comprises a wide-band microphone capable of receiving the ultrasonic signal and an animal vocalization in an audio-band, and wherein after receiving the ultrasonic signal and the animal vocalization by the mobile device the ultrasonic signal and the animal vocalization are separated by analog filtration, digital filtration or both.

14. The method of claim 13, wherein the animal vocalization is separated from the at least one ultrasonic signal and stored for further analysis, and wherein the separated at least one ultrasonic signal is further amplified by an amplifier.

15. The method of claim 1 or 2, wherein the mobile device additionally comprises a sensor selected from an accelerometer, a gyroscope, and a magnetometer, or any combination thereof for measuring orientation of the animal body.

16. The method of claim 1 or 2, wherein the mobile device additionally comprises a light sensor and wherein at least one optical scanning transmitter mounted over an area in which the position of the animal is detected, transmits at least one rotating planar scanning light beam, and wherein the at least one ultrasonic emitter is placed at an axis of rotation of the at least one rotating planar scanning light beam thus providing an altitude of the mobile device, with the altitude calculated from the known location of the at least one ultrasonic emitter and the time difference between the transmission time and the receipt time of the at least one ultrasonic signal.

17. The method of claim 16, wherein the at least one optical scanning transmitter comprises two scanning optical transmitters which transmit two rotating planar scanning light beams at an angle thus providing the position of the animal in a horizontal 2D plane,
and wherein the at least one ultrasonic emitter provides an altitude of the mobile device, with the altitude calculated from the known location of the at least one ultrasonic emitter and the time difference between the transmission time and the receipt time of the at least one ultrasonic signal.

18. The method of claim 17, wherein the at least two rotating planar scanning light beams have their axes of rotation being at angle to each other and intersecting each other, and wherein the at least one ultrasonic emitter is placed at the intersection of the axes of rotation of the at least two rotating planar scanning light beams.

19. The method of claim 16, wherein the at least one rotating planar scanning light beam is produced by a rotating mirror or a prism.

20. A system for detecting a position of an animal comprising:
at least one ultrasonic emitters with a known locations, configured to generate at least one ultrasonic signal as a pulse at a predetermined time, wherein the at least one ultrasonic signal has an envelope with a shape that is chosen with the first derivative restricted by condition $|dE/dt|<A/T$ and/or with the second derivative restricted by condition $|d^2E/dt^2|<A/T^2$ in each time point of the envelope, wherein E(t) is the envelope curve, t is time, A is the maximum amplitude of the at least one ultrasonic signal and T is the period of the base frequency of the at least one ultrasonic signal; and
at least one mobile device attached to the animal, wherein the at least one mobile device is configured to receive the at least one ultrasonic signal from the at least one ultrasonic emitters with the known location; and
a processing module computing a time difference between emission and reception of the at least one ultrasonic signal emitted from the at least one ultrasonic emitters to determine the position of the animal.

21. A system for detecting a position of an animal comprising:
at least one ultrasonic emitter with a known location, configured to generate at least one ultrasonic signal as a pulse at a predetermined time, wherein oscillations of voltage or current at the at least one ultrasonic emitter during pulse transmission has an envelope described by the function $$E(t) = B \cdot \left( \left( \sin^\alpha\left(\frac{\pi t}{T}\right) \right) + \delta(t) \right),$$

where E(t) is the instantaneous amplitude of voltage or current at the at least one ultrasonic emitter, t is time counted from the start of the envelope, B is the maximum amplitude of voltage or current at the at least one ultrasonic emitter, α is a positive constant, π is the mathematical constant 3.14159..., T is the duration of the envelope and δ(t) is any function of time or random noise with an absolute value smaller than 0.25 (i.e., $|\delta(t)|<0.25$ for any t from the interval [0, T]); and at least one mobile device attached to the animal, wherein the at least one mobile device is configured to receive at least one ultrasonic signals from the at least one ultrasonic emitter with the known location; and a processing module computing a time difference between the transmission time and the receipt time of the at least one ultrasonic signal to determine the position of the animal.

22. The system of claim 20, wherein the at least one ultrasonic emitter is stationary.

23. The system of claim 20 or 21, wherein the at least one mobile device comprises a radio transmitter, wherein the at least one ultrasonic emitter has a wired connection with a computer.

24. The system of claim 20 or 21, wherein the at least one mobile device comprises local memory and an IR receiver, and wherein the system comprises a synchronizing IR emitter for sending an IR strobe pulse to the at least one mobile device.

25. The system of claim 20 or 21, wherein the at least one mobile device comprises a wide-band microphone capable of receiving the ultrasonic signal and an animal vocalization in an audio-band, and wherein an analog filter, a digital filter or both are used for separation of the ultrasonic signal and the animal vocalization.

26. The system of claim 25, wherein the analog filter is a Sallen-Key filter, a multiple feedback filter or a combination of both.

27. The system of claim 25, wherein the filter is a finite impulse response (FIR) filter, an infinite impulse response (IIR) filter or a combination of both.

28. The system of claim 20 or 21, wherein the mobile device additionally comprises a sensor selected from an accelerometer, a gyroscope, and a magnetometer, or any combination thereof for measuring orientation of the animal body.

29. The system of claim 20 or 21, wherein the at least one mobile device comprises several mobile devices and system comprises at least one radio receiver, and wherein each mobile device comprises at least one radio transmitter working at a different carrier frequency.

30. The system of claim 20 or 21, wherein the mobile device additionally comprises a light sensor and wherein at least one optical scanning transmitter, mounted over an area in which the position of the animal is detected, transmits at least one rotating planar scanning light beam, and wherein the at least one ultrasonic emitter is placed at an axis of rotation of the at least one rotating planar scanning light beam thus providing an altitude of the mobile device, with the altitude calculated from the known location of the at least one ultrasonic emitter and the time difference between the transmission time and the receipt time of the at least one ultrasonic signal.

31. The system of claims 30, wherein the at least one optical scanning transmitter comprises two scanning optical transmitters which transmit two rotating planar scanning light beams at an angle thus providing the position of the animal in a horizontal 2D plane, and wherein the at least one ultrasonic emitter provides an altitude of the mobile device, with the altitude calculated from the known location of the at least one ultrasonic emitter and the time difference between the transmission time and the receipt time of the at least one ultrasonic signal.

32. The system of claim 31, wherein the at least two rotating planar scanning light beams have their axes of rotation being at angle to each other and intersecting each other, and wherein the at least one ultrasonic emitter is placed at the intersection of the axes of rotation of the at least two rotating planar scanning light beams.

33. The system of claim 30, wherein the at least one rotating planar scanning light beam is produced by a rotating mirror or a prism.

\* \* \* \* \*